(12) United States Patent
Nathwani et al.

(10) Patent No.: US 12,331,331 B2
(45) Date of Patent: Jun. 17, 2025

(54) POLYNUCLEOTIDES

(71) Applicant: SPUR THERAPEUTICS LIMITED, Stevenage (GB)

(72) Inventors: Amit Nathwani, Rickmansworth (GB); Jenny McIntosh, Epsom (GB); Romuald Corbau, St Albans (GB); Azadeh Kia, Enfield (GB); Carlos Miranda, Watford (GB)

(73) Assignee: SPUR THERAPEUTICS LIMITED, Stevenage (GB)

( * ) Notice: Subject to any disclaimer, the term of this patent is extended or adjusted under 35 U.S.C. 154(b) by 14 days.

(21) Appl. No.: 17/428,344

(22) PCT Filed: Feb. 4, 2020

(86) PCT No.: PCT/GB2020/050251
§ 371 (c)(1),
(2) Date: Aug. 4, 2021

(87) PCT Pub. No.: WO2020/161483
PCT Pub. Date: Aug. 13, 2020

(65) Prior Publication Data
US 2022/0154159 A1 May 19, 2022

(30) Foreign Application Priority Data

Feb. 4, 2019 (GB) ..................................... 1901512
Dec. 6, 2019 (GB) ..................................... 1917910

(51) Int. Cl.
*C12N 9/24* (2006.01)
*A61K 38/47* (2006.01)
*A61P 1/16* (2006.01)
*C12N 15/52* (2006.01)

(52) U.S. Cl.
CPC ............ *C12N 9/2402* (2013.01); *A61K 38/47* (2013.01); *A61P 1/16* (2018.01); *C12N 15/52* (2013.01); *C12Y 302/01045* (2013.01)

(58) Field of Classification Search
None
See application file for complete search history.

(56) References Cited

U.S. PATENT DOCUMENTS

| | | | |
|---|---|---|---|
| 5,911,983 A | 6/1999 | Barranger et al. | |
| 6,582,692 B1 | 6/2003 | Podsakoff et al. | |
| 6,696,272 B1 | 2/2004 | Mahuran et al. | |
| 7,452,716 B2 | 11/2008 | Yew | |
| 10,041,137 B2* | 8/2018 | Kinoshita | A61P 21/00 |
| 10,772,975 B2* | 9/2020 | Bancel | A61P 1/04 |
| 2002/0090719 A1 | 7/2002 | Yew | |
| 2004/0009151 A1 | 1/2004 | Kay et al. | |
| 2005/0265988 A1 | 12/2005 | Choi et al. | |
| 2006/0104954 A1 | 5/2006 | Podsakoff et al. | |
| 2006/0188482 A1 | 8/2006 | Kay et al. | |
| 2016/0060656 A1 | 3/2016 | Rebar | |
| 2016/0237414 A1 | 8/2016 | Grabowski et al. | |
| 2017/0157220 A1 | 6/2017 | Do | |
| 2018/0117181 A1 | 5/2018 | Huston | |
| 2018/0243370 A1 | 8/2018 | Pandey | |
| 2022/0154159 A1 | 5/2022 | Nathwani et al. | |

FOREIGN PATENT DOCUMENTS

| | | |
|---|---|---|
| CN | 102264349 A | 11/2011 |
| CN | 105555317 A | 5/2016 |
| CN | 105745326 A | 7/2016 |
| CN | 107106689 A | 8/2017 |
| CN | 107429257 A | 12/2017 |
| EP | 1027069 B1 | 7/2006 |
| EP | 2492347 A1 | 8/2012 |
| EP | 3702466 A1 | 9/2020 |
| JP | 2013-048624 A2 | 3/2013 |
| JP | 2015-006205 A2 | 1/2015 |
| JP | 2018-011597 A2 | 1/2018 |
| WO | WO-0136603 A2 | 5/2001 |
| WO | WO-0149830 A2 | 7/2001 |
| WO | WO2005005610 A2 | 1/2005 |
| WO | WO-2008144591 A2 | 11/2008 |
| WO | WO-2008154198 A1 | 12/2008 |
| WO | WO-2009038695 A1 | 3/2009 |
| WO | WO-2010099960 A2 | 9/2010 |
| WO | WO-2011122950 A1 | 10/2011 |
| WO | WO-2012064709 A2 | 5/2012 |
| WO | WO-2015162302 A2 | 10/2015 |

(Continued)

OTHER PUBLICATIONS

Bauer et al., 2010 "The impact of intragenic CpG content on gene expression" Nucleic Acids Research, Jul. 2010, vol. 38, pp. 3891-3908.
Berger et al., 2018. "Intra-monocyte Pharmacokinetics of Imiglucerase Supports a Possible Personalized Management of Gaucher Disease Type 1" Clinical Pharmacokinetics. Apr. 2019 vol. 58 pp. 469-482. Epub Aug. 21, 2018.
Binny et al., 2012 "Vector Systems for Prenatal Gene Therapy: Principles of Adeno-Associated Virus Vector Design and Production" Methods in Molecular Biology, Apr. 25, 2012 pp. 109-131 vol. 891.
Chen et al., 2005 "Improved Production and Purification of Minicircle DNA Vector Free of Plasmid Bacterial Sequences and Capable of Persistent Transgene Expression in Vivo" Human Gene Therapy, Jan. 2005 pp. 126-131 vol. 16 No. 1.
Chiorini J.A. et al. Cloning of adeno-associated virus type 4 (AAV4) and generation of recombinant AAV4 particles. Journal of Virology, 71:6823-6833 (1997).

(Continued)

*Primary Examiner* — Hope A Robinson
(74) *Attorney, Agent, or Firm* — Baker, Donelson, Bearman, Caldwell & Berkowitz, P.C.

(57) ABSTRACT

The present invention relates to polynucleotides comprising a GBA nucleotide sequence that encodes a GCase protein or fragment thereof and wherein a portion of the coding sequence is not wild type. The present invention further relates to viral particles comprising a recombinant genome comprising the polynucleotide of the invention, compositions comprising the polynucleotides or viral particles, and methods and uses of the polynucleotides, viral particles or compositions.

7 Claims, 22 Drawing Sheets
Specification includes a Sequence Listing.

(56) References Cited

FOREIGN PATENT DOCUMENTS

| WO | WO-2015168666 A2 | 11/2015 |
| WO | WO-2016128722 A1 | 8/2016 |
| WO | WO-2016179497 A1 | 11/2016 |
| WO | WO-2017103612 A1 | 6/2017 |
| WO | WO-2017165766 A2 | 9/2017 |
| WO | WO-2018152333 A1 | 8/2018 |
| WO | WO2018206168 A1 | 11/2018 |
| WO | WO-2019009979 A1 | 1/2019 |
| WO | WO-2019043081 A1 | 3/2019 |
| WO | WO-2019060649 A1 | 3/2019 |
| WO | WO-2019070891 A1 | 4/2019 |
| WO | WO-2019070893 A1 | 4/2019 |
| WO | WO-2019070894 A1 | 4/2019 |
| WO | WO-2019073059 A1 | 4/2019 |
| WO | WO-2019210267 A2 | 10/2019 |
| WO | WO-2020012149 A1 | 1/2020 |
| WO | WO-2020012164 A1 | 1/2020 |
| WO | WO-2020077114 A2 | 4/2020 |
| WO | WO-2020102667 A2 | 5/2020 |
| WO | WO-2020118056 A1 | 6/2020 |
| WO | WO-2020157248 A1 | 8/2020 |
| WO | WO-2020210615 A1 | 10/2020 |
| WO | WO-2020210713 A1 | 10/2020 |
| WO | WO-2021028299 A1 | 2/2021 |
| WO | WO-2021048034 A1 | 3/2021 |
| WO | WO-2021199039 A1 | 10/2021 |

OTHER PUBLICATIONS

Chiorini, J.A. JA et al. Cloning and characterization of adeno-associated virus type 5, Journal of Virology 73:1309-1319 (1999).

Chowdary et al., 2018. "A Single Intravenous Infusion of FLT180a Results in Factor IX Activity Levels of More Than 40% and Has the Potential to Provide a Functional Cure for Patients with Haemophilia B" Blood, 2018, p. 631 vol. 132 Suppl. 1.

Clemence et al., 2017. "Sanofi Initiates Phase 2 Clinical Trial to Evaluate Therapy for Genetic Form of Parkinson's Disease" Genzyme press release, Feb. 14, 2017.

Dahl et al., 2015. "Lentiviral Gene Therapy Using Cellular Promoters Cures Type 1 Gaucher Disease in Mice" Molecular Therapy, May 2015, vol. 23 No. 5, pp. 835-844.

Dane et al., 2018. "Preclinical Evaluation of an Engineered AAV Capsid in Non-Human Primates for the Treatment of Haemophilia B" Blood, Dec. 2018 p. 2197 vol. 132 Supp. 1.

Debinski et al. 2009. "Convection-enhanced delivery for the treatment of brain tumors" Expert Rev Neurother Jan. 9, 2009, vol. 9 No. 10, pp. 1519-1527.

Dvir et al., 2003. "X-ray structure of human acid-beta-glucosidase, the defective enzyme in Gaucher disease" EMBO, 2003. vol. 4 No. 7, pp. 704-709.

European Medicines Agency, 2014. "Gaucher disease: a strategic collaborative approach from EMA and FDA" May 12, 2014. https://www.ema.europa.eu/docs/en_GB/document_library/Regulatory_and_procedural_guideline/2014/05/WC500166587.pdf.

Faust et al., 2013a "CpG-depleted adeno-associated virus vectors evade immune detection" Journal of Clinical Investigation, Jul. 1, 2013 pp. 2994-3001 vol. 123 No. 7.

Faust, Susan M., et al., "Escaping Immune Activation Through the Use of CPG-Depleted AAV Vectors" Molecular Therapy vol. 21, Supplement 1, May 2013.

Frumkin et al., 2018 "Codon usage if highly expressed genes affects proteome-wide translation efficiency" PNAS, May 7, 2018 pp. E4940-E4949 vol. 115 No. 21.

Gao et al., 2020. "Prediction of disulfide bond engineering sites using a machine learning method" Scientific Reports, Jun. 25, 2020 vol. 10 No. 1, pp. 10330.

Gorman et al., 2002. "Protein disulfide bond determination by mass spectrometry" Mass Spectrometry Reviews May 2002, vol. 21, No. 3, pp. 183-216.

Grace et al., 1999. "Non-pseudogene-derived complex acid β-glucosidase mutations causing mild type 1 and severe type 2 Gaucher disease" Journal of Clinical Investigation Mar. 1999, vol. 103, No. 6, pp. 817-823.

Gupta and Pastores, 2018. "Pharmacological treatment of pediatric Gaucher disease" Expert Review of Clinical Pharmacology, Dec. 3, 2018, pp. 1183-1194 vol. 11 No. 12.

Haas et al. Codon usage limitation in the expression of HIV-1 envelope glycoprotein, Current Biology 6(3):315-324 (1996).

Hafenrichter et al., 1994. "Liver-directed gene therapy: evaluation of liver specific promoter elements" Journal of Surgical Research, Jun. 1994, vol. 56 No. 6, pp. 510-517.

Hodges BL, et al., "Long-Term Transgene Expression From Plasmid DNA Gene Therapy Vectors is Negatively Affected by CPG Dinucleotides", Molecular Therapy. 10(2):269-278 (2004).

Hruska et al., 2008. "Gaucher disease: Mutation and polymorphism spectrum in the glucocerebrosidase gene (GBA)" Human Mutations, May 2008, vol. 29 No. 5, pp. 567-583.

Hyde, Stephen C., et al., "CPG-Free Plasmids Confer Reduced Inflammation and Sustained Pulmonary Gene Expression", Nature Biology (2008) 26: 549-551.

Inouye et al. "Protein expression of preferred human codon-optimized Gaussia luciferase genes with an artificial open-reading frame in mammalian and bacterial cells." Protein Expression and Purification 128 (2016) 93-100.

Jeyakumar et al., 2019. "Liver-directed gene therapy corrects Fabry disease in mice" Molecular Genetics and Metabolism, Feb. 2019, vol. 126 Supp. S80.

Krinner et al., 2014 "CpG domains downstream of TSSs promote high levels of gene expression" Nucleic Acids Research, Apr. 2014, vol. 42, pp. 3551-3564.

Lieberman 2011. "A Guided Tour of the Structural Biology of Gaucher Disease: Acid-beta-Glucosidase and Saposin C" Enzyme Research, Nov. 22, 2011, vol. 2011, pp. 1-15.

Linari et al., 2015. "Clinical manifestations and management of Gaucher disease" Clinical Cases in Mineral and Bone Metabolism, May-Aug. 2015, vol. 12 No. 2, pp. 157-164.

Marshall et al., 2002. "Demonstration of Feasibility of In Vivo Gene Therapy for Gaucher Disease Using a Chemically Induced Mouse Model" Molecular Therapy, Aug. 2002, vol. 6 No. 2, pp. 179-189.

Marshall et al., 2004. "Feasibility of AAV-Mediated Gene Therapy Examined Using a New Murine Model (D409V/null) of Gaucher Disease" Molecular Therapy, May 2004, vol. 9 Suppl. 1, pp. S324-S325.

Mauro "Codon Optimization in the Production of Recombinant Biotherapeutics: Potential Risks and Considerations "BioDrugs (2018) 32:69-81.

McEachern et al., 2006. "AAV8-mediated expression of glucocerebrosidase ameliorates the storage pathology in the visceral organs of a mouse model of Gaucher disease" Journal of Gene Medicine, Jun. 2006;8(6):719-29. ePub Mar. 10, 2006.

McIntosh J. et al. Therapeutic levels of FVIII following a single peripheral vein administration of rAAV vector encoding a novel human factor VIII variant. Blood 121(17):3335-44 (Apr. 25, 1993).

Miao, C.H. et al. Inclusion of the hepatic locus control region, an intron, and untranslated region increases and stabilizes hepatic factor IX gene expression in vivo but not in vitro. Mol Ther. 1(6):522-32(Jun. 2000).

Miranda et al., 1990. "Activity of glucocerebrosidase in extracts of different cell types from type 1 Gaucher disease patients" Clinical Genetics, 1990, vol. 38 pp. 218-227.

Miranda et al., 2019. "Liver directed AAV gene therapy to treat Gaucher disease" Molecular Genetics and Metabolism vol. 126 No. 2 pp. S100.

Miranda et al., 2019. "Liver-directed AAV Gene Therapy for Gaucher Disease" Blood, Nov. 13, 2019, vol. 134 Suppl. 1 pp. 3354.

Miranda et al., 2020. "One-off liver directed AAV gene therapy achieves long term uptake of acid beta-glucocerebrosidase by macrophages of affected tissues in Gaucher disease" Molecular Genetics and Metabolism Jan. 31, 2020, vol. 129 No. 2, p. S110.

Mistry et al., 2017. "Gaucher disease: Progress and ongoing challenges" Molecular Genetics and Metabolism, Jan.-Feb. 2017;120(1-2):8-21. Epub Nov. 17, 2016.

(56) References Cited

OTHER PUBLICATIONS

Nair et al., 2011 "Effect of different UCOE-promoter combinations in creation of engineered cell lines for the production of Factor VIII" BMC Research Notes, Jun. 10, 2011 Vol. 4 Art. 178.

Nathwani, A.C. et al. Self-complementary adeno-associated virus vectors containing a novel liver-specific human factor IX expression cassette enable highly efficient transduction of murine and nonhuman primate liver. Blood, 107(7): 2653-2661 (Apr. 1, 2006).

Needleman and Wunsch "A general method applicable to the search for similarities in the amino acid sequence of two proteins", J Mol Biol. Mar. 1970; 48(3); 443-53.

Nienhuis et al., 2017. "Gene Therapy for Hemophilia" Molecular Therapy, . May 3, 2017;25(5):1163-1167. Epub Apr. 11, 2017.

Okuyama T. et al. Liver-directed gene therapy: a retroviral vector with a complete LTR and the ApoE enhancer-alpha 1-antitrypsin promoter dramatically increases expression of human alpha 1-antitrypsin in vivo. Human Gene Therapy 7(5):637-45 (Mar. 20, 1996).

Ortolano et al. Treatment of lysosomal storage diseases: recent patents and future strategies. Recent Pat Endocr Metab Immune Drug Discov 8(1):9-25 (2014).

Puigbo. Optimizer: a web server for optimizing the codon usage of DNA sequences. Nucleic Acid Research, 35(14):126-131, 2007.

Rutledge, E.A. et al. Infectious clones and vectors derived from adeno-associated virus (AAV) serotypes other than AAV type 2. Journal of Virology 72:309-319 (1998).

Satya et al., 2003"A Pattern Matching Algorithm for Codon Optimization and CpG Motif-Engineering in DNA Expression Vectors" Proceeding IEEE Computer Society Bioinformatic Conference, 2003 pp. 294-305 vol. 2.

Sinclair et al., 2002. "Synonymous codon usage bias and the expression of human glucocerebrosidase in the methylotrophic yeast, Pichia pastoris" Protein Expression & Purification, Oct. 2002, vol. 26 No. 1 pp. 96-105.

Srivastava, A. et al. Nucleotide sequence and organization of the adeno-associated virus 2 genome, Journal of Virology 45(2): 555-64(Feb. 1983).

Wagner et al., 2018. "Attitudes of Individuals with Gaucher Disease toward Substrate Reduction Therapies" Journal of Genetic Counselling, Feb. 2018;27(1):169-176. Epub Aug. 13, 2017.

Wang et al. Sustained correction of bleeding disorder in hemophilia B mice by gene therapy. Proc Natl Acad. Sci. USA 96(7): 3906-3910 (Mar. 30, 1999).

Wang et al., 2011. "Lysosomal storage diseases: diagnostic confirmation and management of presymptomatic individuals" Genetics in Medicine, May 2011, vol. 13 No. 5 pp. 457-484.

Wang et al., 2019. "Adeno-associated virus vector as a platform for gene therapy delivery" Nature Reviews Drug Discovery, May 2019, vol. 18 No. 5 pp. 358-378.

Watanabe et al., 2018. "Rational protein design for thermostabilization of glycoside hydrolases based on structural analysis" Appl Microbiol Biotechnol, Oct. 2018; 102(20):8677-8684. Epub Aug. 14, 2018.

Welch et al. You're one in a googol: optimizing genes for protein expression, J.R. Soc. Interface 6(Suppl. 4):S467-76(Aug. 9, 2009). E-published: Mar. 11, 2009.

Wu, et al., Optimization of Self-complementary AAV Vectors for Liver-directed Expression Results in Sustained Correction of Hemophilia B at Low Vector Dose, Mol Ther. Feb. 2008; vol. 16(2), pp. 280-289.

Wu, P. et al. Mutational analysis of the adeno-associated virus type 2 (AAV2) capsid gene and construction of AAV2 vectors with altered tropism. Journal of Virology, 74(18):8635-47 (Sep. 2000).

Xu et al., 2003. "Viable mouse models of acid beta-glucosidase deficiency: the defect in Gaucher disease" The American Journal of Pathology, Nov. 2003, vol. 163 No. 5 pp. 2093-2101.

Xu et al., 2010. "Comparative therapeutic effects of velaglucerase alfa and imiglucerase in a Gaucher disease mouse model" Public Library of Science, May 20, 2010, vol. 5 No. 5 pp. e10750.

Yew et al., 2002 "CpG-depleted Plasmid DNA Vectors With Enhanced Safety and Long-Term Gene Expression in Vivo" Molecular Therapy, Jun. 2002 pp. 731-738 vol. 5 No. 6.

Zanta-Boussif et al., Validation of a mutated PRE sequence allowing high and sustained transgene expression while abrogating WHV-X protein synthesis: application to the gene therapy of WAS. Gene Therapy 16(5):605-619 (2009).

Zincarelli et al. Analysis of AAV serotypes 1-9 mediated gene expression and tropism in mice after systemic injection. Mol Ther 16:1073-1080 (2008).

Alfonso et al.: Expression and functional characterization of mutated glucocerebrosidase alleles causing Gaucher disease in Spanish patients. Blood Cells Mol Dis. 32(1):218-225 (2004).

Alfonso et al.: Miglustat (NB-DNJ) works as a chaperone for mutated acid beta-glucosidase in cells transfected with several Gaucher disease mutations. Blood Cells Mol Dis. 35(2):268-276 (2005).

Alfonso et al.: Mutation analysis and genotype/phenotype relationships of Gaucher disease patients in Spain. J Hum Genet. 52(5):391-396 (2007).

Alfonso et al.: Mutation prevalence among 51 unrelated Spanish patients with Gaucher disease: identification of 11 novel mutations. Blood Cells Mol Dis. 27:(5):882-891 (2001).

Ankleshwaria et al.: Novel mutations in the glucocerebrosidase gene of Indian patients with Gaucher disease. Journal of Human Genetics. 59:223-228 (2014).

Bailey et al.: Combination therapy (eliglustat + velaglucerase alfa) in a pediatric patient with Gaucher disease type 1 and hereditary spherocytosis. Molecular Genetics and Metabolism. 114(2):S17 (2015).

Barton et al.: Replacement therapy for inherited enzyme deficiency—macrophage-targeted glucocerebrosidase for Gaucher's disease. N. Engl. J. Med. 324:1464-1470 (1991).

Beutler: Enzyme replacement in Gaucher disease. PLoS Med. 1:e21 (2004).

Beutler et al.: Enzyme-replacement therapy for Gaucher's disease. New England Journal of Medicine. 325:1809-1811 (1991).

Bove et al.: Pathological findings in Gaucher disease type 2 patients following enzyme therapy. Hum. Pathol. 26:1040-1045 (1995).

Charrow et al.: The Gaucher registry: demographics and disease characteristics of 1698 patients with Gaucher disease. Arch. Intern. Med. 160:2835-2843 (2000).

Comper et al.: Generation of [beta]-Glucocerebrosidase variants with increased half-life in human plasma for liver directed AAV gene therapy aimed at the treatment of Gaucher disease type 1. Molecular Genetics and Metabolism, Academic Press, Amsterdam, NL. 132(2) (2021).

Craig et al.: Disulfide by Design 2.0: a web-based tool for disulfide engineering in proteins. BMC Bioinformatics, Biomed Central, London, GB. 14(1):346 1-7 (2013).

Demina et al.: Six new Gaucher disease mutations. Acta Haematol. 99(2):80-82 (1998).

Dombkowski et al.: Protein disulfide engineering. FEBS Letters, Elsevier, Amsterdam, NL. 588(2):206-212 (2013).

Evren et al.: Distinct developmental pathways from blood monocytes generate human lung macrophage diversity. Immunity. 54:259-275 e257 (2021).

Fallet et al.: Enzyme augmentation in moderate to life-threatening Gaucher disease. Pediatr. Res. 31:496-502 (1992).

Figueroa et al.: A less costly regimen of alglucerase to treat Gaucher's disease. N. Engl. J. Med. 327:1632-1636 (1992).

Filocamo et al.: Analysis of the Glucocerebrosidase Gene and Mutation Profile in 144 Italian Gaucher Patients. Hum Mutat. 20(3):234-235 (2002).

Gary et al.: Recent advances in the diagnosis and management of Gaucher disease. Expert Rev. Endocrinol. Metab. 13:107-118 (2018).

Gegg and Schapira. The role of glucocerebrosidase in Parkinson disease pathogenesis. The FEBS Journal. 285(19):3591-3603 (2018).

Hoitsema et al.: Identification of novel splice site mutation IVS9 + 1(G > A) and novel complex allele G355R/R359X in Type 1 Gaucher patients heterozygous for mutation N370S. Meta Gene. 23(9):47-51 (2016).

(56) References Cited

OTHER PUBLICATIONS

Kallemeijn et al.: Investigations on therapeutic glucocerebrosidases through paired detection with fluorescent activity-based probe. PLoS One. 12:e0170268 (2017).
Kim et al.: Gaucher disease: identification of three new mutations in the Korean and Chinese (Taiwanese) populations. Hum Mutat. 7(3):214-218 (1996).
Koprivica et al.: Analysis and Classification of 304 Mutant Alleles in Patients with Type 1 and Type 3 Gaucher Disease. Am. J. Hum. Genet. 66:1777-1786 (2000).
Malini et al.: Functional analysis of 11 novel GBA alleles. Eur J Hum Genet. 22(4):511-516 (2014).
Manickam et al.: In silico identification of genetic variants in glucocerebrosidase (GBA) gene involved in Gaucher's disease using multiple software tools. Front Genet. 5:148 (2014).
Manini et al.: Adeno-associated virus (AAV)-mediated gene therapy for Duchenne muscular dystrophy: the issue of transgene persistence. Front. Neurol. 12:814174 (2021).
Massaro et al.: Gene therapy for lysosomal storage disorders: ongoing studies and clinical development. Biomolecules. 11:611 (2021).
McIntosh et al.: Therapeutic levels of FVIII following a single peripheral vein administration of rAAV vector encoding a novel human factor VIII variant. Blood 121(17):3335-3344 (Apr. 25, 2013).
Mehta: Gaucher disease: unmet treatment needs. Acta. Paediatr. 97:83-87 (2008).
Nagree et al.: An update on gene therapy for lysosomal storage disorders. Expert Opin. Biol. Ther. 19:655-670 (2019).
Nalysnyk et al.: Gaucher disease epidemiology and natural history: a comprehensive review of the literature. Hematology. 22:65-73 (2017).
Salam et al.: Structure-based approach to the prediction of disulfide bonds in proteins. Protein Engineering, Design and Selection. 27(10):365-374 (2014).
Pastores et al.: Gaucher Disease. GeneReviews (eds. M.P. Adam et al.) (University of Washington, Seattle (WA); 2000 [updated 2018]).
Rangarajan et al.: AAV5-Factor VIII gene transfer in severe hemophilia A. N Engl J Med. 377:2519-2530 (2017).
Shawky et al.: Treatment options for patients with Gaucher disease. Egyptian Journal of Medical Human Genetics. 17:281-285 (2016).
Sheth: Molecular study of lysosomal storage disorders in India. Mol Cytogenet. 7(Suppl 1):I30 (2014).
Simonaro et al.: Lysosomes, lysosomal storage diseases, and inflammation. J. Inborn Errors Metab. Screen. 4:2326409816650465 (2016).
Smith et al.: Insights into the structural biology of Gaucher disease. Experimental Neurology. 298:180-190 (2017).
Stirnemann et al.: A Review of Gaucher Disease Pathophysiology, Clinical Presentation and Treatments. International Journal of Molecular Sciences. 18(2):E441 (2017).
Sun et al.: Systemic enzyme delivery by blood-brain barrier-penetrating SapC-DOPS nanovesicles for treatment of neuronopathic Gaucher disease. EBioMedicine. 55:102735 (2020).
Tekoah et al.: Glycosylation and functionality of recombinant beta-glucocerebrosidase from various production systems. Biosci Rep 33 (2013).
Tsai et al.: Mutation analysis of type II Gaucher disease in five Taiwanese children: identification of two novel mutations. Acta Paediatr Taiwan. 42(4):231-235 (2001).
Weinreb et al.: Gaucher disease type 1 patients from the ICGG Gaucher Registry sustain initial clinical improvements during twenty years of imiglucerase treatment. Mol. Genet. Metab. 132:100-111 (2021).
Weinreb et al.: Long-term clinical outcomes in type 1 Gaucher disease following 10 years of imiglucerase treatment. J. Inherit. Metab. Dis. 36:543-553 (2013).
Wright et al.: The mannose receptor (CD206) identifies a population of colonic macrophages in health and inflammatory bowel disease. Sci Rep 11:19616 (2021).
Wyatt et al.: The effectiveness and cost-effectiveness of enzyme and substrate replacement therapies: a longitudinal cohort study of people with lysosomal storage disorders. Health Technol. Assess. 16:1-543 (2012).
Zhong et al.: Efficient and Targeted Transduction of Nonhuman Primate Liver With Optimized AAV3B Vectors Through Systemic Delivery. Mol Ther. 22(S1): S91 (2014).
Mendell et al. Phase 1/2a Trial of SRP-9001 in Patients with Duchenne Muscular Dystrophy: 3-Year Safety and Functional Outcomes (S23.004). Neurology 98:2568 (2022).
Shukla et al.: Parkinson Disease Overview. GeneReviews 1-14 (2004) (University of Washington, Seattle (WA) [updated 2019]).
Japanese Patent Application No. 2021-545956 Reason for Refusal dated Jan. 26, 2024.
Chinese Patent Application No. 20208001755 First Office Action dated Feb. 29, 2024.
Wu, H. et al. Platelet transfusion refractoriness caused by GBA gene mutation in one patient with Gaucher disease Journal: Chinese Journal of Clinical Laboratory Science Year 2017, vol. 35, Issue 5, p. 330-333.

\* cited by examiner

FIG. 2
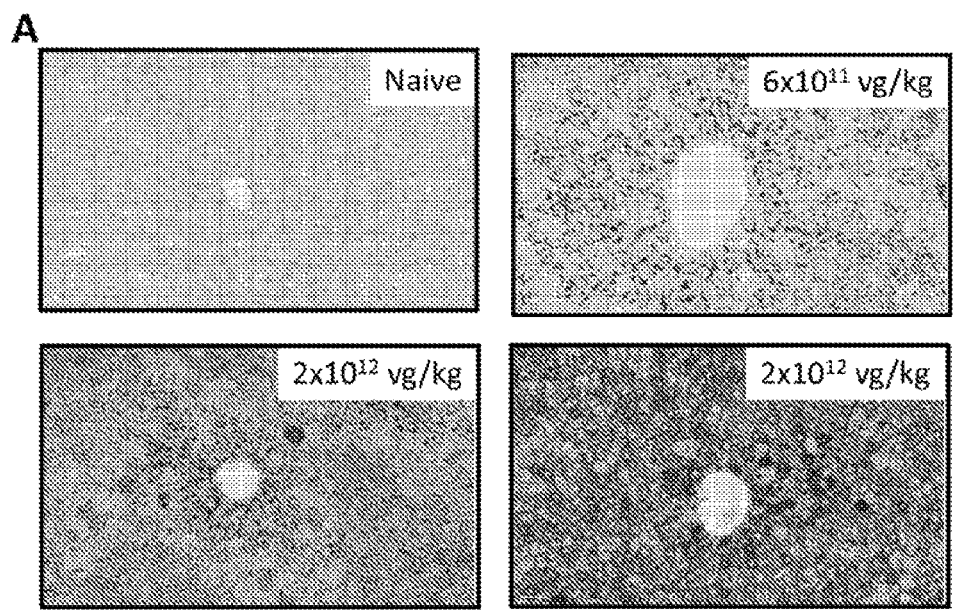
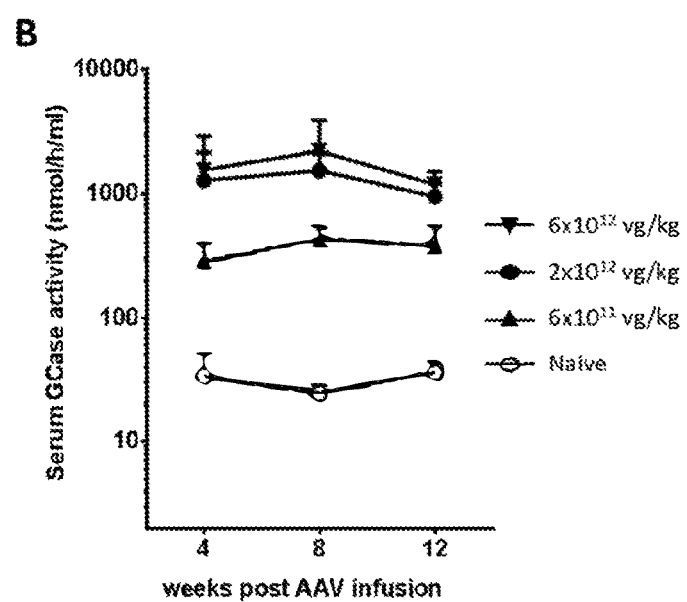

FIG. 9

SEQ ID NO: 1 - Codon-optimised GBA nucleotide sequence from FLF-PL28, without signal peptide portion GCCAGGCCCTGCATCCCTAAGAGCTTTGGCTACAGCTCTGTGGTGTGTGTGTGCAATGCCACCTAC
TGTGACAGCTTTGACCCCCCCACCTTTCCTGCCCTGGGCACCTTCAGCAGATATGAGAGCACCAGGT
CTGGGAGGAGGATGGAGCTGAGCATGGGCCCATCCAGGCTAATCACACTGGCACTGGCCTGCTG
CTGACCCTGCAGCCTGAGCAGAAGTTCCAGAAAGTAAAGGGCTTTGGAGGGGCCATGACTGATGCT
GCTGCTCTGAACATCCTGGCCCTGAGCCCCCCTGCCCAGAATCTGCTGCTGAAGAGCTACTTCTCTG
AGGAGGGCATTGGCTATAACATCATCAGGGTGCCCATGGCCAGCTGTGACTTCAGCATCAGGACCT
ACACCTATGCTGACACCCCTGATGATTTCCAGCTGCACAACTTCAGCCTGCCTGAGGAGGATACCAA
GCTGAAGATCCCACTGATCCACAGGGCTCTGCAGCTGGCCCAGAGGCCTGTGAGCCTGCTGGCCAG
CCCCTGGACCAGCCCCACTTGGCTGAAGACCAATGGGGCTGTGAATGGGAAGGGGAGCCTGAAGG
GACAGCCTGGAGACATCTACCACCAGACCTGGGCCAGATACTTTGTGAAGTTCCTGGATGCCTATGC
TGAGCACAAGCTGCAGTTCTGGGCTGTGACTGCTGAGAATGAGCCTTCTGCTGGGCTGCTGTCTGG
CTACCCCTTCCAATGCCTGGGCTTCACCCCTGAGCATCAGAGGGACTTCATTGCCAGGGACCTGGG
CCCTACCCTGGCCAACAGCACTCACCATAATGTTAGGCTGCTGATGCTGGATGACCAGAGGCTGCT
GCTGCCCCACTGGGCTAAGGTGGTGCTGACTGACCCTGAGGCTGCTAAATATGTGCATGGCATTGC
TGTGCATTGGTACCTGGACTTTCTGGCTCCTGCCAAGGCCACCCTGGGGGAGACCCACAGGCTGTT
CCCCAACACCATGCTGTTTGCCTCTGAGGCCTGTGTGGGCAGCAAGTTCTGGGAGCAGTCTGTGAG
GCTGGGCAGCTGGGATAGGGGGATGCAGTACAGCCACAGCATCATCACCAACCTGCTGTACCATGT
GGTGGGCTGGACTGACTGGAACCTGGCCCTGAACCCTGAGGGAGGACCTAACTGGGTCAGAAACTT
TGTGGACAGCCCCATCATTGTGGACATCACCAAGGACACCTTTTACAAGCAGCCCATGTTCTACCAC
CTGGGCCACTTCAGCAAGTTCATCCCTGAGGGCAGCCAGAGAGTGGGGCTGGTGGCCAGCCAGAA
GAATGACCTGGATGCTGTGGCTCTGATGCATCCTGATGGCTCTGCTGTGGTGGTGGTGCTGAACAG
GAGCTCTAAGGATGTGCCTCTGACCATCAAGGATCCTGCTGTGGGCTTCCTGGAGACCATCAGCCC
TGGCTACAGCATCCACACCTACCTGTGGAGGAGGCAGTGA SEQ ID NO: 2 - Codon-optimised GBA nucleotide sequence from FLF-PL21, without signal peptide portion GCCAGGCCCTGTATCCCTAAGAGCTTtGGCTACAGCTCAGTaGTtTGTGTCTGTAATGCCACATACTG
TGACTCCTTtGACCCCCCTACCTTCCCTGCCCTGGGAACCTTCAGCAGaTATGAGTCAACAAGaTCAG
GAAGGAGGATGGAGCTGTCAATGGGACCCATCCAGGCTAATCACACAGGCACAGGCCTGCTGCTGA
CCCTGCAGCCAGAACAGAAGTTCCAGAAaGTGAAGGGATTtGGAGGAGCCATGACAGATGCTGCTG
CTCTCAACATCCTGGCCCTGTCACCCCCTGCCCAGAATCTGCTGCTGAAGTCATACTTCTCTGAAGA
AGGAATtGGATATAACATCATCAGGGTGCCCATGGCCAGCTGTGACTTCTCCATCAGGACCTACACC
TATGCtGACACCCCTGATGATTTCCAGCTGCACAACTTCAGCCTCCCAGAGGAAGATACCAAGCTCAA
GATCCCtCTGATaCAtAGgGCaCTGCAGCTGGCCCAGAGGCCtGTGTCACTCCTGGCCAGCCCCTGGA
CATCACCCACTTGGCTCAAGACCAATGGAGCtGTGAATGGAAAGGGATCACTCAAGGGACAGCCtGG
AGACATCTACCACCAGACCTGGGCCAGaTACTTtGTGAAGTTCCTGGATGCCTATGCTGAGCACAAG
CTGCAGTTCTGGGCaGTGACAGCTGAAAATGAGCCTTCTGCTGGACTGCTGTCAGGATACCCCTTCC
AGTGTCTGGGCTTCACCCCTGAACATCAGAGGGACTTCATtGCCAGGGACCTGGGACCTACCCTtGC
CAACTCAACTCACCACAATGTCAGGCTGCTCATGCTGGATGACCAGAGGCTGCTGCTGCCCCACTGG
GCCAAGGTGGTGCTGACAGACCCAGAAGCtGCTAAaTATGTGCATGGCATtGCTGTGCATTGGTACC
TGGACTTCCTGGCTCCAGCCAAGGCCACCCTGGGAGAGACACACAGGCTGTTCCCCAACACCATGCT
CTTtGCCTCtGAGGCCTGTGTGGGCTCCAAGTTCTGGGAGCAGTCAGTGAGGCTGGGCTCCTGGGA
TAGGGGAATGCAGTACAGCCACAGCATCATCACAAACCTCCTGTACCATGTGGTgGGCTGGACtGAC
TGGAACCTGGCCCTGAACCCtGAAGGAGGACCCAAcTGGGTcagaAAtTTtGTgGACTCACCCATCATt
GTGGACATCACCAAGGACACATTCTACAAGCAGCCCATGTTCTACCACCTGGGCCACTTCAGCAAGT
TCATCCCTGAGGGCTCCCAGAGGGTGGGACTGGTGGCCTCACAGAAGAAtGACCTGGAtGCaGTGG

FIG. 9 CONT

CCCTGATGCATCCtGATGGCTCTGCTGTGGTGGTtGTGCTGAAtAGaTCCTCTAAGGATGTGCCTCT
GACCATCAAGGATCCTGCTGTGGGCTTCCTGGAGACAATCTCACCTGGCTACTCCATCCACACCTAC
CTGTGGAGGAGGCAGTGA

SEQ ID NO: 3 - Codon-optimised GBA nucleotide sequence from FLF-PL30, without signal peptide portion GCCAGGCCCTGCATCCCTAAGAGCTTTGGCTACAGCTCTGTGGTGTGTGTGCAATGCCACATAC
TGTGACTCCTTTGACCCCCCCACCTTTCCTGCCCTGGGCACaTTctccAGaTATGAGAGCACAAGATC
TGGGAGAAGGATGGAGCTGAGCATGGGGCCCATCCAGGCTAATCACACTGGCACAGGCCTGCTGCT
GACCCTGCAGCCTGAACAGAAGTTTCAGAAaGTGAAGGGATTTGGAGGGGCCATGACAGATGCTGC
TGCTCTGAATATCCTGGCCCTGTCACCCCCTGCCCAGAATCTGCTGCTGAAGAGCTACTTTTCAGAA
GAAGGAATTGGATATAATATCATCAGAGTGCCCATGGCCAGCTGTGACTTTTCCATCAGAACCTACA
CCTATGCAGACACCCCTGATGATTTTCAGCTGCACAATTTTAGCCTGCCTGAGGAAGATACCAAGCT
GAAGATACCCCTGATTCACAGGGCCCTGCAGCTGGCCCAGAGGCCTGTTTCACTGCTGGCCAGCCC
CTGGACATCACCCACCTGGCTGAAGACCAATGGAGCTGTGAATGGGAAGGGGTCACTGAAGGGACA
GCCTGGAGACATCTACCACCAGACCTGGGCCAGATACTTTGTGAAGTTTCTGGATGCCTATGCTGA
GCACAAGCTGCAGTTTGGGCAGTGACAGCTGAAAATGAGCCTTCAGCTGGGCTGCTGTCAGGATA
CCCCTTTCAGTGCCTGGGCTTTACCCCTGAACATCAGAGGGACTTTATTGCCAGGGACCTGGGCCCT
ACCCTGGCCAATAGCACCCAcCAtAATGTgAGgttgCTGATGCTGGATGACCAGAGGCTGCTGCTGCC
CCACTGGGCAAAGGTGGTGCTGACAGACCCTGAAGCAGCTAAaTATGTTCATGGCATTGCTGTGCA
TTGGTACCTGGACTTTCTGGCTCCTGCCAAGGCCACCCTGGGGGAGACACACAGGCTGTTTCCCAA
TACCATGCTGTTTGCCTCtGAGGCCTGTGTGGGCTCCAAGTTTTGGGAGCAGTCTGTGAGGCTGGG
CTCCTGGGATAGAGGGATGCAGTACAGCCACAGCATCATCACCAATCTGCTGTACCATGTGGTGGG
CTGGACTGACTGGAATCTGGCCCTGAATCCTGAAGGAGGACCtAAcTGGGTcAGgAATTTTGTGGAC
AGCCCCATCATTGTGGACATCACCAAGGACACCTTTTACAAGCAGCCCATGTTTTACCACCTGGGCC
ACTTTAGCAAGTTTATTCCTGAGGGCTCCCAGAGAGTGGGGCTGGTTGCCAGCCAGAAGAATGACC
TGGATGCAGTGGCACTGATGCATCCTGATGGCTCAGCTGTTGTGGTGGTGCTGAATAGATCCAGCA
AGGATGTGCCTCTGACCATCAAGGATCCTGCTGTGGGCTTTCTGGAGACAATCTCACCTGGCTACTC
CATTCACACCTACCTGTGGAGAAGGCAGTGA SEQ ID NO: 4 - Codon-optimised GBA nucleotide sequence from FLF-PL36, without signal peptide portion GCCAGGCCTTGCATCCCAAAGTCTTTCGGCTACAGCTCCGTGGTGTGCGTGTGCAACGCCACCTATT
GTGACTCCTTCGATCCCCCTACCTTTCCCGCCCTGGGCACATTTTCTAGATACGAGTCTACACGCAG
CGGCCGGAGAATGGAGCTGAGCATGGGCCCTATCCAGGCCAATCACACAGGAACAGGCCTGCTGCT
GACCCTGCAGCCAGAGCAGAAGTTCCAGAAGGTGAAGGGCTTTGGCGGAGCCATGACAGATGCAGC
CGCCCTGAACATCCTGGCCCTGTCCCCACCCGCCCAGAATCTGCTGCTGAAGTCCTACTTCTCTGAG
GAGGGCATCGGCTATAACATCATCCGGGTGCCCATGGCCAGCTGCGACTTTTCCATCAGAACCTACA
CATATGCCGATACCCCTGACGATTTCCAGCTGCACAATTTTTCCCTGCCAGAGGAGGATACAAAGCT
GAAGATCCCCCTGATTCACCGGGCCCTGCAGCTGGCACAGCGGCCCGTGAGCCTGCTGGCCAGCCC
CTGGACCTCCCCTACATGGCTGAAGACCAACGGCGCCGTGAATGGCAAGGGCTCTCTGAAGGGACA
GCCTGGCGACATCTACCACCAGACATGGGCCAGATATTTCGTGAAGTTTCTGGATGCCTACGCCGA
GCACAAGCTGCAGTTCTGGGCCGTGACAGCAGAGAATGAGCCTTCTGCCGGCCTGCTGAGCGGCTA
TCCCTTCCAGTGCCTGGGCTTTACACCTGAGCACCAGCGGGACTTTATCGCCAGAGATCTGGGCCC
AACCCTGGCCAACTCCACACACCACAATGTGAGGCTGCTGATGCTGGACGATCAGCGCCTGCTGCT
GCCTCACTGGGCCAAGGTGGTGCTGACCGACCCAGAGGCCGCCAAGTACGTGCACGGCATCGCCGT
GCACTGGTATCTGGATTTCCTGGCACCTGCAAAGGCCACCCTGGGAGAGACACCGGCTGTTCCC
TAACACCATGCTGTTTGCCAGCGAGGCCTGCGTGGGCTCCAAGTTTTGGGAGCAGTCCGTGAGGCT
GGGATCTTGGGACAGAGGCATGCAGTACTCCCACTCTATCATCACCAATCTGCTGTATCACGTGGTG
GGCTGGACAGACTGGAACCTGGCCCTGAATCCAGAGGGCGGCCCCAACTGGGTGAGAAATTTCGTG
GATAGCCCCATCATCGTGGACATCACCAAGGATACATTCTACAAGCAGCCAATGTTTTATCACCTGG
GCCACTTCTCTAAGTTTATCCCTGAGGGCAGCCAGAGGGTGGGCCTGGTGGCCAGCCAGAAGAACG

FIG. 9 CONT

ACCTGGATGCCGTGGCCCTGATGCACCCTGATGGCTCCGCCGTGGTGGTGGTGCTGAATCGCTCTA
GCAAGGACGTGCCTCTGACCATCAAGGATCCAGCCGTGGGATTTCTGGAGACTATTTCACCTGGCT
ATTCAATTCATACCTACCTGTGGAGGAGGCAGTGA

SEQ ID NO: 5 - Codon-optimised GBA nucleotide sequence from FLF-PL28, with signal peptide portion ATGGAGTTTTCAAGTCCTTCCAGAGAGGAATGTCCCAAGCCTTTGAGTAGGGTAAGCATCATGGCT
GGCAGCCTCACAGGATTGCTTCTACTTCAGGCAGTGTCGTGGGCATCAGGTGCCAGGCCCTGCATC
CCTAAGAGCTTTGGCTACAGCTCTGTGGTGTGTGTGCAATGCCACCTACTGTGACAGCTTTGAC
CCCCCCACCTTTCCTGCCCTGGGCACCTTCAGCAGaTATGAGAGCACCAGGTCTGGGAGGAGGATG
GAGCTGAGCATGGGGCCCATCCAGGCTAATCACACTGGCACTGGCCTGCTGCTGACCCTGCAGCCT
GAGCAGAAGTTCCAGAAaGTaAAGGGCTTTGGAGGGGCCATGACTGATGCTGCTGCTCTGAACATC
CTGGCCCTGAGCCCCCTGCCCAGAATCTGCTGCTGAAGAGCTACTTCTCTGAGGAGGGCATTGGC
TATAACATCATCAGGGTGCCCATGGCCAGCTGTGACTTCAGCATCAGGACCTACACCTATGCTGACA
CCCCTGATGATTTCCAGCTGCACAACTTCAGCCTGCCTGAGGAGGATACCAAGCTGAAGATCCCaCT
GATCCACAGGGCtCTGCAGCTGGCCCAGAGGCCTGTGAGCCTGCTGGCCAGCCCTGGACCAGCCC
CACTTGGCTGAAGACCAATGGGCTGTGAATGGGAAGGGGAGCCTGAAGGGACAGCCTGGAGACA
TCTACCACCAGACCTGGGCCAGATACTTTGTGAAGTTCCTGGATGCCTATGCTGAGCACAAGCTGCA
GTTCTGGGCTGTGACTGCTGAGAATGAGCCTTCTGCTGGGCTGCTGTCTGGCTACCCCTTCCAaTG
CCTGGGCTTCACCCCTGAGCATCAGAGGGACTTCATTGCCAGGGACCTGGGCCCTACCCTGGCCAA
CAGCACTCACCAtAATGTtAGGCTGCTGATGCTGGATGACCAGAGGCTGCTGCTGCCCCACTGGGCT
AAGGTGGTGCTGACTGACCCTGAGGCTGCTAAaTATGTGCATGGCATTGCTGTGCATTGGTACCTG
GACTTTCTGGCTCCTGCCAAGGCCACCCTGGGGGAGACCCACAGGCTGTTCCCCAACACCATGCTG
TTTGCCTCTGAGGCCTGTGTGGGCAGCAAGTTCTGGGAGCAGTCTGTGAGGCTGGGCAGCTGGGA
TAGGGGGATGCAGTACAGCCACAGCATCATCACCAACCTGCTGTACCATGTGGTGGGCTGGACTGA
CTGGAACCTGGCCCTGAACCCTGAGGGAGGACCtAaCTGGGTcAGaAACTTTGTGGACAGCCCCATC
ATTGTGGACATCACCAAGGACACCTTTTACAAGCAGCCCATGTTCTACCACCTGGGCCACTTCAGCA
AGTTCATCCCTGAGGGCAGCCAGAGAGTGGGGCTGGTGGCCAGCCAGAAGAATGACCTGGATGCT
GTGGCTCTGATGCATCCTGATGGCTCTGCTGTGGTGGTGGTGCTGAACAGGAGCTCTAAGGATGTG
CCTCTGACCATCAAGGATCCTGCTGTGGGCTTCCTGGAGACCATCAGCCCTGGCTACAGCATCCACA
CCTACCTGTGGAGGAGGCAGTGA SEQ ID NO: 6 - Codon-optimised GBA nucleotide sequence from FLF-PL21, with signal peptide portion ATGGAGTTTTCAAGTCCTTCCAGAGAGGAATGTCCCAAGCCTTTGAGTAGGGTAAGCATCATGGCT
GGCAGCCTCACAGGATTGCTTCTACTTCAGGCAGTGTCGTGGGCATCAGGTGCCAGGCCCTGTATC
CCTAAGAGCTTtGGCTACAGCTCAGTaGTtTGTGTCTGTAATGCCACATACTGTGACTCCTTtGACCC
CCCTACCTTCCCTGCCCTGGGAACCTTCAGCAGaTATGAGTCAACAAGaTCAGGAAGGAGGATGGAG
CTGTCAATGGGACCCATCCAGGCTAATCACACAGGCACAGGCCTGCTGCTGACCCTGCAGCCAGAAC
AGAAGTTCCAGAAaGTGAAGGGATTtGGAGGAGCCATGACAGATGCTGCTGCTCTCAACATCCTGGC
CCTGTCACCCCTGCCCAGAATCTGCTGCTGAAGTCATACTTCTCTGAAGAAGGAATtGGATATAAC
ATCATCAGGGTGCCCATGGCCAGCTGTGACTTCTCCATCAGGACCTACACCTATGCtGACACCCCTG
ATGATTTCCAGCTGCACAACTTCAGCCTCCCAGAGGAAGATACCAAGCTCAAGATCCCtCtGATaCAt
AGgGCaCTGCAGCTGGCCCAGAGGCCtGTGTCACTCCTGGCCAGCCCCTGGACATCACCCACTTGGC
TCAAGACCAATGGAGCtGTGAATGGAAAGGGATCACTCAAGGGACAGCCtGGAGACATCTACCACCA
GACCTGGGCCAGaTACTTtGTGAAGTTCCTGGATGCCTATGCTGAGCACAAGCTGCAGTTCTGGGCa
GTGACAGCTGAAAATGAGCCTTCTGCTGGACTGCTGTCAGGATACCCCTTCCAGTGTCTGGGCTTC
ACCCCTGAACATCAGAGGGACTTCATtGCCAGGGACCTGGGACCTACCCTtGCCAACTCAACTCACCA
CAATGTCAGGCTGCTCATGCTGGATGACCAGAGGCTGCTGCTGCCCCACTGGGCCAAGGTGGTGCT
GACAGACCCAGAAGCtGCTAAaTATGTGCATGGCATtGCTGTGCATTGGTACCTGGACTTCCTGGCT
CCAGCCAAGGCCACCCTGGGAGAGACACACAGGCTGTTCCCCAACACCATGCTCTTtGCCTCtGAGG
CCTGTGTGGGCTCCAAGTTCTGGGAGCAGTCAGTGAGGCTGGGCTCCTGGGATAGGGGAATGCAG

FIG. 9 CONT

TACAGCCACAGCATCATCACAAACCTCCTGTACCATGTGGTgGGCTGGACtGACTGGAACCTGGCCC
TGAACCCtGAAGGAGGACCCAAcTGGGTcagaAAtTTtGTgGACTCACCCATCATtGTGGACATCACCA
AGGACACATTCTACAAGCAGCCCATGTTCTACCACCTGGGCCACTTCAGCAAGTTCATCCCTGAGGG
CTCCCAGAGGGTGGGACTGGTGGCCTCACAGAAGAAtGACCTGGAtGCaGTGGCCCTGATGCATCCt
GATGGCTCTGCTGTGGTGGTtGTGCTGAAtAGaTCCTCTAAGGATGTGCCTCTGACCATCAAGGATC
CTGCTGTGGGCTTCCTGGAGACAATCTCACCTGGCTACTCCATCCACACCTACCTGTGGAGGAGGC
AGTGA SEQ ID NO: 7 - Codon-optimised GBA nucleotide sequence from FLF-PL30, with signal peptide portion ATGGAGTTTTCAAGTCCTTCCAGAGAGGAATGTCCCAAGCCTTTGAGTAGGGTAAGCATCATGGCT
GGCAGCCTCACAGGATTGCTTCTACTTCAGGCAGTGTCGTGGGCATCAGGTGCCAGGCCCTGCATC
CCTAAGAGCTTTGGCTACAGCTCTGTGGTGTGTGTGCAATGCCACATACTGTGACTCCTTTGACC
CCCCCACCTTTCCTGCCCTGGGCACaTTctccAGaTATGAGAGCACAAGATCTGGGAGAAGGATGGA
GCTGAGCATGGGGCCCATCCAGGCTAATCACACTGGCACAGGCCTGCTGCTGACCCTGCAGCCTGA
ACAGAAGTTTCAGAAaGTGAAGGGATTTGGAGGGGCCATGACAGATGCTGCTGCTCTGAATATCCT
GGCCCTGTCACCCCTGCCCAGAATCTGCTGCTGAAGAGCTACTTTTCAGAAGAAGGAATTGGATAT
AATATCATCAGAGTGCCCATGGCCAGCTGTGACTTTTCCATCAGAACCTACACCTATGCAGACACCC
CTGATGATTTTCAGCTGCACAATTTTAGCCTGCCTGAGGAAGATACCAAGCTGAAGATACCCCTGAT
TCACAGGGCCCTGCAGCTGGCCCAGAGGCCTGTTTCACTGCTGGCCAGCCCCTGGACATCACCCAC
CTGGCTGAAGACCAATGGAGCTGTGAATGGAAGGGGTCACTGAAGGGACAGCCTGGAGACATCTA
CCACCAGACCTGGGCCAGATACTTTGTGAAGTTTCTGGATGCCTATGCTGAGCACAAGCTGCAGTTT
TGGGCAGTGACAGCTGAAAATGAGCCTTCAGCTGGGCTGCTGTCAGGATACCCCTTTCAGTGCCTG
GCTTTACCCCTGAACATCAGAGGGACTTTATTGCCAGGGACCTGGGCCCTACCCTGGCCAATAGC
ACCCAcCAtAATGTgAGgttgCTGATGCTGGATGACCAGAGGCTGCTGCTGCCCCACTGGGCAAAGGT
GGTGCTGACAGACCCTGAAGCAGCTAAaTATGTTCATGGCATTGCTGTGCATTGGTACCTGGACTTT
CTGGCTCCTGCCAAGGCCACCCTGGGGGAGACACACAGGCTGTTTCCCAATACCATGCTGTTTGCC
TCtGAGGCCTGTGTGGGCTCCAAGTTTTGGGAGCAGTCTGTGAGGCTGGGCTCCTGGGATAGAGG
GATGCAGTACAGCCACAGCATCATCACCAATCTGCTGTACCATGTGGTGGGCTGGACTGACTGGAA
TCTGGCCCTGAATCCTGAAGGAGGACCtAAcTGGGTcAGgAATTTTGTGGACAGCCCCATCATTGTG
GACATCACCAAGGACACCTTTTACAAGCAGCCCATGTTTTACCACCTGGGCCACTTTAGCAAGTTTA
TTCCTGAGGGCTCCCAGAGAGTGGGGCTGGTTGCCAGCCAGAAGAATGACCTGGATGCAGTGGCAC
TGATGCATCCTGATGGCTCAGCTGTTGTGGTGGTGCTGAATAGATCCAGCAAGGATGTGCCTCTGA
CCATCAAGGATCCTGCTGTGGGCTTTCTGGAGACAATCTCACCTGGCTACTCCATTCACACCTACCT
GTGGAGAAGGCAGTGA SEQ ID NO: 8 - Codon-optimised GBA nucleotide sequence from FLF-PL36, with signal peptide portion ATGGAGTTTTCAAGTCCTTCCAGAGAGGAATGTCCCAAGCCTTTGAGTAGGGTAAGCATCATGGCT
GGCAGCCTCACAGGATTGCTTCTACTTCAGGCAGTGTCGTGGGCATCAGGTGCCAGGCCTTGCATC
CCAAAGTCTTTCGGCTACAGCTCCGTGGTGTGCGTGTGCAACGCCACCTATTGTGACTCCTTCGATC
CCCCTACCTTTCCCGCCCTGGGCACATTTTCTAGATACGAGTCTACACGCAGCGGCCGGAGAATGGA
GCTGAGCATGGGCCCTATCCAGGCCAATCACACAGGAACAGGCCTGCTGCTGACCCTGCAGCCAGA
GCAGAAGTTCCAGAAGGTGAAGGGCTTTGGCGGAGCCATGACAGATGCAGCCGCCCTGAACATCCT
GGCCCTGTCCCCACCCGCCCAGAATCTGCTGCTGAAGTCCTACTTCTCTGAGGAGGGCATCGGCTA
TAACATCATCCGGGTGCCCATGGCCAGCTGCGACTTTTCCATCAGAACCTACACATATGCCGATACC
CCTGACGATTTCCAGCTGCACAATTTTCCCTGCCAGAGGAGGATACAAAGCTGAAGATCCCCCTGA
TTCACCGGGCCCTGCAGCTGGCACAGCGGCCCGTGAGCCTGCTGGCCAGCCCCTGGACCTCCCCTA
CATGGCTGAAGACCAACGGCGCCGTGAATGGCAAGGGCTCTCTGAAGGGACAGCCTGGCGACATCT
ACCACCAGACATGGGCCAGATATTTCGTGAAGTTTCTGGATGCCTACGCCGAGCACAAGCTGCAGTT
CTGGGCCGTGACAGCAGAGAATGAGCCTTCTGCCGGCCTGCTGAGCGGCTATCCCTTCCAGTGCCT
GGGCTTTACACCTGAGCACCAGCGGGACTTTATCGCCAGAGATCTGGGCCCAACCCTGGCCAACTC

FIG. 9 CONT

```
CACACACCACAATGTGAGGCTGCTGATGCTGGACGATCAGCGCCTGCTGCTGCCTCACTGGGCCAA
GGTGGTGCTGACCGACCCAGAGGCCGCCAAGTACGTGCACGGCATCGCCGTGCACTGGTATCTGGA
TTTCCTGGCACCTGCAAAGGCCACCCTGGGAGAGACACACCGGCTGTTCCCTAACACCATGCTGTTT
GCCAGCGAGGCCTGCGTGGGCTCCAAGTTTTGGGAGCAGTCCGTGAGGCTGGGATCTTGGGACAG
AGGCATGCAGTACTCCCACTCTATCATCACCAATCTGCTGTATCACGTGGTGGGCTGGACAGACTGG
AACCTGGCCCTGAATCCAGAGGGCGGCCCCAACTGGGTGAGAAATTTCGTGGATAGCCCCATCATC
GTGGACATCACCAAGGATACATTCTACAAGCAGCCAATGTTTTATCACCTGGGCCACTTCTCTAAGT
TTATCCCTGAGGGCAGCCAGAGGGTGGGCCTGGTGGCCAGCCAGAAGAACGACCTGGATGCCGTG
GCCCTGATGCACCCTGATGGCTCCGCCGTGGTGGTGGTGCTGAATCGCTCTAGCAAGGACGTGCCT
CTGACCATCAAGGATCCAGCCGTGGGATTTCTGGAGACTATTTCACCTGGCTATTCAATTCATACCT
ACCTGTGGAGGAGGCAGTGA
```

SEQ ID NO: 9 - Wild type human GBA nucleotide sequence with signal peptide (from GenBank NM_000157.3)

```
ATGGAGTTTTCAAGTCCTTCCAGAGAGGAATGTCCCAAGCCTTTGAGTAGGGTAAGCATCATGGCT
GGCAGCCTCACAGGATTGCTTCTACTTCAGGCAGTGTCGTGGGCATCAGGTGCCCGCCCCTGCATC
CCTAAAAGCTTCGGCTACAGCTCGGTGGTGTGTGTCTGCAATGCCACATACTGTGACTCCTTTGACC
CCCCGACCTTTCCTGCCCTTGGTACCTTCAGCCGCTATGAGAGTACACGCAGTGGGCGACGGATGG
AGCTGAGTATGGGGCCCATCCAGGCTAATCACACGGGCACAGGCCTGCTACTGACCCTGCAGCCAG
AACAGAAGTTCCAGAAAGTGAAGGGATTTGGAGGGGCCATGACAGATGCTGCTGCTCTCAACATCC
TTGCCCTGTCACCCCTGCCCAAAATTTGCTACTTAAATCGTACTTCTCTGAAGAAGGAATCGGATA
TAACATCATCCGGGTACCCATGGCCAGCTGTGACTTCTCCATCCGCACCTACACCTATGCAGACACC
CCTGATGATTTCCAGTTGCACAACTTCAGCCTCCCAGAGGAAGATACCAAGCTCAAGATACCCCTGA
TTCACCGAGCCCTGCAGTTGGCCCAGCGTCCCGTTTCACTCCTTGCCAGCCCCTGGACATCACCCAC
TTGGCTCAAGACCAATGGAGCGGTGAATGGGAAGGGGTCACTCAAGGGACAGCCCGGAGACATCTA
CCACCAGACCTGGGCCAGATACTTTGTGAAGTTCCTGGATGCCTATGCTGAGCACAAGTTACAGTTC
TGGGCAGTGACAGCTGAAAATGAGCCTTCTGCTGGGCTGTTGAGTGGATACCCCTTCCAGTGCCTG
GGCTTCACCCCTGAACATCAGCGAGACTTCATTGCCCGTGACCTAGGTCCTACCCTCGCCAACAGTA
CTCACCACAATGTCCGCCTACTCATGCTGGATGACCAACGCTTGCTGCTGCCCCACTGGGCAAAGGT
GGTACTGACAGACCCAGAAGCAGCTAAATATGTTCATGGCATTGCTGTACATTGGTACCTGGACTTT
CTGGCTCCAGCCAAAGCCACCCTAGGGGAGACACACCGCCTGTTCCCAACACCATGCTCTTTGCCT
CAGAGGCCTGTGTGGGCTCCAAGTTCTGGGAGCAGAGTGTGCGGCTAGGCTCCTGGGATCGAGGG
ATGCAGTACAGCCACAGCATCATCACGAACCTCCTGTACCATGTGGTCGGCTGGACCGACTGGAACC
TTGCCCTGAACCCCGAAGGAGGACCCAATTGGGTGCGTAACTTTGTCGACAGTCCCATCATTGTAGA
CATCACCAAGGACACGTTTTACAAACAGCCCATGTTCTACCACCTTGGCCACTTCAGCAAGTTCATTC
CTGAGGGCTCCCAGAGAGTGGGGCTGGTTGCCAGTCAGAAGAACGACCTGGACGCAGTGGCACTG
ATGCATCCCGATGGCTCTGCTGTTGTGGTCGTGCTAAACCGCTCCTCTAAGGATGTGCCTCTTACCA
TCAAGGATCCTGCTGTGGGCTTCCTGGAGACAATCTCACCTGGCTACTCCATTCACACCTACCTGTG
GCGTCGCCAGTGA
```

SEQ ID NO: 10 - LSP-S transcription regulatory element

```
CCCTAAAATGGGCAAACATTGCAAGCAGCAAACAGCAAACACACAGCCCTCCCTGCCTGCTGACCTT
GGAGCTGGGGCAGAGGTCAGACACCTCTCTGGGCCATGCCACCTCCAACTGGACACAGGACGCTG
TGGTTTCTGAGCCAGGGGGCGACTCAGATCCCAGCCAGTGGACTTAGCCCCTGTTTGCTCCTCCGA
TAACTGGGGTGACCTTGGTTAATATTCACCAGCAGCCTCCCCCGTTGCCCCTCTGGATCCACTGCTT
AAATACGGACGAGGACAGGGCCCTGTCTCCTCAGCTTCAGGCACCACCACTGACCTGGGACAGTGA
AT
```

SEQ ID NO: 11 - HCR enhancer portion of LSP-S

FIG. 9 CONT

CCCTAAAATGGGCAAACATTGCAAGCAGCAAACAGCAAACACACAGCCCTCCCTGCCTGCTGACCTT
GGAGCTGGGGCAGAGGTCAGACACCTCTCTGGGCCCATGCCACCTCCAAC

SEQ ID NO: 12 - A1AT promoter portion of LSP-S

GGGCGACTCAGATCCCAGCCAGTGGACTTAGCCCTGTTTGCTCCTCCGATAACTGGGGTGACCTT
GGTTAATATTCACCAGCAGCCTCCCCCGTTGCCCCTCTGGATCCACTGCTTAAATACGGACGAGGAC
AGGGCCCTGTCTCCTCAGCTTCAGGCACCACCACTGACCTGGGACAGTGAAT

SEQ ID NO: 13 - CAG promoter

GACATTGATTATTGACTAGTTATTAATAGTAATCAATTACGGGGTCATTAGTTCATAGCCCATATATG
GAGTTCCGCGTTACATAACTTACGGTAAATGGCCCGCCTGGCTGACCGCCCAACGACCCCCGCCCAT
TGACGTCAATAATGACGTATGTTCCCATAGTAACGCCAATAGGGACTTTCCATTGACGTCAATGGGT
GGAGTATTTACGGTAAACTGCCCACTTGGCAGTACATCAAGTGTATCATATGCCAAGTACGCCCCCT
ATTGACGTCAATGACGGTAAATGGCCCGCCTGGCATTATGCCCAGTACATGACCTTATGGGACTTTC
CTACTTGGCAGTACATCTACGTATTAGTCATCGCTATTACCATGGTCGAGGTGAGCCCCACGTTCTG
CTTCACTCTCCCCATCTCCCCCCCCTCCCCACCCCCAATTTTGTATTTATTTATTTTTTAATTATTTTG
TGCAGCGATGGGGGCGGGGGGGGGGGGGGGCGCGCGCCAGGCGGGGCGGGGCGGGCGAGG
GGCGGGGCGGGGCGAGGCGGAGAGGTGCGGCGGCAGCCAATCAGAGCGGCGCGCTCCGAAAGTT
TCCTTTTATGGCGAGGCGGCGGCGGCGGCGGCCCTATAAAAAGCGAAGCGCGCGGCGGGCG

SEQ ID NO: 14 - LSP-L transcription regulatory element

AGGCTCAGAGGCACACAGGAGTTTCTGGGCTCACCCTGCCCCCTTCCAACCCCTCAGTTCCCATCCT
CCAGCAGCTGTTTGTGTGCTGCCTCTGAAGTCCACACTGAACAAACTTCAGCCTACTCATGTCCCTA
AAATGGGCAAACATTGCAAGCAGCAAACAGCAAACACACAGCCCTCCCTGCCTGCTGACCTTGGAGC
TGGGGCAGAGGTCAGAGACCTCTCTGGGCCCATGCCACCTCCAACATCCACTCGACCCCTTGGAATT
TCGGTGGAGAGGAGCAGAGGTTGTCCTGGCGTGGTTTAGGTAGTGTGAGAGGGGTACCCGGGGAT
CTTGCTACCAGTGGAACAGCCACTAAGGATTCTGCAGTGAGAGCAGAGGGCCAGCTAAGTGGTACT
CTCCCAGAGACTGTCTGACTCACGCCACCCCCTCCACCTTGGACACAGGACGCTGTGGTTTCTGAGC
CAGGTACAATGACTCCTTTCGGTAAGTGCAGTGGAAGCTGTACACTGCCCAGGCAAAGCGTCCGGG
CAGCGTAGGCGGGCGACTCAGATCCCAGCCAGTGGACTTAGCCCCTGTTTGCTCCTCCGATAACTG
GGGTGACCTTGGTTAATATTCACCAGCAGCCTCCCCCGTTGCCCCTCTGGATCCACTGCTTAAATAC
GGACGAGGACAGGGCCCTGTCTCCTCAGCTTCAGGCACCACCACTGACCTGGGACAGTGAATGATC
CCCCTGATCTGCGGCC

SEQ ID NO: 15 - A1AT promoter portion of LSP-L

GGATCTTGCTACCAGTGGAACAGCCACTAAGGATTCTGCAGTGAGAGCAGAGGGCCAGCTAAGTGG
TACTCTCCCAGAGACTGTCTGACTCACGCCACCCCCTCCACCTTGGACACAGGACGCTGTGGTTTCT
GAGCCAGGTACAATGACTCCTTTCGGTAAGTGCAGTGGAAGCTGTACACTGCCCAGGCAAAGCGTC
CGGGCAGCGTAGGCGGGCGACTCAGATCCCAGCCAGTGGACTTAGCCCCTGTTTGCTCCTCCGATA
ACTGGGGTGACCTTGGTTAATATTCACCAGCAGCCTCCCCCGTTGCCCCTCTGGATCCACTGCTTAA
ATACGGACGAGGACAGGGCCCTGTCTCCTCAGCTTCAGGCACCACCACTGACCTGGGACAGTGAAT
GATCCCCCTGATCTGCGGCC

SEQ ID NO: 16 - HCR enhancer portion of LSP-L

AGGCTCAGAGGCACACAGGAGTTTCTGGGCTCACCCTGCCCCCTTCCAACCCCTCAGTTCCCATCCT
CCAGCAGCTGTTTGTGTGCTGCCTCTGAAGTCCACACTGAACAAACTTCAGCCTACTCATGTCCCTA
AAATGGGCAAACATTGCAAGCAGCAAACAGCAAACACACAGCCCTCCCTGCCTGCTGACCTTGGAGC
TGGGGCAGAGGTCAGAGACCTCTCTGGGCCCATGCCACCTCCAACATCCACTCGACCCCTTGGAATT
TCGGTGGAGAGGAGCAGAGGTTGTCCTGGCGTGGTTTAGGTAGTGTGAGAGGG

FIG. 9 CONT

SEQ ID NO: 17 - Wild type GBA nucleotide sequence corresponding to signal peptide ATGGAGTTTTCAAGTCCTTCCAGAGAGGAATGTCCCAAGCCTTTGAGTAGGGTAAGCATCATGGCT
GGCAGCCTCACAGGATTGCTTCTACTTCAGGCAGTGTCGTGGGCATCAGGT SEQ ID NO: 18 - Wild type GCase polypeptide sequence of signal peptide

MEFSSPSREECPKPLSRVSIMAGSLTGLLLLQAVSWASG

SEQ ID NO: 19 - Polypeptide sequence of liver-tropic capsid

MAADGYLPDWLEDNLSEGIREWWALKPGVPQPKANQQHQDNRRGLVLPGYKYLGPGNGLDKGEPVNEA
DAAALEHDKAYDQQLKAGDNPYLKYNHADAEFQERLQEDTSFGGNLGRAVFQAKKRILEPLGLVEEAAKT
APGKKRPVDQSPQEPDSSSGVGKSGKQPARKRLNFGQTGDSESVPDPQPLGEPPAAPTSLGSNTMASGGG
APMADNNEGADGVGNSSGNWHCDSQWLGDRVITTSTRTWALPTYNNHLYKQISSQSGASNDNHYFGYST
PWGYFDFNRFHCHFSPRDWQRLINNNWGFRPKKLSFKLFNIQVKEVTQNDGTTTIANNLTSTVQVFTDSE
YQLPYVLGSAHQGCLPPFPADVFMVPQYGYLTLNNGSQAVGRSSFYCLEYFPSQMLRTGNNFQFSYTFED
VPFHSSYAHSQSLDRLMNPLIDQYLYYLNRTQGTTSGTTNQSRLLFSQAGPQSMSLQARNWLPGPCYRQQ
RLSKTANDNNNSNFPWTAASKYHLNGRDSLVNPGPAMASHKDDEEKFFPMHGNLIFGKEGTTASNAELDN
VMITDEEEIRTTNPVATEQYGTVANNLQSSNTAPTTRTVNDQGALPGMVWQDRDVYLQGPIWAKIPHTD
GHFHPSPLMGGFGLKHPPPQIMIKNTPVPANPPTTFSPAKFASFITQYSTGQVSVEIEWELQKENSKRWNP
EIQYTSNYNKSVNVDFTVDTNGVYSEPRPIGTRYLTRNL

SEQ ID NO: 20 - Polypeptide sequence of liver-tropic capsid

MAADGYLPDWLEDNLSEGIREWWALKPGAPKPKANQQKQDDGRGLVLPGYKYLGPFNGLDKGEPVNAA
DAAALEHDKAYDQQLQAGDNPYLRYNHADAEFQERLQEDTSFGGNLGRAVFQAKKRVLEPLGLVEEGAK
TAPGKKRPVDQSPQEPDSSSGVGKSGKQPARKRLNFGQTGDSESVPDPQPLGEPPAAPTSLGSNTMASGG
GAPMADNNEGADGVGNSSGNWHCDSQWLGDRVITTSTRTWALPTYNNHLYKQISSQSGASNDNHYFGY
STPWGYFDFNRFHCHFSPRDWQRLINNNWGFRPKKLSFKLFNIQVKEVTQNDGTTTIANNLTSTVQVFTD
SEYQLPYVLGSAHQGCLPPFPADVFMVPQYGYLTLNNGSQAVGRSSFYCLEYFPSQMLRTGNNFQFSYTF
EDVPFHSSYAHSQSLDRLMNPLIDQYLYYLNRTQGTTSGTTNQSRLLFSQAGPQSMSLQARNWLPGPCYR
QQRLSKTANDNNNSNFPWTAASKYHLNGRDSLVNPGPAMASHKDDEEKFFPMHGNLIFGKEGTTASNAEL
DNVMITDEEEIRTTNPVATEQYGTVANNLQSSNTAPTTRTVNDQGALPGMVWQDRDVYLQGPIWAKIPHT
DGHFHPSPLMGGFGLKHPPPQIMIKNTPVPANPPTTFSPAKFASFITQYSTGQVSVEIEWELQKENSKRWN
PEIQYTSNYNKSVNVDFTVDTNGVYSEPRPIGTRYLTRNL

SEQ ID NO: 21 - Polypeptide sequence of CNS-tropic capsid

MAADGYLPDWLEDNLSEGIREWWALKPGAPQPKANQQHQDNARGLVLPGYKYLGPGNGLDKGEPVNAA
DAAALEHDKAYDQQLKAGDNPYLKYNHADAEFQERLKEDTSFGGNLGRAVFQAKKRLLEPLGLVEEAAKT
APGKKRPVEQSPQEPDSSAGIGKSGAQPAKKRLNFGQTGDTESVPDPQPIGEPPAAPSGVGSLTMASGGG
APVADNNEGADGVGSSSGNWHCDSQWLGDRVITTSTRTWALPTYNNHLYKQISNSTSGGSSNDNAYFGY
STPWGYFDFNRFHCHFSPRDWQRLINNNWGFRPKRLNFKLFNIQVKEVTDNNGVKTIANNLTSTVQVFTD
SDYQLPYVLGSAHEGCLPPFPADVFMIPQYGYLTLNDGSQAVGRSSFYCLEYFPSQMLRTGNNFQFSYEFE
NVPFHSSYAHSQSLDRLMNPLIDQYLYYLSKTINGSGQNQQTLKFSVAGPSNMAVQGRNYIPGPSYRQQRV
STTVTQNNNSEFAWPGASSWALNGRNSLMNPGPAMASHKEGEDRFFPLSGSLIFGKQGTGRDNVDADKV
MITNEEEIKTTNPVATESYGQVATNHQSAQAQAQTGWVQNQGILPGMVWQDRDVYLQGPIWAKIPHTDG
NFHPSPLMGGFGMKHPPPQILIKNTPVPADPPTAFNKDKLNSFITQYSTGQVSVEIEWELQKENSKRWNPEI
QYTSNYYKSNNVEFAVNTEGVYSEPRPIGTRYLTRNL

SEQ ID NO: 22 - Nucleotide sequence of SV40 intron

FIG. 9 CON'T

GTAAATATAAAATTTTTAAGTGTATAATGTGTTAAACTACTGATTCTAATTGTTTCTCTCTTTTAG

SEQ ID NO: 23 - Nucleotide sequence of bovine growth hormone poly A sequence

CTGTGCCTTCTAGTTGCCAGCCATCTGTTGTTTGCCCCTCCCCCGTGCCTTCCTTGACCCTGGAAGG
TGCCACTCCCACTGTCCTTTCCTAATAAAATGAGGAAATTGCATCGCATTGTCTGAGTAGGTGTCAT
TCTATTCTGGGGGGTGGGGTGGGGCAGGACAGCAAGGGGGAGGATTGGGAAGACAATAGCAGGCA
TGCTGGGGA

SEQ ID NO: 24 - Polypeptide sequence of liver-tropic capsid

MAADGYLPDWLEDNLSEGIREWWALQPGAPKPKANQQHQDNARGLVLPGYKYLGPGNGLDKGEPVNAA
DAAALEHDKAYDQQLKAGDNPYLKYNHADAEFQERLKEDTSFGGNLGRAVFQAKKRLLEPLGLVEEAAKT
APGKKRPVDQSPQEPDSSSGVGKSGKQPARKRLNFGQTGDSESVPDPQPLGEPPAAPTSLGSNTMASGGG
APMADNNEGADGVGNSSGNWHCDSQWLGDRVITTSTRTWALPTYNNHLYKQISSQSGASNDNHYFGYST
PWGYFDFNRFHCHFSPRDWQRLINNNWGFRPKKLSFKLFNIQVKEVTQNDGTTTIANNLTSTVQVFTDSE
YQLPYVLGSAHQGCLPPFPADVFMVPQYGYLTLNNGSQAVGRSSFYCLEYFPSQMLRTGNNFQFSYTFED
VPFHSSYAHSQSLDRLMNPLIDQYLYYLNRTQGTTSGTTNQSRLLFSQAGPQSMSLQARNWLPGPCYRQQ
RLSKTANDNNNSNFPWTAASKYHLNGRDSLVNPGPAMASHKDDEEKFFPMHGNLIFGKEGTTASNAELDN
VMITDEEEIRTTNPVATEQYGTVANNLQSSNTAPTTRTVNDQGALPGMVWQDRDVYLQGPIWAKIPHTD
GHFHPSPLMGGFGLKHPPPQIMIKNTPVPANPPTTFSPAKFASFITQYSTGQVSVEIEWELQKENSKRWNP
EIQYTSNYNKSVNVDFTVDTNGVYSEPRPIGTRYLTRPL

SEQ ID NO: 25 - Polypeptide sequence of wild type human GCase

MEFSSPSREECPKPLSRVSIMAGSLTGLLLLQAVSWASGARPCIPKSFGYSSVVCVCNATYCDSFDPPTFPAL
GTFSRYESTRSGRRMELSMGPIQANHTGTGLLLTLQPEQKFQKVKGFGGAMTDAAALNILALSPPAQNLLL
KSYFSEEGIGYNIIRVPMASCDFSIRTYTYADTPDDFQLHNFSLPEEDTKLKIPLIHRALQLAQRPVSLLASPW
TSPTWLKTNGAVNGKGSLKGQPGDIYHQTWARYFVKFLDAYAEHKLQFWAVTAENEPSAGLLSGYPFQC
LGFTPEHQRDFIARDLGPTLANSTHHNVRLLMLDDQRLLLPHWAKVVLTDPEAAKYVHGIAVHWYLDFLA
PAKATLGETHRLFPNTMLFASEACVGSKFWEQSVRLGSWDRGMQYSHSIITNLLYHVVGWTDWNLALNPE
GGPNWVRNFVDSPIIVDITKDTFYKQPMFYHLGHFSKFIPEGSQRVGLVASQKNDLDAVALMHPDGSAVVV
VLNRSSKDVPLTIKDPAVGFLETISPGYSIHTYLWRRQ

FIG. 11
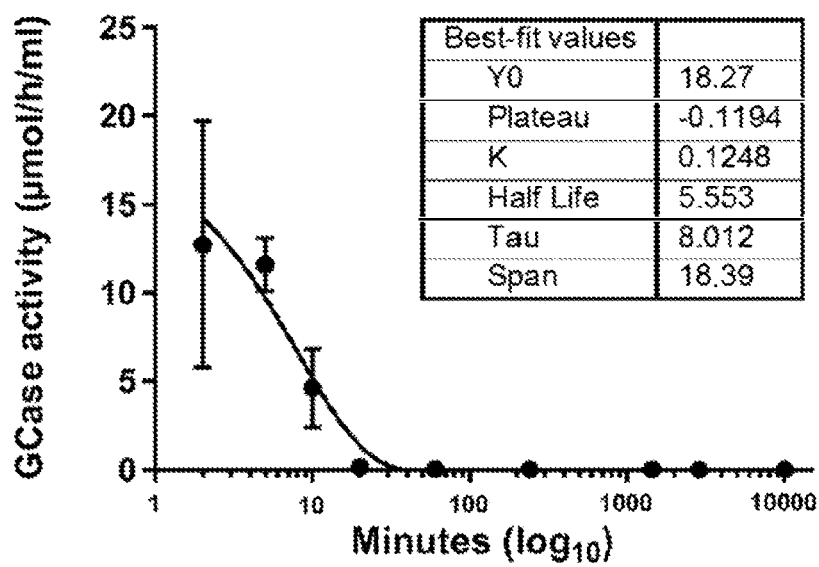
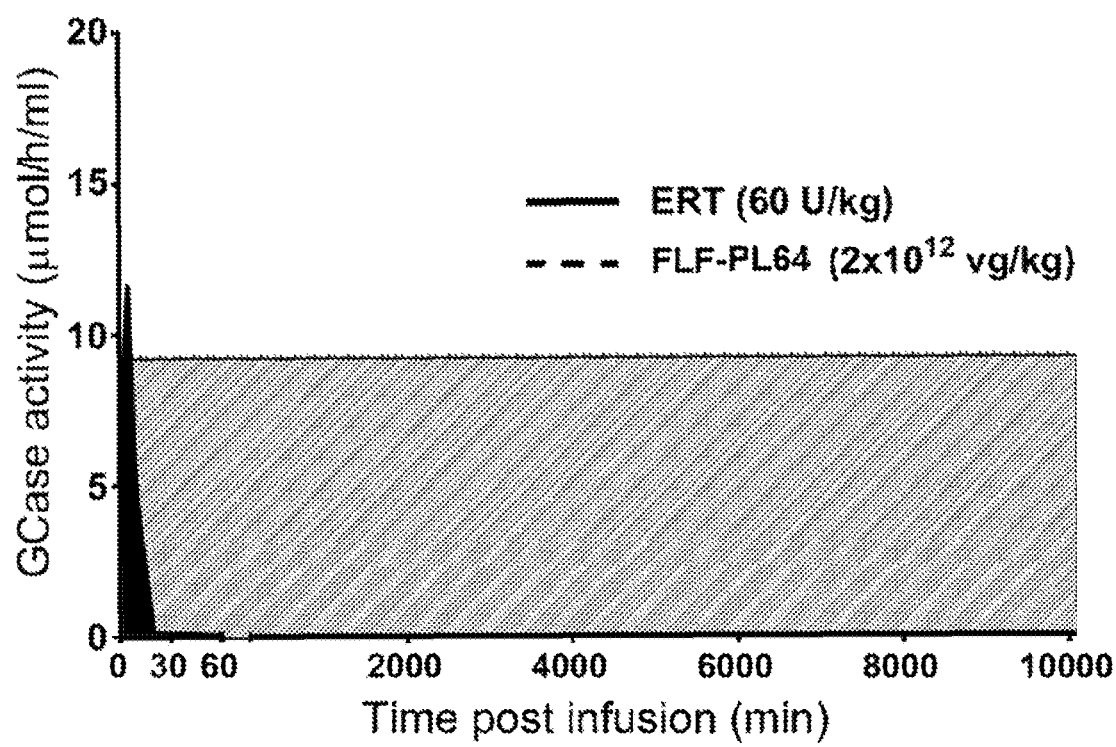

FIG. 15
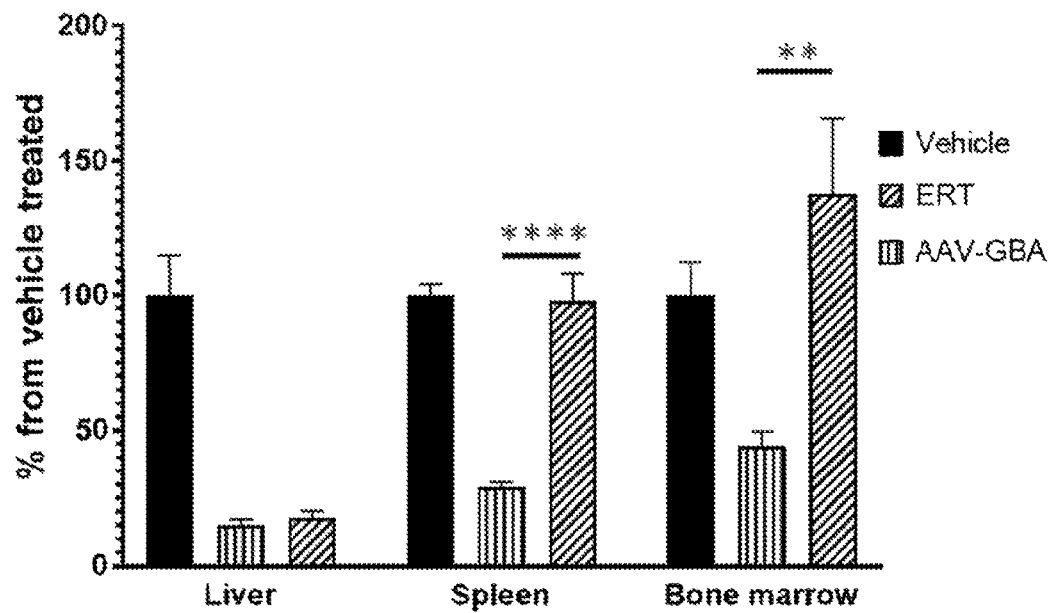
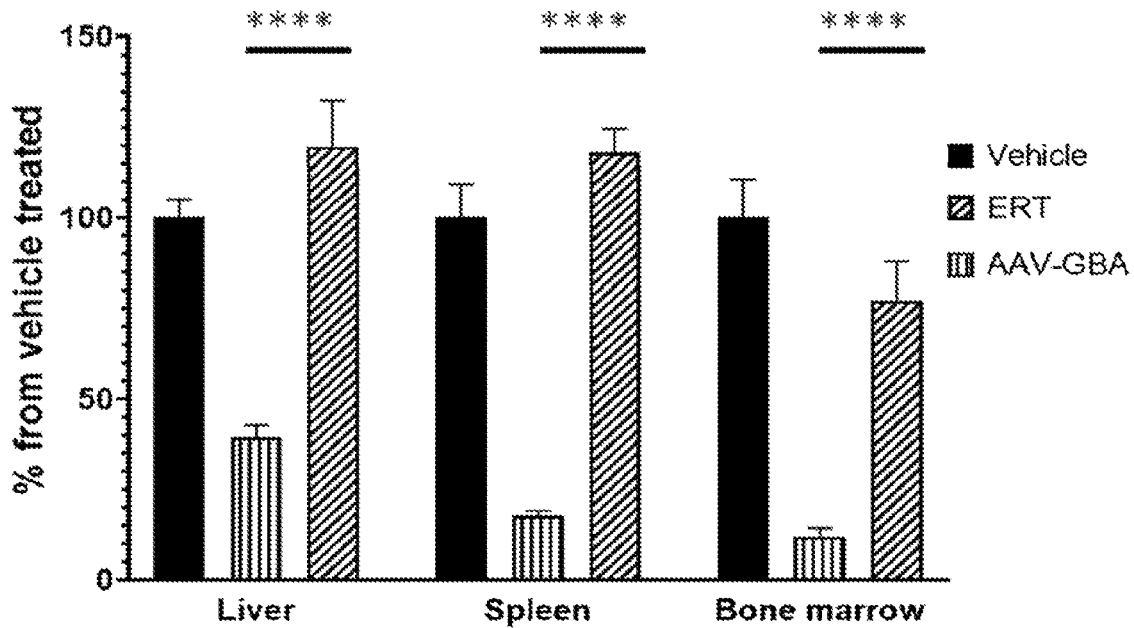

SEQUENCE LISTING

```
<160> NUMBER OF SEQ ID NOS: 25

<210> SEQ ID NO 1
<211> LENGTH: 1494
<212> TYPE: DNA
<213> ORGANISM: Artificial Sequence
```

```
<220> FEATURE:
<223> OTHER INFORMATION: Synthetic construct

<400> SEQUENCE: 1
gccaggccct gcatccctaa gagctttggc tacagctctg tggtgtgtgt gtgcaatgcc      60
acctactgtg acagctttga ccccccccacc tttcctgccc tgggcaccnt cagcagatat    120
gagagcacca ggtctgggag gaggatggag ctgagcatgg ggcccatcca ggctaatcac    180
actggcactg gcctgctgct gaccctgcag cctgagcaga agttccagaa agtaaagggc    240
tttggagggg ccatgactga tgctgctgct ctgaacatcc tggccctgag ccccctgcc     300
cagaatctgc tgctgaagag ctacttctct gaggagggca ttggctataa catcatcagg    360
gtgcccatgg ccagctgtga cttcagcatc aggacctaca cctatgctga caccctgat     420
gatttccagc tgcacaactt cagcctgcct gaggaggata ccaagctgaa gatcccactg    480
atccacaggg ctctgcagct ggcccagagg cctgtgagcc tgctggccag cccctggacc    540
agccccactt ggctgaagac caatgggct gtgaatggga aggggagcct gaagggacag     600
cctggagaca tctaccacca gacctgggcc agatactttg tgaagttcct ggatgcctat    660
gctgagcaca agctgcagtt ctgggctgtg actgctgaga atgagccttc tgctgggctg    720
ctgtctggct accccttcca atgcctgggc ttcacccctg agcatcagag ggacttcatt    780
gccagggacc tgggccctac cctggccaac agcactcacc ataatgttag gctgctgatg    840
ctggatgacc agaggctgct gctgcccac tgggctaagg tggtgctgac tgaccctgag     900
gctgctaaat atgtgcatgg cattgctgtg cattggtacc tggactttct ggctcctgcc    960
aaggccaccc tggggagac ccacaggctg ttccccaaca ccatgctgtt tgcctctgag    1020
gcctgtgtgg gcagcaagtt ctgggagcag tctgtgaggc tgggcagctg ggataggggg   1080
atgcagtaca gccacagcat catcaccaac ctgctgtacc atgtggtggg ctggactgac   1140
tggaacctgg ccctgaaccc tgagggagga cctaactggg tcagaaactt tgtggacagc   1200
cccatcattg tggacatcac caaggacacc ttttacaagc agcccatgtt ctaccacctg   1260
ggccacttca gcaagttcat ccctgagggc agccagagag tggggctggt ggccagccag   1320
aagaatgacc tggatgctgt ggctctgatg catcctgatg ctctgctgt ggtggtggtg    1380
ctgaacagga gctctaagga tgtgcctctg accatcaagg atcctgctgt gggcttcctg   1440
gagaccatca gccctggcta cagcatccac acctacctgt ggaggaggca gtga          1494

<210> SEQ ID NO 2
<211> LENGTH: 1494
<212> TYPE: DNA
<213> ORGANISM: Artificial Sequence
<220> FEATURE:
<223> OTHER INFORMATION: Synthetic construct

<400> SEQUENCE: 2
gccaggccct gtatccctaa gagctttggc tacagctcag tagtttgtgt ctgtaatgcc      60
acatactgtg actcctttga ccccccctacc ttccctgccc tgggaacctt cagcagatat    120
gagtcaacaa gatcaggaag gaggatggag ctgtcaatgg gacccatcca ggctaatcac    180
acaggcacag gcctgctgct gaccctgcag ccagaacaga agttccagaa agtgaaggga    240
tttggaggag ccatgacaga tgctgctgct ctcaacatcc tggccctgtc acccctgcc     300
cagaatctgc tgctgaagtc atacttctct gaagaaggaa ttggatataa catcatcagg    360
gtgcccatgg ccagctgtga cttctccatc aggacctaca cctatgctga caccctgat     420
```

```
gatttccagc tgcacaactt cagcctccca gaggaagata ccaagctcaa gatccctctg      480
atacataggg cactgcagct ggcccagagg cctgtgtcac tcctggccag cccctggaca      540
tcacccactt ggctcaagac caatggagct gtgaatggaa agggatcact caagggacag      600
cctggagaca tctaccacca gacctgggcc agatactttg tgaagttcct ggatgcctat      660
gctgagcaca agctgcagtt ctgggcagtg acagctgaaa atgagccttc tgctggactg      720
ctgtcaggat accccttcca gtgtctgggc ttcaccccetg aacatcagag ggacttcatt      780
gccagggacc tgggacctac ccttgccaac tcaactcacc acaatgtcag gctgctcatg      840
ctggatgacc agaggctgct gctgccccac tgggccaagg tggtgctgac agacccagaa      900
gctgctaaat atgtgcatgg cattgctgtg cattggtacc tggacttcct ggctccagcc      960
aaggccaccc tggagagaca acacaggctg ttccccaaca ccatgctctt tgcctctgag     1020
gcctgtgtgg gctccaagtt ctgggagcag tcagtgaggc tgggctcctg ggataggga     1080 atgcagtaca gccacagcat catcacaaac ctcctgtacc atgtggtggg ctggactgac     1140
tggaacctgg ccctgaaccc tgaaggagga cccaactggg tcagaaattt tgtggactca     1200
cccatcattg tggacatcac caaggacaca ttctacaagc agcccatgtt ctaccacctg     1260
ggccacttca gcaagttcat ccctgagggc tcccagaggg tgggactggt ggcctcacag     1320
aagaatgacc tggatgcagt ggccctgatg catcctgatg ctctgctgt ggtggttgtg     1380 ctgaatagat cctctaagga tgtgcctctg accatcaagg atcctgctgt gggcttcctg     1440
gagacaatct cacctggcta ctccatccac acctacctgt ggaggaggca gtga          1494

<210> SEQ ID NO 3
<211> LENGTH: 1494
<212> TYPE: DNA
<213> ORGANISM: Artificial Sequence
<220> FEATURE:
<223> OTHER INFORMATION: Synthetic construct

<400> SEQUENCE: 3
gccaggccct gcatccctaa gagctttggc tacagctctg tggtgtgtgt gtgcaatgcc       60
acatactgtg actcctttga ccccccccacc tttcctgccc tgggcacatt ctccagatat      120
gagagcacaa gatctgggag aaggatggag ctgagcatgg ggcccatcca ggctaatcac      180
actggcacag gctgctgct gaccctgcag cctgaacaga agtttcagaa agtgaaggga      240
tttggagggg ccatgacaga tgctgctgct ctgaatatcc tggccctgtc acccccctgcc      300 cagaatctgc tgctgaagag ctacttttca gaagaaggaa ttggatataa tatcatcaga      360
gtgcccatgg ccagctgtga cttttccatc agaacctaca cctatgcaga caccctgat      420 gattttcagc tgcacaattt tagcctgcct gaggaagata ccaagctgaa gatacccctg      480
attcacaggg ccctgcagct ggcccagagg cctgtttcac tgctggccag cccctggaca      540
tcacccacct ggctgaagac caatggagct gtgaatggga agggtcact gaagggacag      600 cctggagaca tctaccacca gacctgggcc agatactttg tgaagtttct ggatgcctat      660
gctgagcaca agctgcagtt ttgggcagtg acagctgaaa atgagccttc agctgggctg      720
ctgtcaggat accccttca gtgcctgggc tttaccccctg aacatcagag ggactttatt      780
gccagggacc tgggccctac cctggccaat agcacccacc ataatgtgag gttgctgatg      840
ctggatgacc agaggctgct gctgccccac tgggcaaagg tggtgctgac agaccctgaa      900
gcagctaaat atgttcatgg cattgctgtg cattggtacc tggactttct ggctcctgcc      960
aaggccaccc tggggggagac acacaggctg tttcccaata ccatgctgtt tgcctctgag     1020
```

```
gcctgtgtgg gctccaagtt ttgggagcag tctgtgaggc tgggctcctg ggatagaggg    1080
atgcagtaca gccacagcat catcaccaat ctgctgtacc atgtggtggg ctggactgac    1140
tggaatctgg ccctgaatcc tgaaggagga cctaactggg tcaggaattt tgtggacagc    1200
cccatcattg tggacatcac caaggacacc ttttacaagc agcccatgtt ttaccacctg    1260
ggccacttta gcaagtttat tcctgagggc tcccagagag tggggctggt tgccagccag    1320
aagaatgacc tggatgcagt ggcactgatg catcctgatg gctcagctgt tgtggtggtg    1380
ctgaatagat ccagcaagga tgtgcctctg accatcaagg atcctgctgt gggctttctg    1440
gagacaatct cacctggcta ctccattcac acctacctgt ggagaaggca gtga          1494
```

<210> SEQ ID NO 4
<211> LENGTH: 1494
<212> TYPE: DNA
<213> ORGANISM: Artificial Sequence
<220> FEATURE:
<223> OTHER INFORMATION: Synthetic construct

<400> SEQUENCE: 4

```
gccaggcctt gcatcccaaa gtctttcggc tacagctccg tggtgtgcgt gtgcaacgcc      60
acctattgtg actccttcga tccccctacc tttcccgccc tgggcacatt ttctagatac     120
gagtctacac gcagcggccg gagaatggag ctgagcatgg ccctatcca ggccaatcac      180 acaggaacag gcctgctgct gaccctgcag ccagagcaga agttccagaa ggtgaagggc     240
tttggcggag ccatgacaga tgcagccgcc ctgaacatcc tggccctgtc cccacccgcc     300
cagaatctgc tgctgaagtc ctacttctct gaggagggca tcggctataa catcatccgg     360
gtgcccatgg ccagctgcga cttttccatc agaacctaca catatgccga tacccctgac     420
gatttccagc tgcacaattt ttccctgcca gaggaggata caaagctgaa gatccccctg     480
attcaccggg ccctgcagct ggcacagcgc ccgtgagcc tgctggccag ccctggacc      540 tcccctacat ggctgaagac caacggcgcc gtgaatggca agggctctct gaagggacag     600
cctggcgaca tctaccacca gacatggggc agatatttcg tgaagtttct ggatgcctac     660
gccgagcaca agctgcagtt ctgggccgtg acagcagaga tgagccttc tgccggcctg     720 ctgagcggct atcccttcca gtgcctgggc tttacacctg agcaccagcg ggactttatc     780
gccagagatc tgggcccaac cctggccaac tccacacacc acaatgtgag gctgctgatg     840
ctggacgatc agcgcctgct gctgcctcac tgggccaagg tggtgctgac cgacccagag     900
gccgccaagt acgtgcacgg catcgccgtg cactggtatc tggatttcct ggcacctgca     960
aaggccaccc tgggagagac acaccggctg ttccctaaca ccatgctgtt tgccagcgag    1020
gcctgcgtgg gctccaagtt ttgggagcag tccgtgaggc tgggatcttg gacagaggc    1080 atgcagtact cccactctat catcaccaat ctgctgtatc acgtggtggg ctggacagac    1140
tggaacctgg ccctgaatcc agagggcggc cccaactggg tgagaaattt cgtggatagc    1200
cccatcatcg tggacatcac caaggataca ttctacaagc agccaatgtt ttatcacctg    1260
ggccacttct ctaagtttat ccctgagggc agccagaggg tgggcctggt ggccagccag    1320
aagaacgacc tggatgccgt ggccctgatg caccctgatg gctccgccgt ggtggtggtg    1380
ctgaatcgct ctagcaagga cgtgcctctg accatcaagg atccagccgt gggatttctg    1440
gagactattt cacctggcta ttcaattcat acctacctgt ggaggaggca gtga          1494
```

<210> SEQ ID NO 5

```
<211> LENGTH: 1611
<212> TYPE: DNA
<213> ORGANISM: Artificial Sequence
<220> FEATURE:
<223> OTHER INFORMATION: Synthetic construct

<400> SEQUENCE: 5
atggagtttt caagtccttc cagagaggaa tgtcccaagc ctttgagtag ggtaagcatc      60
atggctggca gcctcacagg attgcttcta cttcaggcag tgtcgtgggc atcaggtgcc     120
aggccctgca tccctaagag ctttggctac agctctgtgg tgtgtgtgtg caatgccacc     180
tactgtgaca gctttgaccc cccacctttc ctgccctgg gcaccttcag cagatatgag      240
agcaccaggt ctgggaggag gatggagctg agcatggggc ccatccaggc taatcacact     300
ggcactggcc tgctgctgac cctgcagcct gagcagaagt ccagaaagt aaagggcttt      360
ggaggggcca tgactgatgc tgctgctctg aacatcctgg ccctgagccc cctgcccag      420
aatctgctgc tgaagagcta cttctctgag gagggcattg ctataacat catcagggtg      480
cccatggcca gctgtgactt cagcatcagg acctacacct atgctgacac ccctgatgat     540
ttccagctgc acaacttcag cctgcctgag gaggatacca agctgaagat cccactgatc     600
cacgggctc tgcagctggc ccagaggcct gtgagcctgc tggccagccc ctggaccagc      660
cccacttggc tgaagaccaa tggggctgtg aatgggaagg ggagcctgaa gggacagcct     720
ggagacatct accaccagac ctgggccaga tactttgtga gttcctgga tgcctatgct      780
gagcacaagc tgcagttctg ggctgtgact gctgagaatg agccttctgc tgggctgctg     840
tctggctacc ccttccaatg cctgggcttc acccctgagc atcagaggga cttcattgcc     900
agggacctgg gcctaccct ggccaacagc actcaccata atgttaggct gctgatgctg      960
gatgaccaga ggctgctgct gccccactgg gctaaggtgg tgctgactga ccctgaggct    1020
gctaaatatg tgcatggcat tgctgtgcat tggtacctgg actttctggc tcctgccaag    1080
gccaccctgg gggagaccca caggctgttc cccaacacca tgctgtttgc ctctgaggcc    1140
tgtgtgggca gcaagttctg ggagcagtct gtgaggctgg gcagctggga tagggggatg    1200
cagtacagcc acagcatcat caccaacctg ctgtaccatg tggtgggctg gactgactgg    1260
aacctggccc tgaaccctga ggaggacct aactgggtca gaaactttgt ggacagcccc     1320
atcattgtgg acatcaccaa ggacaccttt tacaagcagc ccatgttcta ccacctgggc    1380
cacttcagca agttcatccc tgagggcagc cagagagtgg ggctggtggc cagccagaag    1440
aatgacctgg atgctgtggc tctgatgcat cctgatggct ctgctgtggt ggtggtgctg    1500
aacaggagct ctaaggatgt gcctctgacc atcaaggatc ctgctgtggg cttcctggag    1560
accatcagcc tggctacag catccacacc tacctgtgga ggaggcagtg a              1611

<210> SEQ ID NO 6
<211> LENGTH: 1611
<212> TYPE: DNA
<213> ORGANISM: Artificial Sequence
<220> FEATURE:
<223> OTHER INFORMATION: Synthetic construct

<400> SEQUENCE: 6
atggagtttt caagtccttc cagagaggaa tgtcccaagc ctttgagtag ggtaagcatc      60
atggctggca gcctcacagg attgcttcta cttcaggcag tgtcgtgggc atcaggtgcc     120
aggccctgta tccctaagag ctttggctac agctcagtag tttgtgtctg taatgccaca     180
tactgtgact cctttgaccc ccctaccttc cctgccctgg gaaccttcag cagatatgag     240
```

```
tcaacaagat caggaaggag gatggagctg tcaatgggac ccatccaggc taatcacaca    300
ggcacaggcc tgctgctgac cctgcagcca gaacagaagt tccagaaagt gaagggattt    360
ggaggagcca tgacagatgc tgctgctctc aacatcctgg ccctgtcacc ccctgcccag    420
aatctgctgc tgaagtcata cttctctgaa aaggaattg gatataacat catcagggtg     480
cccatggcca gctgtgactt ctccatcagg acctacacct atgctgacac ccctgatgat    540
ttccagctgc acaacttcag cctcccagag aagataccag agctcaagat ccctctgata    600
catagggcac tgcagctggc ccagaggcct gtgtcactcc tggccagccc ctggacatca    660
cccacttggc tcaagaccaa tggagctgtg aatggaaagg gatcactcaa gggacagcct    720
ggagacatct accaccagac ctgggccaga tactttgtga agttcctgga tgcctatgct    780
gagcacaagc tgcagttctg ggcagtgaca gctgaaaatg agccttctgc tggactgctg    840
tcaggatacc ccttccagtg tctgggcttc accctgaac atcagaggga cttcattgcc     900
agggacctgg gacctaccct tgccaactca actcaccaca atgtcaggct gctcatgctg    960
gatgaccaga ggctgctgct gccccactgg gccaaggtgg tgctgacaga cccagaagct   1020
gctaaatatg tgcatggcat tgctgtgcat tggtacctgg acttcctggc tccagccaag   1080
gccaccctgg gagagacaca caggctgttc cccaacacca tgctctttgc ctctgaggcc   1140
tgtgtgggct ccaagttctg ggagcagtca gtgaggctgg gctcctggga tagggggaatg  1200 cagtacagcc acagcatcat cacaaaacctc ctgtaccatg tggtgggctg gactgactgg   1260
aacctggccc tgaaccctga aggaggaccc aactgggtca gaaattttgt ggactcaccc   1320
atcattgtgg acatcaccaa ggacacattc tacaagcagc ccatgttcta ccacctgggc   1380
cacttcagca agttcatccc tgagggctcc cagagggtgg gactggtggc ctcacagaag   1440
aatgacctgg atgcagtggc cctgatgcat cctgatggct ctgctgtggt ggttgtgctg   1500
aatagatcct ctaaggatgt gcctctgacc atcaaggatc ctgctgtggg cttcctggag   1560
acaatctcac ctggctactc catccacacc tacctgtgga ggaggcagtg a             1611
```

<210> SEQ ID NO 7
<211> LENGTH: 1611
<212> TYPE: DNA
<213> ORGANISM: Artificial Sequence
<220> FEATURE:
<223> OTHER INFORMATION: Synthetic construct

<400> SEQUENCE: 7

```
atggagtttt caagtccttc cagagaggaa tgtcccaagc ctttgagtag ggtaagcatc     60
atggctggca gcctcacagg attgcttcta cttcaggcag tgtcgtgggc atcaggtgcc    120
aggccctgca tccctaagag ctttggctac agctctgtgg tgtgtgtgtg caatgccaca    180
tactgtgact cctttgaccc ccccaccttt cctgccctgg gcacattctc cagatatgag    240
agcacaagat ctgggagaag gatggagctg agcatgggc ccatccaggc taatcacact     300
ggcacaggcc tgctgctgac cctgcagcct gaacagaagt tcagaaagt gaagggattt     360 ggagggggcca tgacagatgc tgctgctctg aatatcctgg ccctgtcacc ccctgcccag   420
aatctgctgc tgaagagcta cttttcagaa aaggaattg gatataatat catcagagtg     480
cccatggcca gctgtgactt tccatcaga acctacacct atgcagacac ccctgatgat     540 ttcagctgc acaattttag cctgcctgag aagataccag agctgaagat accccctgatt    600 cacagggccc tgcagctggc ccagaggcct gttcactgc tggccagccc ctggacatca     660
```

| | |
|---|---|
| cccacctggc tgaagaccaa tggagctgtg aatgggaagg ggtcactgaa gggacagcct | 720 |
| ggagacatct accaccagac ctgggccaga tactttgtga agtttctgga tgcctatgct | 780 |
| gagcacaagc tgcagttttg ggcagtgaca gctgaaaatg agccttcagc tgggctgctg | 840 |
| tcaggatacc cctttcagtg cctgggcttt accectgaac atcagaggga ctttattgcc | 900 |
| agggacctgg gccctaccct ggccaatagc acccaccata atgtgaggtt gctgatgctg | 960 |
| gatgaccaga ggctgctgct gccccactgg gcaaaggtgg tgctgacaga ccctgaagca | 1020 |
| gctaaatatg ttcatggcat tgctgtgcat tggtacctgg actttctggc tcctgccaag | 1080 |
| gccacectgg gggagacaca caggctgttt cccaatacca tgctgtttgc ctctgaggcc | 1140 |
| tgtgtgggct ccaagttttg ggagcagtct gtgaggctgg gctcctggga tagagggatg | 1200 |
| cagtacagcc acagcatcat caccaatctg ctgtaccatg tggtgggctg gactgactgg | 1260 |
| aatctggccc tgaatcctga aggaggacct aactgggtca ggaattttgt ggacagcccc | 1320 |
| atcattgtgg acatcaccaa ggacaccttt tacaagcagc ccatgtttta ccacctgggc | 1380 |
| cactttagca gtttattcc tgagggctcc cagagagtgg ggctggttgc cagccagaag | 1440 |
| aatgacctgg atgcagtggc actgatgcat cctgatggct cagctgttgt ggtggtgctg | 1500 |
| aatagatcca gcaaggatgt gcctctgacc atcaaggatc ctgctgtggg ctttctggag | 1560 |
| acaatctcac ctggctactc cattcacacc tacctgtgga gaaggcagtg a | 1611 |

<210> SEQ ID NO 8
<211> LENGTH: 1611
<212> TYPE: DNA
<213> ORGANISM: Artificial Sequence
<220> FEATURE:
<223> OTHER INFORMATION: Synthetic construct

<400> SEQUENCE: 8

| | |
|---|---|
| atggagtttt caagtccttc cagagaggaa tgtcccaagc ctttgagtag ggtaagcatc | 60 |
| atggctggca gcctcacagg attgcttcta cttcaggcag tgtcgtgggc atcaggtgcc | 120 |
| aggccttgca tcccaaagtc tttcggctac agctccgtgg tgtgcgtgtg caacgccacc | 180 |
| tattgtgact cctccgatcc ccctaccttt cccgccctgg gcacattttc tagatacgag | 240 |
| tctacacgca gcggccggag aatggagctg agcatgggcc ctatccaggc caatcacaca | 300 |
| ggaacaggcc tgctgctgac cctgcagcca gagcagaagt tccagaaggt gaagggcttt | 360 |
| ggcggagcca tgacagatgc agccgccctg aacatcctgg ccctgtcccc accgcccag | 420 |
| aatctgctgc tgaagtccta cttctctgag gagggcatcg gctataacat catccgggtg | 480 |
| cccatggcca gctgcgactt ttccatcaga acctacacat atgccgatac ccctgacgat | 540 |
| ttccagctgc acaatttttc cctgccagag gaggatacaa agctgaagat cccctgatt | 600 |
| caccgggccc tgcagctggc acagcggccc gtgagcctgc tggccagccc ctggacctcc | 660 |
| cctacatggc tgaagaccaa cggcgccgtg aatggcaagg ctctctgaa gggacagcct | 720 |
| ggcgacatct accaccagac atgggccaga tatttcgtga agtttctgga tgcctacgcc | 780 |
| gagcacaagc tgcagttctg ggccgtgaca gcagagaatg agccttctgc cggcctgctg | 840 |
| agcggctatc ccttccagtg cctgggcttt acacctgagc accagcggga ctttatcgcc | 900 |
| agagatctgg gccaaccct ggccaactcc acacaccaca atgtgaggct gctgatgctg | 960 |
| gacgatcagc ggctgctgct gcctcactgg gccaaggtgg tgctgaccga cccagaggcc | 1020 |
| gccaagtacg tgcacggcat cgccgtgcac tggtatctgg atttcctggc acctgcaaag | 1080 |
| gccacectgg gagagacaca ccggctgttc cctaacacca tgctgtttgc cagcgaggcc | 1140 |

```
tgcgtgggct ccaagttttg ggagcagtcc gtgaggctgg gatcttggga cagaggcatg      1200
cagtactccc actctatcat caccaatctg ctgtatcacg tggtgggctg acagactgg      1260 aacctggccc tgaatccaga gggcggcccc aactgggtga aaatttcgt ggatagcccc      1320 atcatcgtgg acatcaccaa ggatacattc tacaagcagc caatgtttta tcacctgggc      1380
cacttctcta gtttatccc tgagggcagc cagagggtgg gcctggtggc cagccagaag      1440
aacgacctgg atgccgtggc cctgatgcac cctgatggct ccgccgtggt ggtggtgctg      1500
aatcgctcta gcaaggacgt gcctctgacc atcaaggatc cagccgtggg atttctggag      1560
actatttcac ctggctattc aattcatacc tacctgtgga ggaggcagtg a              1611
```

<210> SEQ ID NO 9
<211> LENGTH: 1611
<212> TYPE: DNA
<213> ORGANISM: Homo sapiens

<400> SEQUENCE: 9

```
atggagtttt caagtccttc cagagaggaa tgtcccaagc ctttgagtag ggtaagcatc        60
atggctggca gcctcacagg attgcttcta cttcaggcag tgtcgtgggc atcaggtgcc      120
cgcccctgca tccctaaaag cttcggctac agctcggtgg tgtgtgtctg caatgccaca      180
tactgtgact cctttgaccc cccgaccttt cctgccttg gtaccttcag ccgctatgag      240
agtacacgca gtgggcgacg gatggagctg agtatggggc ccatccaggc taatcacacg      300
ggcacaggcc tgctactgac cctgcagcca gaacagaagt tccagaaagt gaagggattt      360 ggagggggcca tgacagatgc tgctgctctc aacatccttg ccctgtcacc cctgcccaa      420 aatttgctac ttaaatcgta cttctctgaa gaggaatcg atataacat catccgggta      480 cccatggcca gctgtgactt ctccatccgc acctacacct atgcagacac ccctgatgat      540
ttccagttgc acaacttcag cctcccagag gaagatacca gctcaagat cccctgatt      600 caccgagccc tgcagttggc ccagcgtccc gtttcactcc ttgccagccc ctggacatca      660
cccacttggc tcaagaccaa tggagcggtg aatgggaagg ggtcactcaa gggcagccc      720 ggagacatct accaccagac ctgggccaga tactttgtga agttcctgga tgcctatgct      780
gagcacaagt tacagttctg gcagtgacga gctgaaaatg agccttctgc tgggctgttg      840
agtggatacc ccttccagtg cctgggcttc accctgaac atcagcgaga cttcattgcc      900
cgtgacctag tcctaccct cgccaacagt actcaccaca atgtccgcct actcatgctg      960
gatgaccaac gcttgctgct gccccactgg gcaaggtgg tactgacaga cccagaagca      1020
gctaaatatg ttcatggcat tgctgtacat tggtacctgg actttctggc tccagccaaa      1080
gccaccctag gggagacaca ccgcctgttc ccaacacca tgctctttgc ctcagaggcc      1140
tgtgtgggct ccaagttctg ggagcagagt gtgcggctag gctcctggga tcgagggatg      1200
cagtacagcc acagcatcat cacgaacctc ctgtaccatg tggtcggctg gaccgactgg      1260
aaccttgccc tgaaccccga aggaggaccc aattgggtgc gtaactttgt cgacagtccc      1320
atcattgtag acatcaccaa ggacacgtt tacaaacagc ccatgttcta ccaccttggc      1380
cacttcagca agttcattcc tgagggctcc cagagagtgg ggctggttgc cagtcagaag      1440
aacgacctgg acgcagtggc actgatgcat cccgatggct ctgctgttgt ggtcgtgcta      1500
aaccgctcct ctaaggatgt gcctcttacc atcaaggatc ctgctgtggg cttcctggag      1560
acaatctcac ctggctactc cattcacacc tacctgtggc gtcgccagtg a              1611
```

<210> SEQ ID NO 10
<211> LENGTH: 334
<212> TYPE: DNA
<213> ORGANISM: Artificial Sequence
<220> FEATURE:
<223> OTHER INFORMATION: Synthetic construct

<400> SEQUENCE: 10

```
ccctaaaatg gcaaacatt gcaagcagca aacagcaaac acacagccct ccctgcctgc      60
tgaccttgga gctggggcag aggtcagaca cctctctggg cccatgccac ctccaactgg    120
acacaggacg ctgtggtttc tgagccaggg ggcgactcag atcccagcca gtggacttag    180 ccctgtttg ctcctccgat aactggggtg accttggtta atattcacca gcagcctccc    240
ccgttgcccc tctggatcca ctgcttaaat acggacgagg cagggccct gtctcctcag    300 cttcaggcac caccactgac ctgggacagt gaat                                334
```

<210> SEQ ID NO 11
<211> LENGTH: 117
<212> TYPE: DNA
<213> ORGANISM: Artificial Sequence
<220> FEATURE:
<223> OTHER INFORMATION: Synthetic construct

<400> SEQUENCE: 11

```
ccctaaaatg gcaaacatt gcaagcagca aacagcaaac acacagccct ccctgcctgc      60
tgaccttgga gctggggcag aggtcagaca cctctctggg cccatgccac ctccaac       117
```

<210> SEQ ID NO 12
<211> LENGTH: 185
<212> TYPE: DNA
<213> ORGANISM: Artificial Sequence
<220> FEATURE:
<223> OTHER INFORMATION: Synthetic construct

<400> SEQUENCE: 12

```
gggcgactca gatcccagcc agtggactta gcccctgttt gctcctccga taactggggt     60
gaccttggtt aatattcacc agcagcctcc ccgttgcccc tctggatcca actgcttaaa   120
tacggacgag acagggccc tgtctcctca gcttcaggca ccaccactga cctgggacag   180
tgaat                                                                185
```

<210> SEQ ID NO 13
<211> LENGTH: 659
<212> TYPE: DNA
<213> ORGANISM: Artificial Sequence
<220> FEATURE:
<223> OTHER INFORMATION: Synthetic construct

<400> SEQUENCE: 13

```
gacattgatt attgactagt tattaatagt aatcaattac ggggtcatta gttcatagcc     60
catatatgga gttccgcgtt acataactta cggtaaatgg cccgcctggc tgaccgccca   120
acgacccccg cccattgacg tcaataatga cgtatgttcc catagtaacg ccaataggga   180
ctttccattg acgtcaatgg gtggagtatt tacggtaaac tgcccacttg gcagtacatc   240
aagtgtatca tatgccaagt acgccccta ttgacgtcaa tgacggtaaa tggcccgcct   300
ggcattatgc ccagtacatg acctatggg actttcctac ttggcagtac atctacgtat   360
tagtcatcgc tattaccatg gtcgaggtga gccccacgtt ctgcttcact ctccccatct   420 ccccccctc cccacccca attttgtatt tatttatttt ttaattattt tgtgcagcga   480
```

| tggggggcggg ggggggggggg gggcgcgcgc caggcggggc ggggcggggc gaggggcggg | 540 |
| gcggggcgag gcggagaggt gcggcggcag ccaatcagag cggcgcgctc cgaaagtttc | 600 |
| cttttatggc gaggcggcgg cggcggcggc cctataaaaa gcgaagcgcg cggcgggcg | 659 |

<210> SEQ ID NO 14
<211> LENGTH: 747
<212> TYPE: DNA
<213> ORGANISM: Artificial Sequence
<220> FEATURE:
<223> OTHER INFORMATION: Synthetic construct

<400> SEQUENCE: 14

| aggctcagag gcacacagga gtttctgggc tcaccctgcc cccttccaac ccctcagttc | 60 |
| ccatcctcca gcagctgttt gtgtgctgcc tctgaagtcc acactgaaca aacttcagcc | 120 |
| tactcatgtc cctaaaatgg gcaaacattg caagcagcaa acagcaaaca cacagccctc | 180 |
| cctgcctgct gaccttggag ctggggcaga ggtcagagac ctctctggcc catgccacc | 240 |
| tccaacatcc actcgacccc ttggaatttc ggtggagagg agcagaggtt gtcctggcgt | 300 |
| ggtttaggta gtgtgagagg ggtacccggg gatcttgcta ccagtggaac agccactaag | 360 |
| gattctgcag tgagagcaga gggccagcta agtggtactc tcccagagac tgtctgactc | 420 |
| acgccacccc ctccaccttg gacacaggac gctgtggttt ctgagccagg tacaatgact | 480 |
| cctttcggta agtgcagtgg aagctgtaca ctgcccaggc aaagcgtccg ggcagcgtag | 540 |
| gcgggcgact cagatcccag ccagtggact tagcccctgt ttgctcctcc gataactggg | 600 |
| gtgaccttgg ttaatattca ccagcagcct ccccgttgc ccctctggat ccactgctta | 660 |
| aatacgacg aggacagggc cctgtctcct cagcttcagg caccaccact gacctgggac | 720 |
| agtgaatgat cccctgatc tgcggcc | 747 |

<210> SEQ ID NO 15
<211> LENGTH: 418
<212> TYPE: DNA
<213> ORGANISM: Artificial Sequence
<220> FEATURE:
<223> OTHER INFORMATION: Synthetic construct

<400> SEQUENCE: 15

| ggatcttgct accagtggaa cagccactaa ggattctgca gtgagagcag agggccagct | 60 |
| aagtggtact ctcccagaga ctgtctgact cacgccaccc cctccacctt ggacacagga | 120 |
| cgctgtggtt tctgagccag gtacaatgac tcctttcggt aagtgcagtg gaagctgtac | 180 |
| actgcccagg caaagcgtcc gggcagcgta ggcgggcgac tcagatccca gccagtggac | 240 |
| ttagcccctg tttgctcctc cgataactgg ggtgaccttg gttaatattc accagcagcc | 300 |
| tccccgttg cccctctgga tccactgctt aaatacggac gaggacaggg ccctgtctcc | 360 |
| tcagcttcag gcaccaccac tgacctggga cagtgaatga tccccctgat ctgcggcc | 418 |

<210> SEQ ID NO 16
<211> LENGTH: 321
<212> TYPE: DNA
<213> ORGANISM: Artificial Sequence
<220> FEATURE:
<223> OTHER INFORMATION: Synthetic construct

<400> SEQUENCE: 16

```
aggctcagag gcacacagga gtttctgggc tcaccctgcc cccttccaac ccctcagttc    60
ccatcctcca gcagctgttt gtgtgctgcc tctgaagtcc acactgaaca aacttcagcc   120
tactcatgtc cctaaaatgg gcaaacattg caagcagcaa acagcaaaca cacagccctc   180
cctgcctgct gaccttggag ctggggcaga ggtcagagac ctctctgggc ccatgccacc   240
tccaacatcc actcgacccc ttggaatttc ggtggagagg agcagaggtt gtcctggcgt   300
ggtttaggta gtgtgagagg g                                             321
```

<210> SEQ ID NO 17
<211> LENGTH: 117
<212> TYPE: DNA
<213> ORGANISM: Homo sapiens

<400> SEQUENCE: 17

```
atggagtttt caagtccttc cagagaggaa tgtcccaagc ctttgagtag ggtaagcatc    60
atggctggca gcctcacagg attgcttcta cttcaggcag tgtcgtgggc atcaggt      117
```

<210> SEQ ID NO 18
<211> LENGTH: 39
<212> TYPE: PRT
<213> ORGANISM: Homo sapiens

<400> SEQUENCE: 18

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
            20                  25                  30

Ala Val Ser Trp Ala Ser Gly
        35

<210> SEQ ID NO 19
<211> LENGTH: 736
<212> TYPE: PRT
<213> ORGANISM: adeno-associated virus 3B

<400> SEQUENCE: 19

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Val Pro Gln Pro
            20                  25                  30

Lys Ala Asn Gln Gln His Gln Asp Asn Arg Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Glu Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Ile Leu Glu Pro
        115                 120                 125

Leu Gly Leu Val Glu Glu Ala Ala Lys Thr Ala Pro Gly Lys Lys Arg
    130                 135                 140

```
Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
            165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
            195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
                260                 265                 270

Phe Gly Tyr Ser Thr Pro Trp Gly Tyr Phe Asp Phe Asn Arg Phe His
            275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
                340                 345                 350

Val Leu Gly Ser Ala His Gln Gly Cys Leu Pro Pro Phe Pro Ala Asp
            355                 360                 365

Val Phe Met Val Pro Gln Tyr Gly Tyr Leu Thr Leu Asn Asn Gly Ser
            370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
            435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
            515                 520                 525
```

Asp Asp Glu Glu Lys Phe Phe Pro Met His Gly Asn Leu Ile Phe Gly
            530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
                705                 710                 715                 720

Tyr Ser Glu Pro Arg Pro Ile Gly Thr Arg Tyr Leu Thr Arg Asn Leu
            725                 730                 735

<210> SEQ ID NO 20
<211> LENGTH: 736
<212> TYPE: PRT
<213> ORGANISM: Artificial Sequence
<220> FEATURE:
<223> OTHER INFORMATION: Synthetic capsid protein

<400> SEQUENCE: 20

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

```
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
            195                 200                 205
Ala Pro Met Ala Asp Asn Asn Glu Gly Ala Asp Gly Val Gly Asn Ser
    210                  215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
                260                 265                 270
Phe Gly Tyr Ser Thr Pro Trp Gly Tyr Phe Asp Phe Asn Arg Phe His
            275                 280                 285
Cys His Phe Ser Pro Arg Asp Trp Gln Arg Leu Ile Asn Asn Asn Trp
    290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
            355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
            435                 440                 445
Gln Gly Thr Thr Ser Gly Thr Thr Asn Gln Ser Arg Leu Leu Phe Ser
    450                 455                 460
Gln Ala Gly Pro Gln Ser Met Ser Leu Gln Ala Arg Asn Trp Leu Pro
465                 470                 475                 480
Gly Pro Cys Tyr Arg Gln Gln Arg Leu Ser Lys Thr Ala Asn Asp Asn
                485                 490                 495
Asn Asn Ser Asn Phe Pro Trp Thr Ala Ala Ser Lys Tyr His Leu Asn
            500                 505                 510
Gly Arg Asp Ser Leu Val Asn Pro Gly Pro Ala Met Ala Ser His Lys
            515                 520                 525
Asp Asp Glu Glu Lys Phe Phe Pro Met His Gly Asn Leu Ile Phe Gly
    530                 535                 540
Lys Glu Gly Thr Thr Ala Ser Asn Ala Glu Leu Asp Asn Val Met Ile
545                 550                 555                 560
Thr Asp Glu Glu Glu Ile Arg Thr Thr Asn Pro Val Ala Thr Glu Gln
                565                 570                 575
```

```
Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 21
<211> LENGTH: 736
<212> TYPE: PRT
<213> ORGANISM: adeno-associated virus 9

<400> SEQUENCE: 21

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220
```

-continued

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
            245                 250                 255

Tyr Lys Gln Ile Ser Asn Ser Thr Ser Gly Ser Ser Asn Asp Asn
        260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
        290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Gly Val Lys Thr Ile Ala Asn
            325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
            405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
            435                 440                 445

Lys Thr Ile Asn Gly Ser Gly Gln Asn Gln Gln Thr Leu Lys Phe Ser
450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
            485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
            515                 520                 525

Glu Gly Glu Asp Arg Phe Phe Pro Leu Ser Gly Ser Leu Ile Phe Gly
            530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
            565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
            595                 600                 605

Asp Arg Asp Val Tyr Leu Gln Gly Pro Ile Trp Ala Lys Ile Pro His
            610                 615                 620

Thr Asp Gly Asn Phe His Pro Ser Pro Leu Met Gly Gly Phe Gly Met
625                 630                 635                 640

```
Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735

<210> SEQ ID NO 22
<211> LENGTH: 66
<212> TYPE: DNA
<213> ORGANISM: Simian virus 40

<400> SEQUENCE: 22
gtaaatataa aattttaag tgtataatgt gttaaactac tgattctaat tgtttctctc    60
ttttag                                                              66

<210> SEQ ID NO 23
<211> LENGTH: 208
<212> TYPE: DNA
<213> ORGANISM: Bos taurus

<400> SEQUENCE: 23
ctgtgccttc tagttgccag ccatctgttg tttgccccct ccccgtgcct tccttgaccc    60
tggaaggtgc cactcccact gtcctttcct aataaaatga ggaaattgca tcgcattgtc   120
tgagtaggtg tcattctatt ctggggggtg ggtgggca ggacagcaag gggaggatt     180 gggaagacaa tagcaggcat gctgggga                                     208

<210> SEQ ID NO 24
<211> LENGTH: 736
<212> TYPE: PRT
<213> ORGANISM: Artificial Sequence
<220> FEATURE:
<223> OTHER INFORMATION: Synthetic capsid protein

<400> SEQUENCE: 24

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125
```

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205

Ala Pro Met Ala Asp Asn Asn Glu Gly Ala Asp Gly Val Gly Asn Ser
210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
530                 535                 540

```
Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
            565                 570                 575

Tyr Gly Thr Val Ala Asn Asn Leu Gln Ser Ser Asn Thr Ala Pro Thr
                580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
            645                 650                 655

Asn Pro Pro Thr Thr Phe Ser Pro Ala Lys Phe Ala Ser Phe Ile Thr
                660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
            725                 730                 735

<210> SEQ ID NO 25
<211> LENGTH: 536
<212> TYPE: PRT
<213> ORGANISM: Homo sapiens

<400> SEQUENCE: 25

Met Glu Phe Ser Ser Pro Ser Arg Glu Glu Cys Pro Lys Pro Leu Ser
1               5                   10                  15

Arg Val Ser Ile Met Ala Gly Ser Leu Thr Gly Leu Leu Leu Leu Gln
                20                  25                  30

Ala Val Ser Trp Ala Ser Gly Ala Arg Pro Cys Ile Pro Lys Ser Phe
            35                  40                  45

Gly Tyr Ser Ser Val Val Cys Val Cys Asn Ala Thr Tyr Cys Asp Ser
        50                  55                  60

Phe Asp Pro Pro Thr Phe Pro Ala Leu Gly Thr Phe Ser Arg Tyr Glu
65                  70                  75                  80

Ser Thr Arg Ser Gly Arg Arg Met Glu Leu Ser Met Gly Pro Ile Gln
                85                  90                  95

Ala Asn His Thr Gly Thr Gly Leu Leu Leu Thr Leu Gln Pro Glu Gln
            100                 105                 110

Lys Phe Gln Lys Val Lys Gly Phe Gly Gly Ala Met Thr Asp Ala Ala
        115                 120                 125

Ala Leu Asn Ile Leu Ala Leu Ser Pro Pro Ala Gln Asn Leu Leu Leu
130                 135                 140

Lys Ser Tyr Phe Ser Glu Glu Gly Ile Gly Tyr Asn Ile Ile Arg Val
145                 150                 155                 160

Pro Met Ala Ser Cys Asp Phe Ser Ile Arg Thr Tyr Thr Tyr Ala Asp
                165                 170                 175

Thr Pro Asp Asp Phe Gln Leu His Asn Phe Ser Leu Pro Glu Glu Asp
            180                 185                 190
```

-continued

```
Thr Lys Leu Lys Ile Pro Leu Ile His Arg Ala Leu Gln Leu Ala Gln
        195                 200                 205

Arg Pro Val Ser Leu Leu Ala Ser Pro Trp Thr Ser Pro Thr Trp Leu
    210                 215                 220

Lys Thr Asn Gly Ala Val Asn Gly Lys Gly Ser Leu Lys Gly Gln Pro
225                 230                 235                 240

Gly Asp Ile Tyr His Gln Thr Trp Ala Arg Tyr Phe Val Lys Phe Leu
                245                 250                 255

Asp Ala Tyr Ala Glu His Lys Leu Gln Phe Trp Ala Val Thr Ala Glu
                260                 265                 270

Asn Glu Pro Ser Ala Gly Leu Leu Ser Gly Tyr Pro Phe Gln Cys Leu
            275                 280                 285

Gly Phe Thr Pro Glu His Gln Arg Asp Phe Ile Ala Arg Asp Leu Gly
        290                 295                 300

Pro Thr Leu Ala Asn Ser Thr His His Asn Val Arg Leu Leu Met Leu
305                 310                 315                 320

Asp Asp Gln Arg Leu Leu Leu Pro His Trp Ala Lys Val Val Leu Thr
                325                 330                 335

Asp Pro Glu Ala Ala Lys Tyr Val His Gly Ile Ala Val His Trp Tyr
                340                 345                 350

Leu Asp Phe Leu Ala Pro Ala Lys Ala Thr Leu Gly Glu Thr His Arg
            355                 360                 365

Leu Phe Pro Asn Thr Met Leu Phe Ala Ser Glu Ala Cys Val Gly Ser
        370                 375                 380

Lys Phe Trp Glu Gln Ser Val Arg Leu Gly Ser Trp Asp Arg Gly Met
385                 390                 395                 400

Gln Tyr Ser His Ser Ile Ile Thr Asn Leu Leu Tyr His Val Val Gly
                405                 410                 415

Trp Thr Asp Trp Asn Leu Ala Leu Asn Pro Glu Gly Gly Pro Asn Trp
                420                 425                 430

Val Arg Asn Phe Val Asp Ser Pro Ile Ile Val Asp Ile Thr Lys Asp
            435                 440                 445

Thr Phe Tyr Lys Gln Pro Met Phe Tyr His Leu Gly His Phe Ser Lys
        450                 455                 460

Phe Ile Pro Glu Gly Ser Gln Arg Val Gly Leu Val Ala Ser Gln Lys
465                 470                 475                 480

Asn Asp Leu Asp Ala Val Ala Leu Met His Pro Asp Gly Ser Ala Val
                485                 490                 495

Val Val Val Leu Asn Arg Ser Ser Lys Asp Val Pro Leu Thr Ile Lys
            500                 505                 510

Asp Pro Ala Val Gly Phe Leu Glu Thr Ile Ser Pro Gly Tyr Ser Ile
        515                 520                 525

His Thr Tyr Leu Trp Arg Arg Gln
    530                 535
```

POLYNUCLEOTIDES

FIELD OF THE INVENTION

The present invention relates to polynucleotides comprising a GBA nucleotide sequence encoding β-Glucocerebrosidase (GCase), viral particles comprising the polynucleotides and treatments utilising the polynucleotides.

BACKGROUND TO THE INVENTION

Gaucher disease (GD) is an autosomal recessive lipid storage disease characterised by the deposition of glucocerebroside in cells of the macrophage-monocyte system. GD is caused by mutations in the housekeeping GBA gene that impairs activity and/or production of the enzyme β-Glucocerebrosidase (GCase).

There are three major types of GD which are characterised by the specific mutations which have been identified, and each type can display differing clinical symptoms. Type 1 GD has little or no involvement with the central nervous system but is mainly characterised by visceral manifestations such as enlarged spleen and liver, low blood cell counts, bleeding problems and bone disease. For the past 20 years, enzyme replacement therapy has emerged as the standard of care for type 1 GD. In addition to its high cost (~$200,000 or ~£150,000/patient/year), enzyme replacement therapy treatment in GD generally requires one or more injections every other week for life. This leads to a high proportion of GD patients displaying high levels of treatment burden.

Accordingly, there is a need to provide an effective therapy vector for the treatment of GD, i.e. one that allows for a high level of GCase expression.

The present application relates to a gene therapy approach for treating GD, involving administering a viral particle comprising a GBA polynucleotide encoding GCase. The polynucleotides and viral particles described herein can provide higher GCase expression compared to polynucleotides comprising a wild type GCase encoding polynucleotides. Such a gene therapy approach would avoid the need for frequent and lifelong intravenous injections of GCase.

SUMMARY OF THE INVENTION

The present application demonstrates that specific modifications to a GBA nucleotide sequence encoding for GCase can help to improve the expression level and the activity of the expressed GCase polypeptide in vitro and/or in vivo. For example, the present application demonstrates that using a codon-optimised GBA nucleotide sequence can improve the expression and/or activity of the encoded GCase protein. Such modified (i.e. non wild-type) and/or codon-optimised GBA nucleotide sequences may be further modified to provide further improvements in the expression and/or activity of the encoded GCase protein. Further modifications may include providing further modifications in the GBA nucleotide sequence such as the removal of CpG motifs, and/or the use of particular gene regulatory elements comprising specific promoter and/or enhancer sequences. It is believed that such improvements to a GBA nucleotide sequence can improve the efficacy of such a nucleotide in the treatment of GD.

These modifications provide a GBA nucleotide sequence which is expressed highly, for example in the liver, and which encodes a GCase polypeptide or fragment thereof. As demonstrated in the Examples, the polynucleotides of the invention express GCase activity at higher levels than wild type GBA.

Accordingly, in a first aspect of the invention, there is provided a polynucleotide comprising a GBA nucleotide sequence, wherein the GBA nucleotide sequence encodes a β-Glucocerebrosidase (GCase) protein or fragment thereof and wherein at least a portion of the GBA nucleotide sequence is not wild type.

In a second aspect of the invention, there is provided a polynucleotide comprising a GBA nucleotide sequence, wherein the GBA nucleotide sequence encodes a GCase protein or a fragment thereof and comprises a sequence that is at least 95%, at least 96%, at least 97%, at least 98%, at least 99%, at least 99.5%, at least 99.8%, or 100% identical to a fragment of at least 1000, at least 1200, at least 1300, less than 1494, less than 1611, between 1000 and 1494, between 1000 and 1611, between 1300 and 1494, between 1300 and 1611, or around 1494 nucleotides of SEQ ID NO: 1-8.

In a third aspect of the invention, there is provided a viral particle comprising a recombinant genome comprising the polynucleotide of the invention.

In a fourth aspect of the invention, there is provided a composition comprising the polynucleotide or viral particle of the invention and a pharmaceutically acceptable excipient.

In a fifth aspect of the invention, there is provided a method of treatment comprising administering an effective amount of the polynucleotide or viral particle of the invention to a patient.

In a sixth aspect of the invention, there is provided a use of the polynucleotide, viral particle or composition of the invention in the manufacture of a medicament for use in a method of treatment.

In a seventh aspect of the invention, there is provided the use of the polynucleotide, viral particle or composition of the invention in the manufacture of a medicament for achieving a stable GCase activity in a subject.

In an eighth aspect of the invention, there is provided the use of the polynucleotide, viral particle or composition of the invention in the manufacture of a medicament for providing greater GCase bioavailability in a subject compared to the bioavailability from GCase enzyme replacement therapy, wherein the bioavailability is measured over a period of 2 weeks from administration.

In a ninth aspect of the invention, there is provided a method of achieving a stable GCase activity in a subject by administering to the subject the polynucleotide, viral particle or composition of the invention.

In a tenth aspect of the invention, there is provided a method of providing greater GCase bioavailability in a subject compared to the bioavailability from GCase enzyme replacement therapy by administering to the subject the polynucleotide, viral particle or composition of the invention, wherein the bioavailability is measured over a period of 2 weeks from administration.

In an eleventh aspect of the invention, there is provided a polynucleotide, viral particle or composition of the invention, for use in a method of expressing the GBA nucleotide sequence and achieving a stable GCase activity in a subject.

In a twelfth aspect of the invention, there is provided a polynucleotide, viral particle or composition of the invention, for use in a method of expressing the GBA nucleotide sequence and providing greater GCase bioavailability in a subject compared to the bioavailability from GCase enzyme replacement therapy, wherein the bioavailability is measured over a period of 2 weeks from administration.

In a thirteenth aspect of the invention, there is provided the use of the polynucleotide, viral particle or composition of the invention in the manufacture of a medicament for reducing the levels of hexosylceramide and/or hexosylsphingosine in a subject suffering from a disease or condition associated with GCase deficiency.

In a fourteenth aspect of the invention, there is provided a method of reducing the levels of hexosylceramide and/or hexosylsphingosine in a subject suffering from a disease or condition associated with GCase deficiency by administering to the subject the polynucleotide, viral particle or composition of the invention.

In a fifteenth aspect of the invention, there is provided a polynucleotide, viral particle or composition of the invention, for use in a method of reducing levels of hexosylceramide and/or hexosylsphingosine in a subject suffering from a disease or condition associated with GCase deficiency, optionally wherein reducing hexosylceramide and/or hexosylsphingosine levels leads to the treatment of the disease or condition associated with GCase deficiency.

DESCRIPTION OF THE FIGURES

FIG. 2—Dose-dependent liver expression and secretion of human GCase into murine bloodstream following AAV2/8-FLF-PL28 injection. (A) Representative image of mouse livers stained for GCase 12-weeks post AAV2/8-PL28 injection. DAB (3,3'-Diaminobenzidine) was used to visualize GCase and haematoxylin was used as counterstain. (B) Levels of GCase as measured by activity assay in serum of mice treated with increased doses of AAV2/8-PL28. n=5, C57BL/6 mice in each treatment group. Error bars show mean±SD.

FIG. 9—Sequence listing.

FIG. 11: (A) Enzyme replacement therapy (ERT) (velaglucerase alfa (VPRIV®) (60 U/kg)) pharmacokinetics and half-life calculation in wild type mice. One-phase decay model equation: Y0 is the Y-value when X (time) is zero. Plateau is the Y-value at infinite times. K is the rate constant. Tau is the time constant. Half-life is in the time units of the X-axis. Span is the difference between Y0 and Plateau. (B) Comparison between serum pharmacokinetic profile of GCase activity after a single injection of enzyme replacement therapy (velaglucerase alfa (VPRIV®) (60 U/kg), solid black) and gene therapy with FLF-PL64, following administration in wild type mice.

FIG. 15: AAV-GBA (AAV-FLF-PL64) gene therapy shows better substrate clearance than velaglucerase alfa (VPRIV®, labelled Enyme Replacement Therapy (ERT)) in $gba^{9v/null}$ mice. LC/MS analysis of hexosylceramide and hexosylsphingosine levels in liver, spleen, and bone marrow in AAV-FLF-PL64 and ERT treated groups. Levels were standardised to the levels measured in the vehicle control group. AAV-GBA (AAV-FLF-PL64) injected at dose of $2\times10^{12}$ vg/kg; samples collected 12-weeks p.i.; ERT at dose 60 U/kg and administered by injection every two weeks. ERT samples were collected 1-2 hours post the last injection. Mean±SEM, (n=10), P≤0.005, **P≤0.0005

DETAILED DESCRIPTION

General Definitions

Figure 1:
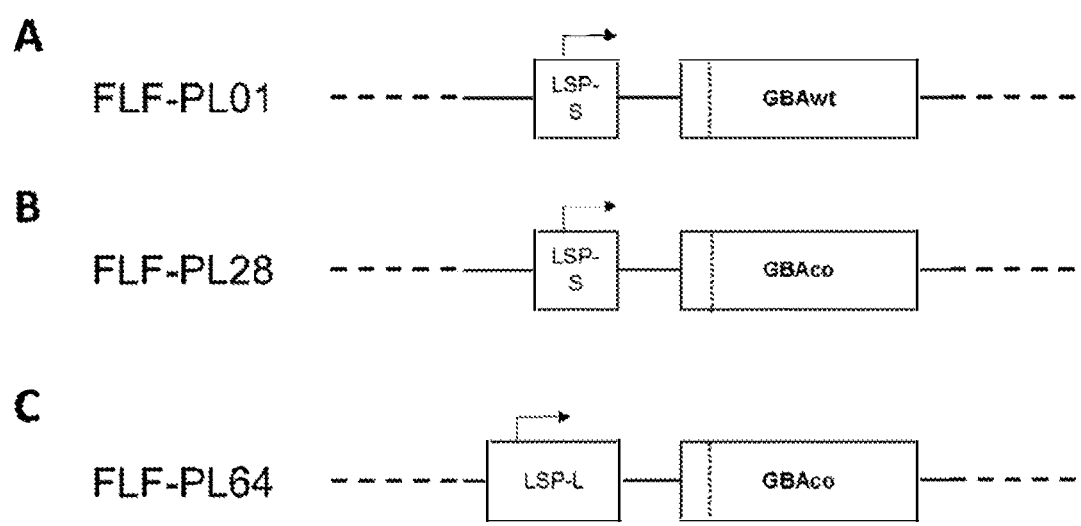
FIG. 1—Schematics of the GBA cassettes from the constructs FLF-PL01, FLF-PL28, and FLF-PL64. LSP-S and LSP-L: liver specific promoters; GBAwt: wild type human GBA nucleotide sequence; GBAco: human GBA nucleotide sequence codon-optimised (except for stretch encoding signal peptide, the end of which is represented by a dotted line).

Unless defined otherwise, technical and scientific terms used herein have the same meaning as commonly understood by a person skilled in the art to which this invention belongs.

In general, the term "comprising" is intended to mean including but not limited to. For example, the phrase "a polynucleotide comprising a GBA nucleotide sequence" should be interpreted to mean that the polynucleotide has a GBA nucleotide sequence, but the polynucleotide may contain additional nucleotides.

In some embodiments of the invention, the word "comprising" is replaced with the phrase "consisting of". The term "consisting of" is intended to be limiting. For example, the phrase "a polynucleotide consisting of a GBA nucleotide sequence" should be understood to mean that the polynucleotide has a GBA nucleotide sequence and no additional nucleotides.

As used herein, "between" when referring to two endpoints to define a range of values should be taken to mean "between and including". Thus, a range defined as "between 5 and 10" includes all values greater than 5 and less than 10, as well as the discrete values 5 and 10 themselves.

The terms "protein" and "polypeptide" are used interchangeably herein, and are intended to refer to a polymeric chain of amino acids of any length.

For the purpose of this invention, in order to determine the percent identity of two sequences (such as two polynucleotide or two polypeptide sequences), the sequences are aligned for optimal comparison purposes (e.g., gaps can be introduced in a first sequence for optimal alignment with a second sequence). The nucleotide or amino acid residues at each position are then compared. When a position in the first sequence is occupied by the same nucleotide or amino acid residue as the corresponding position in the second sequence, then the nucleotides or amino acids are identical at that position. The percent identity between the two sequences is a function of the number of identical positions shared by the sequences (i.e., % identity=number of identical positions/total number of positions in the reference sequence×100).

Typically the sequence comparison is carried out over the length of the reference sequence. For example, if the user wished to determine whether a given ("test") sequence is 95% identical to SEQ ID NO: 1, SEQ ID NO: 1 would be the reference sequence. For example, to assess whether a sequence is at least 80% identical to SEQ ID NO: 1 (an example of a reference sequence), the skilled person would carry out an alignment over the length of SEQ ID NO: 1, and identify how many positions in the test sequence were identical to those of SEQ ID NO: 1. If at least 80% of the positions are identical, the test sequence is at least 80% identical to SEQ ID NO: 1. If the sequence is shorter than SEQ ID NO: 1, the gaps or missing positions should be considered to be non-identical positions.

The skilled person is aware of different computer programs that are available to determine the homology or identity between two sequences. For instance, a comparison of sequences and determination of percent identity between two sequences can be accomplished using a mathematical algorithm.

In an embodiment, the percent identity between two amino acid or nucleic acid sequences is determined using the Needleman and Wunsch (1970) algorithm which has been incorporated into the GAP program in the Accelrys GCG software package (available at www.accelrys.com/products/gcg/), using either a Bolsum 62 matrix or a PAM250 matrix, and a gap weight of 16, 14, 12, 10, 8, 6, or 4 and a length weight of 1, 2, 3, 4, 5, or 6.

For the purposes of the present invention, the term "fragment" refers to a contiguous portion of a sequence. For example, a fragment of SEQ ID NO: 1 of 50 nucleotides refers to 50 contiguous nucleotides of SEQ ID NO: 1.

A Polynucleotide

In one aspect, the present invention provides a polynucleotide comprising a GBA nucleotide sequence, wherein the GBA nucleotide sequence encodes a β-Glucocerebrosidase (GCase) protein or fragment thereof and wherein at least a portion of the GBA nucleotide sequence is not wild type.

The polynucleotide may further comprise one or more of the following features. The GBA nucleotide sequence, or portion of GBA nucleotide sequence that is not wild type, may be codon-optimised. The polynucleotide may (additionally) comprise a portion that is not codon-optimised. The polynucleotide may comprise an intron or a fragment of an intron.

The term "polynucleotide" refers to a polymeric form of nucleotides of any length, deoxyribonucleotides, ribonucleotides, or analogs thereof. For example, the polynucleotide may comprise DNA (deoxyribonucleotides) or RNA (ribonucleotides). The polynucleotide may consist of DNA. The polynucleotide may be mRNA. Since the polynucleotide may comprise RNA or DNA, all references to T (thymine) nucleotides may be replaced with U (uracil).

A GBA Nucleotide Sequence Encoding GCase

In one aspect, the polynucleotide provided herein comprises a GBA nucleotide sequence. The GBA nucleotide sequence typically encodes the β-Glucocerebrosidase (GCase) protein or fragment thereof.

The term "sequence that encodes" refers to a nucleotide sequence comprising an open reading frame comprising codons that encode the encoded polypeptide. For example, a nucleotide sequence that encodes a GCase protein or fragment thereof comprises codons that encode the amino acid sequence of a GCase protein or fragment thereof. An example of a GBA nucleotide sequence that encodes a wild type GCase protein is provided in SEQ ID NO: 9.

A GBA nucleotide sequence may be interrupted by non-coding nucleotides (e.g. an intron), but only nucleotides that encode the polypeptide should be considered to be part of the GBA nucleotide sequence. For example, a GBA nucleotide sequence that encodes a GCase protein will comprise any codons that encode an amino acid forming part of the GCase protein that is expressed from that coding sequence, irrespective of whether those codons are contiguous in sequence or separated by one or more non-coding nucleotides. In other words, a GBA polynucleotide which contains stretches of coding nucleotides interrupted by a stretch of non-coding nucleotides will be considered to comprise a "GBA nucleotide sequence" consisting of the non-contiguous coding stretches immediately juxtaposed (i.e. minus the non-coding stretch). However, herein, the stop codon will be considered to be part of the full length coding sequence.

A GBA nucleotide sequence encoding GCase and/or a GCase coding sequence as described herein may also include codons for a signal peptide. It is well known that some proteins, particularly those which are exported to different tissues, are expressed with a signal peptide. Signal peptides can be at the N-terminus of a protein sequence (and in this case at the 5' end of a coding sequence) and many signal peptides are cleaved following cellular processing. Thus, herein, a mature protein or polypeptide (such as a mature GCase protein or polypeptide) will be considered to be the resulting protein or polypeptide after the signal peptide has been processed and removed/cleaved (and thus no longer forms part of the polypeptide sequence).

The following Table describes codons that encode each amino acid:

| Amino Acid | Codon | Amino Acid | Codon | Amino Acid | Codon |
|---|---|---|---|---|---|
| Phenylalanine | TTC | Proline | CCT | Asparagine | AAT |
|  | TTT |  | CCC |  | AAC |
|  |  |  | CCA |  |  |
|  |  |  | CCG |  |  |
| Leucine | TTA | Threonine | ACT | Lysine | AAA |
|  | TTG |  | ACC |  | AAG |
|  | CTT |  | ACA |  |  |
|  | CTC |  | ACG |  |  |
|  | CTA |  |  |  |  |
|  | CTG |  |  |  |  |
| Isoleucine | ATT | Alanine | GCT | Aspartic Acid | GAT |
|  | ATC |  | GCC |  | GAC |
|  | ATA |  | GCA |  |  |
|  |  |  | GCG |  |  |
| Methionine | ATG | Tyrosine | TAT | Glutamic Acid | GAA |
|  |  |  | TAC |  | GAG |
| Valine | GTT | Histidine | CAT | Cysteine | TGT |
|  | GTC |  | CAC |  | TGC |
|  | GTA |  |  |  |  |
|  | GTG |  |  |  |  |
| Serine | TCT | Glutamine | CAA | Tryptophan | TGG |
|  | TCC |  | CAG |  |  |
|  | TCA |  |  |  |  |
|  | TCG |  |  |  |  |
|  | AGT |  |  |  |  |
|  | AGC |  |  |  |  |
| Arginine | CGT | Glycine | GGT |  |  |
|  | CGC |  | GGC |  |  |
|  | CGA |  | GGA |  |  |
|  | CGG |  | GGG |  |  |
|  | AGA |  |  |  |  |
|  | AGG |  |  |  |  |

The corresponding RNA codons will contain Us in place of the Ts in the Table above.

One aspect of the present invention provides a polynucleotide comprising a GBA nucleotide sequence, wherein the GBA nucleotide sequence encodes a GCase protein or a fragment thereof and comprises a sequence that is at least 95%, at least 96%, at least 97%, at least 98%, at least 99%, at least 99.5%, at least 99.8%, or 100% identical to a fragment of at least 1000, at least 1200, at least 1300, less than 1494, less than 1611, between 1000 and 1494, between 1000 and 1611, between 1300 and 1494, between 1300 and 1611, or around 1494 nucleotides of any one of SEQ ID NO: 1-8. Optionally, all or a portion of the GBA nucleotide sequence is codon-optimised. In one embodiment, the GBA nucleotide sequence comprises a sequence that is at least 98% identical to a fragment of at least 1300 nucleotides of SEQ ID NO: 1-8. In one embodiment, the GBA nucleotide sequence comprises a sequence that is at least 99% identical to a fragment of at least 1300 nucleotides of SEQ ID NO: 1-8.

In one example, the GBA nucleotide sequence may comprise a sequence that is at least 95%, at least 98%, at least 99%, at least 99.5%, at least 99.8%, or 100% identical to SEQ ID NO: 1. In one embodiment, the GBA nucleotide sequence comprises a sequence that is at least 98% identical to a fragment of at least 1300 nucleotides of SEQ ID NO: 1. In one embodiment, the GBA nucleotide sequence comprises a sequence that is at least 99% identical to a fragment of at least 1300 nucleotides of SEQ ID NO: 1. The GBA nucleotide sequence may comprise a sequence that is at least 95%, at least 98%, at least 99%, at least 99.5%, at least 99.8%, or 100% identical to SEQ ID NO: 5. The GBA nucleotide sequence may comprise a sequence that is at least 98% identical SEQ ID NO: 1. The GBA nucleotide sequence may comprise a sequence that is at least 99% identical SEQ ID NO: 1. The GBA nucleotide sequence may comprise a sequence that is at least 98% identical SEQ ID NO: 5. The GBA nucleotide sequence may comprise a sequence that is at least 99% identical SEQ ID NO: 5. In one embodiment, the GBA nucleotide sequence may comprise SEQ ID NO: 1. In another embodiment, the GBA nucleotide sequence may comprise SEQ ID NO: 5.

The GBA nucleotide sequence may comprise a sequence of SEQ ID NO: 1 or a variant of SEQ ID NO: 1 encoding a GCase protein having GCase activity. In these examples, a variant of SEQ ID NO: 1 is identical to SEQ ID NO: 1 except that it comprises nucleotide substitutions such that the GCase protein has 1, up to 2, up to 3, up to 4, up to 5, up to 6, up to 7, up to 8, up to 9, or up to 10 amino acid substitutions relative to the wild type GCase amino acid sequence of SEQ ID NO: 25. In these examples, the variant of SEQ ID NO: 1 may have 1, up to 2, up to 3, up to 4, up to 5, up to 6, up to 7, up to 8, up to 9, up to 10, up to 20, or up to 30 nucleotide substitutions relative to the sequence of SEQ ID NO: 1. The variant of SEQ ID NO: 1 may have 1, up to 2, up to 3, up to 4, up to 5, or up to 6 nucleotide substitutions relative to the sequence of SEQ ID NO: 1. In one example, the variant of SEQ ID NO: 1 has up to 4 nucleotide substitutions relative to the sequence of SEQ ID NO: 1 and/or encodes a GCase protein having up to 3 amino acid substitutions relative to the wild type amino acid GCase sequence of SEQ ID NO: 25. In one example, the variant of SEQ ID NO: 1 has up to 3 nucleotide substitutions relative to the sequence of SEQ ID NO: 1 and/or encodes a GCase protein having up to 2 amino acid substitutions relative to the wild type GCase amino acid sequence of SEQ ID NO: 25. In one example, the variant of SEQ ID NO: 1 has 1 nucleotide substitution relative to the sequence of SEQ ID NO: 1 and/or encodes a GCase protein having up to 1 amino acid substitution relative to the wild type GCase amino acid sequence of SEQ ID NO: 25.

The GBA nucleotide sequence may comprise a sequence of SEQ ID NO: 5 or a variant of SEQ ID NO: 5 encoding a GCase protein having GCase activity. In these examples, a variant of SEQ ID NO: 5 is identical to SEQ ID NO: 5 except that it comprises nucleotide substitutions such that the GCase protein has 1, up to 2, up to 3, up to 4, up to 5, up to 6, up to 7, up to 8, up to 9, or up to 10 amino acid substitutions relative to the wild type GCase amino acid sequence of SEQ ID NO: 25. In these examples, the variant of SEQ ID NO: 5 may have 1, up to 2, up to 3, up to 4, up to 5, up to 6, up to 7, up to 8, up to 9, up to 10, up to 20, or up to 30 nucleotide substitutions relative to the sequence of SEQ ID NO: 5. The variant of SEQ ID NO: 5 may have 1, up to 2, up to 3, up to 4, up to 5, or up to 6 nucleotide substitutions relative to the sequence of SEQ ID NO: 5. In one example, the variant of SEQ ID NO: 5 has up to 4 nucleotide substitutions relative to the sequence of SEQ ID NO: 5 and/or encodes a GCase protein having up to 3 amino acid substitutions relative to the wild type amino acid GCase sequence of SEQ ID NO: 25. In one example, the variant of SEQ ID NO: 5 has up to 3 nucleotide substitutions relative to the sequence of SEQ ID NO: 5 and/or encodes a GCase protein having up to 2 amino acid substitutions relative to the wild type GCase amino acid sequence of SEQ ID NO: 25. In one example, the variant of SEQ ID NO: 5 has 1 nucleotide substitution relative to the sequence of SEQ ID NO: 5 and/or encodes a GCase protein having up to 1 amino acid substitution relative to the wild type GCase amino acid sequence of SEQ ID NO: 25.

GCase Protein or Fragment Thereof

The polynucleotide comprises a GBA nucleotide sequence that encodes a GCase protein or fragment thereof.

β-glucocerebrosidase (GCase) is an enzyme with glucosylceramidase activity (EC 3.2.1.45) that hydrolyses the beta-glucosidic linkage of the chemical glucocerebroside, an intermediate in glycolipid metabolism that is abundant in cell membranes. Mutations in the GBA gene (which encodes GCase) can lead to an accumulation of glucocerebrosides in macrophages that infiltrate many vital organs, which manifests as Gaucher disease (GD). A typical wild type GCase polypeptide is encoded by SEQ ID NO: 9.

GCase (e.g. a GCase of SEQ ID NO: 25 encoded by SEQ ID NO: 9) is initially expressed as a precursor "immature" form, comprising a signal peptide (amino acid residues 1 to 39 of SEQ ID NO: 25 and codons 1 to 39 of SEQ ID NO: 9), and a mature GCase polypeptide region. After processing, the "mature" form of GCase lacks the signal peptide. The term "mature GCase" or "mature GCase polypeptide" refers to a GCase polypeptide that does not comprise the signal peptide, such as a GCase encoded by SEQ ID NOs: 1-4. A typical GCase signal peptide may be encoded by a nucleotide sequence of SEQ ID NO: 17 and have the polypeptide sequence of SEQ ID NO: 18.

The GCase or fragment thereof may be a variant GCase or fragment thereof, i.e. a GCase that does not have a sequence identical to SEQ ID NO: 25. In an embodiment, the GCase or fragment thereof that is encoded by a polypeptide of the present invention and/or by a GBA nucleotide sequence is at least 95%, at least 98%, at least 99%, at least 99.5%, at least 99.8%, or 100% identical to SEQ ID NO: 25; or at least 95%, at least 98%, at least 99%, at least 99.5%, at least 99.8%, or 100% identical to a fragment of SEQ ID NO: 25 at least 300, at least 350, at least 400, less than or equal to 536, less than or equal to 497, between 300 and 536, or between 300 and 497 amino acids in length. In an embodiment, the GCase protein or fragment thereof is at least 95%, at least 98%, at least 99%, at least 99.5%, at least 99.8%, or 100% identical to SEQ ID NO: 25; or at least 95%, at least 98%, at least 99%, at least 99.5%, at least 99.8%, or 100% identical to a fragment of SEQ ID NO: 25 about 497 amino acids in length. The GCase protein or fragment thereof may have a sequence of SEQ ID NO: 25. Preferably the GCase protein or a fragment thereof does not comprise the signal peptide of SEQ ID NO: 18. Preferably the GCase protein or fragment thereof is functional. A functional GCase protein or fragment is one which carries out hydrolysis of glucocerebroside.

The GBA nucleotide sequence may encode a GCase protein having 1, up to 2, up to 3, up to 4, or up to 5 amino acid substitutions relative to the wild type GCase amino acid sequence of SEQ ID NO: 25. In such examples, the GBA nucleotide sequence may encode a GCase protein having up to 3 amino acid substitutions relative to the wild type GCase amino acid sequence of SEQ ID NO: 25. The GBA nucleotide sequence may encode a GCase protein having up to 2 amino acid substitutions relative to the wild type GCase amino acid sequence of SEQ ID NO: 25. The GBA nucleotide sequence may encode a variant GCase protein having up to 1 amino acid substitution relative to the wild type GCase amino acid sequence of SEQ ID NO: 25.

It is within the abilities of the person skilled in the art to determine whether a GCase protein or fragment encoded by a GBA nucleotide sequence is functional. The skilled person merely needs to express the GCase nucleotide sequence, and test whether the expressed protein is active. For example, the skilled person could prepare a viral particle of the invention comprising a GBA nucleotide sequence linked to an operable promoter, and transduce cells with the viral particle under conditions suitable for expression of the GCase protein or fragment thereof. The activity (amount) of the expressed GCase protein or fragment thereof can be analysed using a a fluorometric, assay, such as the "serum GBA activity assay" described in Example 1.

For example, a suitable fluorogenic assay is as follows. β-Glucocerebrosidase (acid β-glucosidase; GCase) activity can be determined fluorometrically with 4-Methylumbelliferyl-β-D-glucopyranoside (4MU-Glc) as a substrate. Briefly, serum samples (0.5 μL, diluted 1:50) can be assayed in 50 mM Sodium Citrate, 25 mM Taurocholate, pH~5.75, 6 mM 4MU-Glc, for 30 min at 37° C. Relative fluorescence levels (RFU) may then be evaluated using excitation and emission wavelengths of 365 nm and 445 nm, respectively. GCase is expressed as nanomoles/h/mL of serum based on a 4-Methylumbelliferone (4-MU) standard curve.

A Portion of the GBA Nucleotide Sequence is not Wild Type

A portion of the GBA nucleotide sequence, for example the coding sequence that encodes GCase protein or a fragment thereof, may not be wild type. The wild type GCase-encoding GBA nucleotide sequence is represented by SEQ ID NO: 9, and a GBA nucleotide sequence that comprises a portion differing in sequence from that of SEQ ID NO: 9 comprises a portion that is not wild type.

In an embodiment, the portion of the GBA nucleotide sequence that is not wild type is codon-optimised. Codon-optimisation can improve expression of the nucleotide sequence, for example a GBA nucleotide sequence, in a particular tissue and/or in a particular organism. For example, if a nucleotide sequence is codon-optimised for expression in the human liver, the nucleotide sequence is modified to increase the number of codons that may be favoured (in the sense that such codons correspond to tRNA species which are more abundant than other tRNA species specific for the same amino acid) in the human liver. The skilled person would appreciate that codon-optimising a sequence may not entail changing every codon, not least because a "favoured codon" may already be present at some positions.

Such codon-optimisation may be subject to other factors. For example, it can be seen that the presence of CpGs has an adverse effect on expression and so the user may decide not to use favoured codons at positions where doing so introduces CpGs into the sequence; this will still be considered to be codon-optimisation. In an embodiment, a favoured codon that ends with a C nucleotide will not be included in the portion of the coding sequence that is codon-optimised, where the next codon in the sequence begins with a G. For example, codon CTC encodes leucine. In schemes where CTC is a favoured codon, it should not be used for encoding leucine where the next codon in the sequence begins with a G, such as codon GTT (or alternatively, the next codon—where possible—could be selected to avoid a G at the first position).

It is straightforward to determine the frequency of each codon used in a portion of a nucleotide sequence. The skilled person merely needs to enter the sequence of that portion into one of the readily-available algorithms that looks at codon usage and review the results. Alternatively, the user could simply count them.

In one embodiment, a polynucleotide of the invention comprises a GBA nucleotide sequence wherein 67% of the codons that encode histidine are CAC and 33% of the codons that encode histidine are CAT.

Optionally, the portion of the GBA nucleotide sequence that is codon-optimised is codon-optimised for expression in human liver cells. Optionally, the GBA nucleotide sequence is codon-optimised for expression in the human liver. Optionally, the portion of the GBA nucleotide sequence that is codon-optimised is a contiguous portion.

The portion that is codon-optimised can correspond to a sequence encoding part of, or an entire, GCase protein. For example, the coding sequence could be full-length (such as SEQ ID NO: 9), including the signal peptide which is not part of the mature GCase protein, and the entire coding sequence could be codon-optimised. Hence, reference herein to "a portion of the GBA sequence is codon-optimised" should be understood to mean "at least a portion of the GBA sequence is codon-optimised". Optionally, the portion of the GBA nucleotide sequence that is codon-optimised is at least 1000, at least 1200, at least 1300, less than 1600, less than 1500, between 1000 and 1600, between 1000 and 1500, between 1300 and 1500, or around 1494 nucleotides in length. Optionally, the portion of the GBA nucleotide sequence that is codon-optimised encodes (corresponds to) a mature GCase protein. For example, the GBA nucleotide sequence may encode a precursor GCase protein (i.e. including signal peptide), and if the portion of the GBA nucleotide sequence that is codon-optimised corresponds to the mature GCase protein, the signal peptide is not codon-optimised.

Thus in some embodiments, a portion of the GBA nucleotide sequence may not be codon-optimised, for example a portion of the coding sequence is not codon-optimised for expression in the liver. In some embodiments, the portion that is not codon-optimised is at least 80, at least 90, at least 100, at least 110, less than 200, less than 170, less than 140, or around 117 nucleotides. In some embodiments, the portion that is not codon-optimised in a GBA nucleotide sequence is the portion which encodes the signal peptide.

As discussed above, providing a polynucleotide sequence comprising a GBA nucleotide sequence that is partially or wholly codon-optimised can ensure that the encoded polypeptide (i.e. a GCase polypeptide) is expressed at a high level. It will be appreciated by one skilled in the art that expression of GCase from a polynucleotide sequence, such as a GBA nucleotide sequence of the present invention, or from a viral particle of the present invention, generally requires the presence of a promoter sequence or region upstream of and/or operably linked to the polynucleotide sequence. Thus in one embodiment, the present invention provides a polynucleotide comprising a GBA nucleotide sequence, wherein the GBA nucleotide sequence encodes a GCase polypeptide which is expressed in human liver cells at high levels when the GBA nucleotide sequence is operably linked to a promoter sequence. In some embodiments, the promoter sequence may be part of a transcriptional regulatory element. In some embodiments, the promoter sequence may be a liver-specific promoter sequence. In one embodiment, the promoter sequence is a promoter having SEQ ID NO: 12. In another embodiment, the promoter sequence is a promoter having SEQ ID NO: 15.

It will also be appreciated by one skilled in the art that making comparisons between polynucleotides or vectors of the invention and reference (comparator) polynucleotides or vectors such as a reference polynucleotide or a viral particle comprising a GBA nucleotide sequence of SEQ ID NO: 9, the reference polynucleotides or vectors may be identical to the polynucleotides or vectors of the invention except that the GBA nucleotide sequences are different. In other words, the different GBA nucleotide sequences being compared may be operably linked to the same promoter sequence. In some embodiments, the different GBA nucleotide sequences being tested may be operably linked to different (specified) promoter sequences.

Thus, in one embodiment, a GCase polypeptide encoded by the GBA nucleotide sequence is expressed in human liver cells at higher levels compared to a reference wild type GBA sequence. The reference wild type GBA nucleotide sequence may be SEQ ID NO: 9. In an embodiment, a polypeptide encoded by the GBA nucleotide sequence is expressed in human liver cells at higher levels compared to a polypeptide encoded by a nucleotide sequence comprising a GBA nucleotide sequence of SEQ ID NO: 9 and a promoter element of SEQ ID NO: 13 (wherein the GBA nucleotide sequence of SEQ ID NO: 9 and the promoter element of SEQ ID NO: 13 are preferably operably linked). In an embodiment, a polypeptide encoded by the GBA nucleotide sequence is expressed in human liver cells at higher levels compared to a polypeptide encoded by a nucleotide sequence comprising a GBA nucleotide sequence of SEQ ID NO: 9 and a transcription regulatory element of SEQ ID NO: 10 (wherein the GBA nucleotide sequence of SEQ ID NO: 9 and the promoter element of SEQ ID NO: 10 are preferably operably linked). In such embodiments the GCase encoded by the GBA nucleotide sequence may be expressed in human liver cells at least 1.1×, at least 1.2×, at least 1.3×, at least 1.4×, or at least 1.5× higher. In an embodiment, a GCase polypeptide encoded by the GBA nucleotide sequence is expressed in human liver cells at higher or non-statistically significant different levels compared to a polypeptide encoded by an otherwise identical reference polynucleotide comprising a GBA nucleotide sequence of SEQ ID NO: 9 operably linked to a promoter of SEQ ID NO: 13, wherein the two polynucleotides are delivered to the cells in the same way and in the same amounts.

In one embodiment, when the polynucleotide sequence comprising a GBA nucleotide sequence is administered to a subject, or a non-human mammal such as a mouse, the GCase is present in the serum of the subject or non-human animal at higher levels (for example, at 4 or 8 or 12 weeks post-administration) compared to GCase encoded by an otherwise identical nucleotide sequence comprising a GBA nucleotide sequence of SEQ ID NO: 9 operably linked to a promoter element of SEQ ID NO: 12, 13 or 15, wherein the polynucleotides comprising the GBA nucleotide are administered in the same way and in the same amounts.

The skilled person may determine whether GCase is expressed from a given GBA nucleotide sequence (for example, a codon-optimised GBA nucleotide sequence) at higher levels compared to a reference sequence (for example, a wild type GBA nucleotide sequence, such as SEQ ID NO: 9) by transducing some cells with a viral particle comprising the GBA nucleotide sequence, and some cells with a particle comprising the reference sequence. The cells may be cultured under conditions suitable for expressing the GCase protein or fragment thereof encoded by the GBA nucleotide sequence, and the level of expressed GCase protein can be compared. The level of expressed GCase protein can be assessed using a fluorometric assay as described in the section entitled "GCase protein or fragment thereof", or an ELISA using a GCase-specific antibody. Suitable cells include cultured human liver cells, such as Huh-7 cells.

As discussed above, the presence of CpGs (i.e. CG dinucleotides) may reduce expression efficiency. This is because CpGs may be methylated, and their methylation may lead to gene silencing thereby reducing expression. Also, it is possible that high CpG content could trigger a TLR response, increasing the risk of an anti-AAV immune response. For this reason, it is preferred that the portion of the coding sequence that is codon-optimised comprises a reduced number of CpGs compared to a corresponding portion of a reference wild type GBA nucleotide sequence (such as SEQ ID NO: 9). In an embodiment, the portion of the GBA nucleotide sequence that is codon-optimised (which may be all of the GBA nucleotide sequence) comprises less than 40, less than 20, less than 10, or less than 5 CpGs. In an embodiment, the portion of the GBA nucleotide sequence that is codon-optimised (which may be all of the GBA nucleotide sequence) comprises less than 5, less than 4, less than 3, or less than 2 CpGs per 100 nts. In some embodiments, the portion of the coding sequence that is codon-optimised is CpG-free, i.e. contains no (0) CG dinucleotides.

In an embodiment, the portion of the GBA nucleotide sequence that is codon-optimised is at least 80%, at least 85%, at least 90%, at least 95%, at least 98%, at least 99%, at least 99.5%, at least 99.8%, or 100% identical to a fragment of at least 1000, at least 1200, at least 1300, less than 1494, between 1000 and 1494, between 1300 and 1494, or around 1494 nucleotides of SEQ ID NO: 1-4. In an embodiment, the portion of the coding sequence that is codon-optimised is at least 80%, at least 85%, at least 90%, at least 95%, at least 98%, at least 99%, at least 99.5%, at least 99.8%, or 100% identical to SEQ ID NO: 1-4. In an embodiment, the portion of the GBA nucleotide sequence that is codon-optimised is at least 80%, at least 85%, at least 90%, at least 95%, at least 98%, at least 99%, at least 99.5%, at least 99.8%, or 100% identical to a fragment of at least 1000, at least 1200, at least 1300, less than 1494, between 1000 and 1494, between 1300 and 1494, or around 1494 nucleotides of SEQ ID NO: 1. In an embodiment, the portion of the GBA nucleotide sequence that is codon-optimised is at least 99.5%, at least 99.8%, or 100% identical to a fragment of at least 1300 nucleotides of SEQ ID NO: 1. In an embodiment, the portion of the coding sequence that is codon-optimised is at least 80%, at least 85%, at least 90%, at least 95%, at least 98%, at least 99%, at least 99.5%, at least 99.8%, or 100% identical to SEQ ID NO: 1.

The present invention provides a polynucleotide comprising a GBA nucleotide sequence that encodes a GCase protein or a fragment thereof and the GBA sequence comprises a sequence that is at least 95%, at least 98%, at least 99%, at least 99.5%, at least 99.8%, or 100% identical to SEQ ID NO: 1. Optionally, the sequence that is at least 95%, at least 98%, at least 99%, at least 99.5%, or at least 99.8% identical to SEQ ID NO: 1 is codon-optimised.

Portion of the Coding Sequence that is not Codon-Optimised

In an embodiment, the GBA nucleotide sequence comprises a portion that is not codon-optimised. The portion that is not codon-optimised may be a contiguous portion.

As would be understood in the art, the portion that is not codon-optimised is therefore not modified to include a greater number of favoured codons compared to the wild type sequence. A contiguous non-codon-optimised polynucleotide sequence is a wild type sequence.

Optionally, the portion that is not codon-optimised is at least 80, at least 90, at least 100, at least 110, less than 200, less than 170, less than 140, or around 117 nucleotides. In some embodiments, the portion that is not codon-optimised in a GBA nucleotide sequence is the portion which encodes (corresponds to) all or a portion of the signal peptide. Optionally, the portion that is not codon-optimised encodes all or a portion of a GCase signal peptide. In some embodiments, the portion that is not codon-optimised in a GBA nucleotide sequence is a portion having a sequence of SEQ ID NO: 17.

The Polynucleotide May Further Comprise a Transcription Regulatory Element

The polynucleotide may comprise a transcription regulatory element.

In one embodiment, the transcription regulatory element is at least 80%, at least 85%, at least 90%, at least 95%, at least 98%, at least 99%, at least 99.5%, at least 99.8%, or 100% identical to SEQ ID NO: 10. In an embodiment, the polynucleotide comprises a transcription regulatory element that is at least 98%, at least 99%, at least 99.5%, at least 99.8%, or 100% identical to SEQ ID NO: 10. Optionally, the polynucleotide comprises a transcription regulatory element at least 98% identical to SEQ ID NO: 10. Optionally, the polynucleotide comprises a transcription regulatory element of SEQ ID NO: 10. Optionally, the polynucleotide comprises a transcription regulatory element consisting of SEQ ID NO: 10.

In another embodiment, the transcription regulatory element is at least 80%, at least 85%, at least 90%, at least 95%, at least 98%, at least 99%, at least 99.5%, at least 99.8%, or 100% identical to SEQ ID NO: 14. In an embodiment, the polynucleotide comprises a transcription regulatory element that is at least 98%, at least 99%, at least 99.5%, at least 99.8%, or 100% identical to SEQ ID NO: 14. Optionally, the polynucleotide comprises a transcription regulatory element at least 98% identical to SEQ ID NO: 14. Optionally, the polynucleotide comprises a transcription regulatory element of SEQ ID NO: 14. Optionally, the polynucleotide comprises a transcription regulatory element consisting of SEQ ID NO: 14.

Any appropriate transcription regulatory element may be used, such as HLP2, HLP1, LP1, HCR-hAAT, ApoE-hAAT, and LSP, which are all liver-specific transcription regulatory elements. These transcription regulatory elements are described in more detail in the following references: HLP1: McIntosh J. et al., Blood 2013 Apr. 25, 121 (17): 3335-44;

LP1: Nathwani et al., Blood. 2006 Apr. 1, 107 (7): 2653-2661; HCR-hAAT: Miao et al., Mol Ther. 2000; 1:522-532; ApoE-hAAT: Okuyama et al., Human Gene Therapy, 7, 637-645 (1996); and LSP: Wang et al., Proc Natl Acad Sci USA. 1999 Mar. 30, 96 (7): 3906-3910.

The transcription regulatory element may comprise a promoter and/or an enhancer, such as the promoter element and/or enhancer element from HLP2, HLP1, LP1, HCR-hAAT, ApoE-hAAT, and LSP. Each of these transcription regulatory elements comprises a promoter, an enhancer, and optionally other nucleotides.

In an embodiment, the transcription regulatory element comprises an enhancer which is the human apolipoprotein E (ApoE) hepatic locus control region (HCR; Miao et al (2000), Molecular Therapy 1 (6): 522), or a fragment thereof. In an embodiment, the transcription regulatory element comprises a fragment of the HCR enhancer which is a fragment of at least 80, at least 90, at least 100, less than 192, between 80 and 192, between 90 and 192, between 100 and 250, or between 117 and 192 nucleotides in length. Optionally, the fragment of the HCR enhancer is between 100 and 250 nucleotides in length. In another embodiment, the fragment of an HCR enhancer is a fragment of at least 150, at least 190, at least 230, less than 400, between 150 and 400, between 190 and 370, between 230 and 340, between 250 and 340, or around 321 nucleotides in length. Optionally, the fragment of the HCR enhancer is between 250 and 340 nucleotides in length.

Suitable HCR enhancer element fragment are described in SEQ ID NOs: 11 and 16. Optionally, the transcription regulatory element comprises an enhancer that is at least 80, at least 90, at least 100, less than 192, between 80 and 192, between 90 and 192, between 100 and 250, or between 117 and 192 nucleotides in length and the enhancer comprises a polynucleotide sequence that is at least 80%, at least 85%, at least 90%, at least 95%, at least 98%, at least 99%, at least 99.5%, at least 99.8%, or 100% identical SEQ ID NO: 11. Optionally, the transcription regulatory element comprises an enhancer that is between 117 and 192 nucleotides in length and the enhancer comprises a polynucleotide sequence that is at least 98%, at least 99%, at least 99.5%, at least 99.8%, or 100% identical SEQ ID NO. 11. Optionally, the transcription regulatory element comprises an enhancer that is at least 80%, at least 85%, at least 90%, at least 95%, at least 98%, at least 99%, at least 99.5%, at least 99.8%, or 100% identical to a fragment of at least 90, at least 100, or at least 110 nucleotides of SEQ ID NO: 11. Optionally, the polynucleotide comprises an enhancer that is at least 80%, at least 85%, at least 90%, at least 95% at least 98%, at least 99%, at least 99.5%, at least 99.8%, or 100% identical to SEQ ID NO: 11. Optionally, the polynucleotide comprises an enhancer that is at least 98%, at least 99%, at least 99.5%, at least 99.8%, or 100% identical to SEQ ID NO: 11. Optionally, the polynucleotide comprises an enhancer of SEQ ID NO: 11. Optionally, the transcription regulatory element comprises a fragment of an HCR enhancer that is equal to or less than 321 nucleotides, equal to or less than 192 nucleotides or equal to or less than 117 nucleotides in length and comprises SEQ ID NO: 11.

In another embodiment, the transcription regulatory element comprises an enhancer that is at least 150, at least 190, at least 230, less than 400, between 150 and 400, between 190 and 370, between 230 and 340, between 250 and 340, or around 318 nucleotides in length and the enhancer comprises a polynucleotide sequence that is at least 80%, at least 85%, at least 90%, at least 95%, at least 98%, at least 99%, at least 99.5%, at least 99.8%, or 100% identical SEQ ID NO: 16. Optionally, the transcription regulatory element comprises an enhancer that is between 250 and 340 nucleotides in length and the enhancer comprises a polynucleotide sequence that is at least 98%, at least 99%, at least 99.5%, at least 99.8%, or 100% identical SEQ ID NO: 16. Optionally, the transcription regulatory element comprises an enhancer that is at least 80%, at least 85%, at least 90%, at least 95%, at least 98%, at least 99%, at least 99.5%, at least 99.8%, or 100% identical to a fragment of at least 250 nucleotides of SEQ ID NO: 16. Optionally, the polynucleotide comprises an enhancer that is at least 80%, at least 85%, at least 90%, at least 95% at least 98%, at least 99%, at least 99.5%, at least 99.8%, or 100% identical to SEQ ID NO: 16. Optionally, the polynucleotide comprises an enhancer that is at least 98%, at least 99%, at least 99.5%, at least 99.8%, or 100% identical to SEQ ID NO: 16. Optionally, the polynucleotide comprises an enhancer of SEQ ID NO: 16.

In an embodiment, the transcription regulatory element comprises a promoter which is a human alpha-1 anti-trypsin promoter (A1AT; Miao et al (2000), Molecular Therapy 1(6):522), or a fragment thereof. Optionally, a fragment of an A1AT promoter which is at least 100, at least 120, at least 150, at least 180, less than 255, between 100 and 255, between 150 and 225, between 150 and 300, or between 180 and 255 nucleotides in length. Optionally, the fragment of an A1AT promoter is between 150 and 300 nucleotides in length. In another embodiment, a fragment of an A1AT promoter which at least 200, at least 250, at least 300, less than 500, between 200 and 500, between 250 and 500, or between 350 and 450 nucleotides in length. Optionally, the fragment of an A1AT promoter is between 350 and 450 nucleotides in length.

Suitable A1AT promoter fragments are described in SEQ ID NOs: 12 and 15. Optionally, the transcription regulatory element comprises a promoter that is at least 100, at least 120, at least 150, at least 180, less than 255, between 100 and 255, between 150 and 300, or between 180 and 255 nucleotides in length and the promoter comprises a polynucleotide sequence that is at least 80%, at least 85%, at least 90%, at least 95%, at least 98%, at least 99%, at least 99.5%, at least 99.8%, or 100% identical to SEQ ID NO: 12. Optionally, the transcription regulatory element comprises a promoter that is between 180 and 255 nucleotides in length and the promoter comprises a polynucleotide sequence that is at least 98%, at least 99%, at least 99.5%, at least 99.8%, or 100% identical to SEQ ID NO: 12. Optionally, the polynucleotide comprises a promoter that is at least 80%, at least 85%, at least 90%, at least 95%, at least 98%, at least 99%, at least 99.5%, at least 99.8%, or 100% identical to a fragment of at least 100, at least 120, or at least 150 nucleotides of SEQ ID NO: 12. Optionally, the polynucleotide comprises a promoter that is at least 80%, at least 85%, at least 90%, at least 95%, at least 98%, at least 99%, at least 99.5%, at least 99.8%, or 100% identical to SEQ ID NO: 12. Optionally, the polynucleotide comprises a promoter that is at least 98%, at least 99%, at least 99.5%, at least 99.8%, or 100% identical to SEQ ID NO: 12. Optionally, the polynucleotide comprises a promoter of SEQ ID NO: 12. Optionally, the transcription regulatory element comprises a fragment of an A1AT promoter that is equal to or less than 418 nucleotides, equal to or less than 255 nucleotides or equal to or less than 185 nucleotides in length and comprises SEQ ID NO: 12.

In another embodiment, the transcription regulatory element comprises a promoter that is at least 200, at least 250, at least 300, less than 500, between 200 and 500, between 250 and 500, between 350 and 450, or around 418 nucleotides in length and the promoter comprises a polynucleotide sequence that is at least 80%, at least 85%, at least 90%, at least 95%, at least 98%, at least 99%, at least 99.5%, at least 99.8%, or 100% identical to SEQ ID NO: 15. Optionally, the transcription regulatory element comprises a promoter that is between 350 and 450 nucleotides in length and the promoter comprises a polynucleotide sequence that is at least 98%, at least 99%, at least 99.5%, at least 99.8%, or 100% identical to SEQ ID NO: 15. Optionally, the polynucleotide comprises a promoter that is at least 80%, at least 85%, at least 90%, at least 95%, at least 98%, at least 99%, at least 99.5%, at least 99.8%, or 100% identical to a fragment of at least 350 nucleotides of SEQ ID NO: 15. Optionally, the polynucleotide comprises a promoter that is at least 80%, at least 85%, at least 90%, at least 95%, at least 98%, at least 99%, at least 99.5%, at least 99.8%, or 100% identical to SEQ ID NO: 15. Optionally, the polynucleotide comprises a promoter that is at least 98%, at least 99%, at least 99.5%, at least 99.8%, or 100% identical to SEQ ID NO: 15. Optionally, the polynucleotide comprises a promoter of SEQ ID NO: 15.

If the polynucleotide is intended for expression in the liver, the promoter may be a liver-specific promoter. Optionally, the promoter is a human liver-specific promoter. A "liver-specific promoter" is a promoter that provides a higher level of expression in liver cells compared to other cells in general. For example, the skilled person can determine whether a promoter is a liver-specific promoter by comparing expression of the polynucleotide in liver cells (such as Huh-7 cells) with expression of the polynucleotide in cells from other tissues. If the level of expression is higher in the liver cells, compared to the cells from other tissues, the promoter is a liver-specific promoter. Optionally, the transcription regulatory element or the promoter is liver-specific if it promotes protein expression at higher levels in liver cells compared to cells from at least one other organ or tissue and the transcription regulatory element or the promoter promotes protein expression in the cells from at least one other organ or tissue at a level less than 40%, less than 30%, less than 25%, less than 15%, less than 10%, or less than 5% of the level that the transcription regulatory element or the promoter promotes protein expression in liver cells. Optionally, the cells from at least one other organ or tissue are at least one of kidney cells, pancreatic cells, breast cells, neuroblastoma cells, lung cells, and early B cells. Optionally, the cells from at least one other organ or tissue are kidney cells, pancreatic cells, breast cells, neuroblastoma cells, lung cells, and early B cells. Optionally, the cells from at least one other organ or tissue are at least one of HEK293T cells, PANCI cells, BxPC-3 cells, MCF7 cells, 1643 cells, MRC-9 cells, and 697 cells. Optionally, the cells from at least one other organ or tissue are HEK293T cells, PANCI cells, BxPC-3 cells, MCF7 cells, 1643 cells, MRC-9 cells, and 697 cells.

In one embodiment, the polynucleotide of the invention may provide for GCase to be specifically expressed in the liver. In such examples, the polynucleotide may promote substantially more GCase expression in liver cells than in at least one other tissue type or organ. In one example, the polynucleotide of the invention which provides for GCase to be specifically expressed in the liver comprises a liver-specific promoter.

Optionally, the polynucleotide of the invention may provide for GCase to be expressed at higher levels in liver cells compared to cells from at least one other organ or tissue and such that GCase is expressed in the one other organ or tissue at a level less than 40%, less than 30%, less than 25%, less than 15%, less than 10%, or less than 5% of the level of GCase expression in liver cells, when measured in the same assay.

Optionally, the cells from at least one other organ or tissue are at least one of kidney cells, pancreatic cells, breast cells, neuroblastoma cells, lung cells, and early B cells. Optionally, the cells from at least one other organ or tissue are kidney cells, pancreatic cells, breast cells, neuroblastoma cells, lung cells, and early B cells. Optionally, the cells from at least one other organ or tissue are at least one of HEK293T cells, PANCI cells, BxPC-3 cells, MCF7 cells, 1643 cells, MRC-9 cells, and 697 cells. Optionally, the cells from at least one other organ or tissue are HEK293T cells, PANCI cells, BxPC-3 cells, MCF7 cells, 1643 cells, MRC-9 cells, and 697 cells.

A Viral Particle Comprising the Polynucleotide

The invention further provides a viral particle comprising a recombinant genome comprising polynucleotides of the invention. For the purposes of the present invention, the term "viral particle" refers to all or part of a virion. For example, the viral particle comprises a recombinant genome and may further comprise a capsid. The viral particle may be a gene therapy vector. Herein, the terms "viral particle" and "vector" are used interchangeably. For the purpose of the present application, a "gene therapy" vector is a viral particle that can be used in gene therapy, i.e. a viral particle that comprises all the required functional elements to express a transgene, such as a GBA nucleotide sequence, in a host cell after administration.

Suitable viral particles include a parvovirus, a retrovirus, a lentivirus or a herpes simplex virus. The parvovirus may be an adeno-associated virus (AAV). The viral particle is preferably a recombinant adeno-associated viral (AAV) vector or a lentiviral vector. More preferably, the viral particle is an AAV viral particle. The terms AAV and rAAV are used interchangeably herein, unless context obviously suggests otherwise.

The genomic organization of all known AAV serotypes is very similar. The genome of AAV is a linear, single-stranded DNA molecule that is less than about 5,000 nucleotides in length. Inverted terminal repeats (ITRs) flank the unique coding nucleotide sequences for the non-structural replication (Rep) proteins and the structural (VP) proteins. The VP proteins (VP1, -2 and -3) form the capsid. The terminal ~145 nt (ITRs) are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

The recombinant viral genome of the invention may comprise ITRs. It is possible for an AAV vector of the invention to function with only one ITR. Thus, the viral genome comprises at least one ITR, but, more typically, two ITRs (generally with one either end of the viral genome, i.e. one at the 5' end and one at the 3' end). There may be intervening sequences between the polynucleotide of the invention and one or more of the ITRs. The polynucleotide may be incorporated into a viral particle located between two regular ITRs or located on either side of an ITR engineered with two D regions.

AAV sequences that may be used in the present invention for the production of AAV vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716; Chiorini et al, 1997; Srivastava et al, 1983; Chiorini et al, 1999; Rutledge et al, 1998; and Wu et al, 2000. AAV serotype 1, 2, 3, 3B, 4, 5, 6, 7, 8, 9, 10, 11 or 12 may be used in the present invention. The sequences from the AAV serotypes may be mutated or engineered when being used in the production of gene therapy vectors.

Optionally, an AAV vector comprises ITR sequences which are derived from AAV1, AAV2, AAV4 and/or AAV6. Preferably the ITR sequences are AAV2 ITR sequences. Herein, the term AAVx/y refers to a viral particle that comprises genomic components such as at least ITRs from AAVx (wherein x is a AAV serotype number) and has the capsid from AAVy (wherein y is the number of the same or different serotype). For example, an AAV2/8 vector may comprise a portion of a viral genome, including the ITRs, from an AAV2 strain, and a capsid from an AAV8 strain.

In an embodiment, the viral particle is an AAV viral particle comprising a capsid. AAV capsids are generally formed from three proteins, VP1, VP2 and VP3. The amino acid sequence of VP1 comprises the sequence of VP2. The portion of VP1 which does not form part of VP2 is referred to as VP1unique or VP1U. The amino acid sequence of VP2 comprises the sequence of VP3. The portion of VP2 which does not form part of VP3 is referred to as VP2unique or VP2U. Optionally, the viral particle comprises a liver-tropic or CNS-tropic capsid. Whether a viral particle (capsid) is tropic for a particular tissue can be evaluated for example by administering such a particle expressing a marker gene such as luciferase and imaging in vivo at multiple time points (for example as described in Zincarelli et al (2008), Molecular Therapy, 16:1073-1080). A particle driving strong marker expression in liver or CNS tissues, respectively, especially if in contrast to lesser expression in other tissues, would be considered liver-or CNS-tropic.

In some embodiments, a liver-tropic capsid can be an AAV3-or AAV3B-derived capsid. Optionally, the liver-tropic capsid comprises a sequence at least 98%, at least 99%, or at least 99.5% identical to a fragment of at least 600, at least 650, at least 700, between 600 and 736, between 650 and 736 or between 700 and 736 amino acids of SEQ ID NO: 19, 20, or 24. Optionally, the liver-tropic capsid comprises a sequence at least 99% identical to SEQ ID NO: 19. Optionally, the liver-tropic capsid comprises a sequence at least 99% identical to SEQ ID NO: 20. Optionally, the liver-tropic capsid comprises a sequence at least 99% identical to SEQ ID NO: 24. Optionally, the CNS tropic capsid comprises a sequence at least 98%, at least 99%, at least 99.5% identical to a fragment of at least 600, at least 650, at least 700, between 600 and 736, between 650 and 736 or between 700 and 736 amino acids of SEQ ID NO: 21. Optionally, the CNS-tropic capsid comprises a sequence at least 99% identical to SEQ ID NO: 21. A viral particle of the invention may be a "hybrid" particle in which the viral ITRs and viral capsid are from different parvoviruses, such as different AAV serotypes. Preferably, the viral ITRs and capsid are from different serotypes of AAV, in which case such viral particles are known as transcapsidated or pseudotyped. Likewise, the parvovirus may have a "chimeric" capsid (e.g., containing sequences from different parvoviruses, preferably different AAV serotypes) or a "targeted" capsid (e.g., a directed tropism).

In some embodiments, the recombinant AAV genome comprises intact ITRs, comprising functional terminal resolution sites (TRS). Such an AAV genome may contain one or two resolvable ITRs, i.e. ITRs containing a functional TRS at which site-specific nicking can take place to create a free 3' hydroxyl group which can serve as a substrate for DNA polymerase to unwind and copy the ITR. Preferably, the recombinant genome is single-stranded (i.e., it is packaged into the viral particle in a single-stranded form). Optionally, the recombinant genome is not packaged in self-complementary configuration, i.e. the genome does not comprise a single covalently-linked polynucleotide strand with substantial self-complementary portions that anneal in the viral particle. Alternatively, the recombinant genome may be packaged in "monomeric duplex" form. "Monomeric duplexes" are described in WO 2011/122950. The genome may be packaged as two substantially complementary but non-covalently linked polynucleotides which anneal in the viral particle.

The viral particle may further comprise a poly A sequence. The poly A sequence may be positioned downstream of the nucleotide sequence encoding a functional GCase protein. The poly A sequence may be a bovine growth hormone poly A sequence (bGHpA-SEQ ID NO: 23). The poly A sequence may be between 250 and 270 nucleotides in length.

The viral particle may further comprise an intron sequence, such as a viral intron sequence, optionally an SV40 intron sequence (SEQ ID NO: 22).

In one embodiment, the viral particle comprises a polynucleotide sequence comprising a promoter element, an intron sequence, such as an SV40 intron sequence, a GBA nucleotide sequence, and a poly A sequence, such as the bGHpA sequence. In such embodiments, the intron sequence, such as the SV40 intron sequence, may be located between the promoter element and the GBA nucleotide sequence. In such embodiments, the poly A sequence, such as the bGHpA sequence, may be located downstream of the GBA nucleotide sequence.

The viral particle of the invention optionally expresses GCase highly in host cells. For example, on transduction in Huh-7 cells, the viral particle of the present invention expresses GCase protein or a fragment thereof at a higher level compared to an otherwise identical viral particle comprising a GBA nucleotide sequence of SEQ ID NO: 9 transduced at a comparable amount into a comparable population of Huh-7 cells. Optionally, after transduction into a population of Huh-7 cells, the viral particle of the present invention expresses GCase protein at a higher level than a viral particle comprising a GBA nucleotide sequence of SEQ ID NO: 9 and a transcription regulatory element of SEQ ID NO: 10 or a promoter of SEQ ID NO: 12. Optionally, after transduction into a population of Huh-7 cells, the viral particle of the present invention expresses GCase protein at a higher level than a comparable viral particle comprising a GBA nucleotide sequence of SEQ ID NO: 9 and a transcription regulatory element of SEQ ID NO: 10 or a promoter sequence of SEQ ID NO: 12 transduced at a comparable amount into a comparable population of Huh-7 cells. Optionally, after transduction into a population of Huh-7 cells, the viral particle expresses GCase protein at comparable level (i.e. a non-statistically significantly different level) to a viral particle comprising a GBA nucleotide sequence of SEQ ID NO: 9 and a promoter element of SEQ ID NO: 13 transduced at a comparable amount into a comparable population of Huh-7 cells. In such embodiments, the term "comparable viral particle" refers to a viral particle that is the same as an AAV viral particle of the invention, except the comparable viral particle comprises a different GBA nucleotide sequence and a different transcription regulatory element. Optionally, the comparable viral particle comprises the same transcription regulatory element as the AAV viral particle of the invention. Optionally, the activity is assessed using a chromogenic assay such as the fluorometric assay discussed above.

In one embodiment, provided is a viral particle comprising a polynucleotide sequence, the polynucleotide sequence comprising:
    a) a GBA nucleotide sequence having at least 98% sequence identity to SEQ ID NO: 5, operably linked to:
    b) a transcriptional regulatory sequence having at least 98% sequence identity to SEQ ID NO: 14;
wherein the viral particle further comprises a capsid having at least 98% identity to SEQ ID NO: 20.

In one embodiment, provided is a viral particle comprising a polynucleotide sequence, the polynucleotide sequence comprising:
    a) a GBA nucleotide sequence having at least 98% sequence identity to SEQ ID NO: 5, operably linked to:
    b) a transcriptional regulatory sequence having at least 98% sequence identity to SEQ ID NO: 10;
wherein the viral particle further comprises a capsid having at least 98% identity to SEQ ID NO: 20.

Compositions, Methods and Uses

In a further aspect of the invention, there is provided a composition comprising the polynucleotide or vector/viral particle of the invention and a pharmaceutically acceptable excipient.

The pharmaceutically acceptable excipients may comprise carriers, diluents and/or other medicinal agents, pharmaceutical agents or adjuvants, etc. Optionally, the pharmaceutically acceptable excipients comprise saline solution. Optionally, the pharmaceutically acceptable excipients comprise human serum albumin.

This invention further provides a method of expressing the GBA nucleotide sequence and achieving a stable GCase activity in a subject and/or providing greater GCase bioavailability in a subject compared to the bioavailability from GCase enzyme replacement therapy, wherein the bioavailability is measured over a period of 2 weeks from administration, wherein the method comprises administration of a polynucleotide, viral particle or composition of the invention to a subject.

The invention further provides a polynucleotide, vector/viral particle or composition of the invention for use in a method of treatment. Optionally the method of treatment comprises administering an effective amount of the polynucleotide or vector/viral particle of the invention to a patient.

The invention further provides a method of treatment comprising administering an effective amount of the polynucleotide or vector/viral particle of the invention to a patient.

The invention further provides use of the polynucleotide, vector/viral particle or composition of the invention in the manufacture of a medicament for use in a method of treatment. Optionally the method of treatment comprises administering an effective amount of the polynucleotide or vector/viral particle of the invention to a patient. Optionally the method of treatment is a gene therapy. A "gene therapy" involves administering a vector/viral particle of the invention that is capable of expressing a transgene (such as a GBA nucleotide sequence) in the host to which it is administered.

Optionally, the method of treatment is a method of treating diseases associated with a GCase deficiency. As discussed above, GCase deficiency may lead to accumulation of glucocerebrosides in macrophages that infiltrate many vital organs which can cause a variety of diseases including synucleopathies (as discussed in WO08/144591) or Parkinson's disease. Optionally, the method of treatment is a method of treating Parkinson's disease or a synucleopathy.

Optionally, the method of treatment is a method of treating a lysosomal storage disorder such as Gaucher disease (GD), for example GD type I, type II or type III. Preferably, the lysosomal storage disorder is characterised by bruising, fatigue, anemia, low blood platelet count and enlargement of the liver and spleen. Optionally, the method of treatment is a method of treating GD, for example GD type I. In some embodiments, the patient is a patient suffering from GD, for example GD type I. Optionally the patient has antibodies or inhibitors to recombinant GCase (for example imiglucerase (Cerezyme®), velaglucerase alfa (VPRIV®) or taliglucerase alfa (ELELYSO®)) with which the patient has previously been treated as part of an enzyme replacement therapy. Optionally, the polynucleotide and/or vector/viral particle is administered intravenously. Optionally, the polynucleotide and/or vector/viral particle is for administration only once (i.e. a single dose) to a patient.

When GD is "treated" in the above method, this means that one or more symptoms of GD type I are ameliorated. It does not mean that the symptoms of GD type I are completely remedied so that they are no longer present in the patient, although in some methods, this may be the case. Thus, in all instances the term "treatment" can be replaced with the term "amelioration". The method of treatment may result in one or more of the symptoms of GD type I being less severe than before treatment. Optionally, relative to the situation pre-administration, the method of treatment results in an increase in the amount/concentration of circulating GCase in the blood of the patient, and/or the overall level of GCase activity detectable within a given volume of blood and/or the macrophages of the patient. In one embodiment, relative to the situation pre-administration, the method of treatment results in one or more of: an increase in haemoglobin concentration; an increase in platelet count; a decrease in spleen size; a decrease in liver size.

In addition, the methods of the invention may "prevent" diseases such as Gaucher disease. Gaucher disease is generally associated with an accumulation of glucocerebrosidases in various tissues, and if the methods of the invention are carried out on young subjects (such as teenagers, young adults, children or babies) it should be possible to prevent Gaucher disease from establishing. Accordingly, in all instances the term "treatment" may be replaced with the term "prevention".

A "therapeutically effective amount" refers to an amount effective, at dosages and for periods of time necessary, to achieve the desired therapeutic result, such as raising the level of functional GCase in a subject (so as to lead to functional GCase production at a level sufficient to ameliorate the symptoms of GD, for example GD type I).

Optionally, the vector/viral particle is administered at a dose of less than $1 \times 10^{11}$, less than $1 \times 10^{12}$, less than $5 \times 10^{12}$, less than $2 \times 10^{12}$, less than $1.5 \times 10^{12}$, less than $3 \times 10^{12}$, less than $1 \times 10^{13}$, less than $2 \times 10^{13}$, or less than $3 \times 10^{13}$ vector genomes per kg of weight of patient. Optionally, the dose of vector/viral particle that is administered is selected such that the subject expresses GCase at an level of 10%-90%, 20%-80%, 30%-70%, 25%-50%, 20%-150%, 30%-140%, 40%-130%, 50%-120%, 60%-110% or 70%-100% of the level of a healthy subject who does not suffer from GD.

Optionally, a patient administered the polynucleotide, viral particle or composition may have a GCase activity level of at least 1, at least 2, at least 3, at least 4, at least 5, at least 6, at least 7, at least 8, or at least 9 µmol/h/ml. Optionally, the GCase activity is measured using a fluorometric substrate which is specific for GCase. Optionally, the GCase activity is measured fluorometrically with 4-Methylumbelliferyl-β-D-glucopyranoside (4MU-Glc) as a substrate. Optionally, the GCase activity is measured in the serum, plasma, macrophages, spleen, liver and/or bone marrow of the subject.

In one embodiment, GCase activity may be determined fluorometrically with 4-Methylumbelliferyl-β-D-glucopyranoside (4MU-Glc) as a substrate as follows: (1) serum samples are collected or tissues (liver, spleen, bone marrow) are harvested and snap frozen and lysed; (2) the tissue lysate or serum/plasma sample are mixed in 50 mM Sodium Citrate, 25 mM Taurocholate, pH=5.75, 6 mM 4MU-Glc, for 30 min at 37° C.; (3) the reaction is stopped by adding one volume (100 µl) of stop solution (0.5 M Glycine, 0.3 M NaOH, pH 10.0); (4) relative fluorescence levels (RFU) are evaluated with a Spectramax® I3X (Molecular devices) microplate reader using excitation and emission wavelengths of 365 nm and 445 nm, respectively and fluorescence levels were then converted to nanomoles/h/mL based on a 4-Methylumbelliferone (4-MU, Sigma-Aldrich) standard curve.

Optionally, a patient administered the polynucleotide, viral particle or composition may have a greater GCase activity level at least 5, at least 10, at least 15, at least 20, at least 25, at least 30, or at least 35 weeks after administration when compared to the activity measured in a subject administered an effective dose of a GCase enzyme replacement therapy, when measured in the same assay at the same time point after administration. Optionally, a patient administered the polynucleotide, viral particle or composition may have a GCase activity level greater by 10 fold, 20 fold, 50 fold, 100 fold or 1000 fold at least 5, at least 10, at least 15, at least 20, at least 25, at least 30, or at least 35 weeks after administration when compared to the activity measured in a subject administered an effective dose of a GCase enzyme replacement therapy, when measured in the same assay at the same time point after administration.

Optionally, the dose of vector/viral particle that is administered is selected such that there is a greater GCase bioavailability to the subject when compared to the bioavailability from GCase enzyme replacement therapy. Bioavailability may be measured (e.g. estimated or calculated) through any known method in the art. GCase bioavailability may be measured in the serum, macrophages, spleen, liver and/or bone marrow of the subject. In one example, bioavailability may be estimated using the area under the curve ("AUC") method according to Example 8. In one example, bioavailability may be estimated by estimating the total GCase activity available in the serum, plasma, macrophages, spleen, liver and/or bone marrow of the subject. Optionally, it is calculated over a defined time period, and refers to the total activity or concentration of GCase during that time period. Optionally, the GCase activity is measured using a fluorometric substrate which is specific for GCase. Optionally, the GCase activity is measured fluorometrically with 4-Methylumbelliferyl-β-D-glucopyranoside (4MU-Glc) as a substrate. Optionally, the GCase activity is measured in the serum, plasma, macrophages, spleen, liver and/or bone marrow of the subject. Optionally the GCase activity is measured in the white blood cells of the subject. Optionally, the bioavailability is measured over a period of 2 weeks from administration. Optionally, the bioavailability is measured over a period of 5 weeks from administration. Optionally, the bioavailability is measured in serum. In one example, a greater GCase bioavailability in the subject is achieved over a period of at least 5, at least 10, at least 15, at least 20, at least 25, at least 30, or at least 35 weeks after administration when compared to the bioavailability measured in a subject administered an effective dose of a GCase enzyme replacement therapy, when measured in the same assay at the same time point after administration.

Optionally, a patient (for example, a patient suffering from a disease or condition associated with GCase deficiency) administered the polynucleotide, viral particle or composition of the invention may have reduced hexosylceramide and/or hexosylsphingosine levels after administration, preferably when the hexosylceramide and/or hexosylsphingosine levels are measured 6 weeks, 8 weeks, 10 weeks or 12 weeks after administration. The hexosylceramide and/or hexosylsphingosine levels may be reduced by 2 times or more, 3 times or more, 4 times or more, 5 times or more, 6 times or more, 2 to 3 times, 2 to 4 times, 2 to 5 times, 2 to 6 times, or 3 to 5 times when compared to the (starting) hexosylceramide and/or hexosylsphingosine levels at the time of administration of the polynucleotide, viral particle or composition of the invention. For example, after administration of the polynucleotide viral particle or composition of the invention (for example 6 weeks, 8 weeks, 10 weeks or 12 weeks after administration), the hexosylceramide and/or hexosylsphingosine levels in the patient may be 50% or less, 40% or less, 30% or less, 25% or less, 20% or less when compared to the (starting) hexosylceramide and/or hexosylsphingosine levels at the time of administration of the polynucleotide, viral particle or composition of the invention. Optionally, the patient may have increased hexosylceramide and/or hexosylsphingosine levels when compared to a healthy subject or a subject who does not have a disease or condition associated with GCase deficiency. For example, the hexosylceramide and/or hexosylsphingosine levels are measured in the spleen, liver and/or bone marrow of the patient/subject. The hexosylceramide and/or hexosylsphingosine levels may be measured in the serum and/or white blood cells (e.g. macrophages) of the patient/subject. Methods of measuring hexosylceramide and/or hexosylsphingosine levels are known in the art, and the levels of hexosylceramide and/or hexosylsphingosine are preferably measured using mass spectrometry (LC/MS analysis), for example by the method described in example 9. Optionally, the reduction of hexosylceramide and/or hexosylsphingosine levels (for example in the serum, white blood cells (e.g. macrophages), spleen, liver and/or bone marrow of the patient/subject) are greater than the reduction achieved from GCase enzyme replacement therapy, preferably when the hexosylceramide and/or hexosylsphingosine levels are measured after at least 6 weeks, at least 8 weeks, at least 10 weeks or at least 12 weeks after the start of treatment. For example levels after at least 6 weeks (e.g. at 6 weeks), at least 8 weeks (e.g. at 8 weeks), at least 10 weeks (e.g. at 10 weeks) or at least 12 weeks (e.g. at 12 weeks) from administration of the polynucleotide, viral particle or composition of the invention may be compared to levels after at least 6 weeks (e.g. at 6 weeks), at least 8 weeks (e.g. at 8 weeks), at least 10 weeks (e.g. at 10 weeks) or at least 12 weeks (e.g. at 12 weeks), respectively, from the first administration of GCase enzyme replacement therapy. As a particular example, hexosylceramide and/or hexosylsphingosine levels may be measured after at least 12 weeks (e.g. at 12 weeks) after administration of the polynucleotide, viral particle or composition of the invention and compared to the levels measured at least 12 weeks (e.g. at 12 weeks) after first administration of GCase enzyme replacement therapy. Preferably, the levels of hexosylceramide and/or hexosylsphingosine are measured in the same assay at the same time point after administration. Optionally, the GCase enzyme replacement therapy may be administered every two weeks. Optionally, the reduction of hexosylceramide levels in the subject (or patient) after administration of the polynucleotide, viral particle or composition of the invention are such that the hexosylceramide levels (for example in the serum, white blood cells (e.g. macrophages), liver and/or spleen) are no more than 200%, 150%, or 125% of the hexosylceramide levels measured in a healthy subject or a subject not suffering from a disease or condition associated with GCase deficiency. In one example, a reduction in hexosylceramide and/or hexosylsphingosine levels may represent a reduction in glucosylceramide and/or glucosylsphingosine levels, respectively. For example, a reduction in hexosylceramide may represent a reduction in glucosylceramide. As a further example, a reduction in hexosylsphingosine levels may represent a reduction in glucosylsphingosine levels.

In one example, a reduction in hexosylceramide and/or hexosylsphingosine levels is a reduction in glucosylceramide and/or glucosylsphingosine respectively. In other words, a patient (for example, a patient suffering from a disease or condition associated with GCase deficiency) administered the polynucleotide, viral particle or composition of the invention may have reduced glucosylceramide and/or glucosylsphingosine levels after administration, preferably when the glucosylceramide and/or glucosylsphingosine levels are measured 6 weeks, 8 weeks, 10 weeks or 12 weeks after administration. The glucosylceramide and/or glucosylsphingosine levels may be reduced by 2 times or more, 3 times or more, 4 times or more, 5 times or more, 6 times or more, 2 to 3 times, 2 to 4 times, 2 to 5 times, 2 to 6 times, or 3 to 5 times when compared to the (starting) glucosylceramide and/or glucosylsphingosine levels at the time of administration of the polynucleotide, viral particle or composition of the invention. For example, after administration of the polynucleotide viral particle or composition of the invention (for example 6 weeks, 8 weeks, 10 weeks or 12 weeks after administration), the glucosylceramide and/or glucosylsphingosine levels in the patient may be 50% or less, 40% or less, 30% or less, 25% or less, 20% or less when compared to the (starting) glucosylceramide and/or glucosylsphingosine levels at the time of administration of the polynucleotide, viral particle or composition of the invention. Optionally, the patient may have increased glucosylceramide and/or glucosylsphingosine levels when compared to a healthy subject or a subject who does not have a disease or condition associated with GCase deficiency. For example, the glucosylceramide and/or glucosylsphingosine levels are measured in the spleen, liver and/or bone marrow of the patient/subject. The glucosylceramide and/or glucosylsphingosine levels may be measured in the serum and/or white blood cells (e.g. macrophages) of the patient/subject. Methods of measuring glucosylceramide and/or glucosylsphingosine levels are known in the art, and the levels of glucosylceramide and/or glucosylsphingosine are preferably measured using mass spectrometry (LC/MS analysis), for example by the method described in example 9. Optionally, the reduction of glucosylceramide and/or glucosylsphingosine levels (for example in the serum, white blood cells (e.g. macrophages), spleen, liver and/or bone marrow of the patient/subject) are greater than the reduction achieved from GCase enzyme replacement therapy, preferably when the glucosylceramide and/or glucosylsphingosine levels are measured after at least 6 weeks, at least 8 weeks, at least 10 weeks or at least 12 weeks after the start of treatment. For example levels after at least 6 weeks (e.g. at 6 weeks), at least 8 weeks (e.g. at 8 weeks), at least 10 weeks (e.g. at 10 weeks) or at least 12 weeks (e.g. at 12 weeks) from administration of the polynucleotide, viral particle or composition of the invention may be compared to levels after at least 6 weeks (e.g. at 6 weeks), at least 8 weeks (e.g. at 8 weeks), at least 10 weeks (e.g. at 10 weeks) or at least 12 weeks (e.g. at 12 weeks), respectively, from the first administration of GCase enzyme replacement therapy. As a particular example, glucosylceramide and/or glucosylsphingosine levels may be measured after at least 12 weeks (e.g. at 12 weeks) after administration of the polynucleotide, viral particle or composition of the invention and compared to the levels measured at least 12 weeks (e.g. at 12 weeks) after first administration of GCase enzyme replacement therapy. Preferably, the levels of glucosylceramide and/or glucosylsphingosine are measured in the same assay at the same time point after administration. Optionally, the GCase enzyme replacement therapy may be administered every two weeks. Optionally, the reduction of glucosylceramide levels in the subject (or patient) after administration of the polynucleotide, viral particle or composition of the invention are such that the glucosylceramide levels (for example in the serum, white blood cells (e.g. macrophages), liver and/or spleen) are no more than 200%, 150%, or 125% of the glucosylceramide levels measured in a healthy subject or a subject not suffering from a disease or condition associated with GCase deficiency.

Optionally a patient (for example, a patient suffering from a disease or condition associated with GCase deficiency) administered the polynucleotide, viral particle or composition of the invention may show a reduced number of storage cells and/or activated macrophages in the liver after administration, preferably when the cells are counted after at least 6 weeks (e.g. at 6 weeks), at least 8 weeks (e.g. at 8 weeks), at least 10 weeks (e.g. at 10 weeks) or at least 12 weeks (e.g. at 12 weeks) after administration. Reduction in the number of storage cells and/or activated macrophages in the liver may be an indication of reduced inflammation and thus therapeutic benefit. The number of activated macrophages may be indicated or estimated by measuring the number of CD68$^{positive}$ cells. Identifying storage cells and CD68$^{positive}$ cells can be performed by methods known in the art, for example the methods described in example 9.

A "GCase enzyme replacement therapy" may refer to any therapy which comprises the administration of a GCase polypeptide to a subject. The GCase polypeptide may be wild type, such as a GCase polypeptide having the amino acid sequence of SEQ ID NO: 25. The GCase polypeptide may be administered at any suitable dose, optionally at a dose of between 40 and 100, between 50 and 80, between 60 and 70, or around 60 U/kg BW. The GCase polypeptide may be administered through any appropriate route, optionally administered through intravenous injection or subcutaneous injection.

A GCase activity level of at least X % (e.g. at least 20%) refers to a GCase activity level that is at least X % (e.g. 20%) of the normal GCase level range as measured from a sample of e.g. the spleen or bone marrow. The person skilled in the art would readily understand what is meant by reference to a %-of-normal GCase activity level, which is determined in routine clinical practice by e.g. comparison to a control sample from a healthy subject.

The term "stable GCase activity" or "stable GCase activity level" refers to a GCase activity level that maintains at or above a certain level for a continuous period of at least 5 weeks. In other words, the activity may fluctuate above said activity level but is still said to be stable as long as it remains above the stated minimum threshold. In some embodiments, the GCase activity level maintains at or above a certain level for a continuous period of at least 10, at least 15, at least 20, at least 30, at least 40, or at least 50 weeks. For example, a patient has a stable GCase activity level of at least 20% if the activity level maintains at at least 20% for a continuous period of at least 5 weeks. In such an example, the GCase activity level may continue to be at at least 20% following the at least 5 weeks and thus maintains at at least 20% for a cumulative continuous period of at least 10, at least 15, at least 20, at least 30 or at least 40, or at least 50 weeks. A patient has a stable GCase activity level if the GCase activity level maintains at or above a certain level for a continuous period of at least 5 weeks. Optionally, a patient administered with the polynucleotide, viral particle or composition may have a stable GCase activity level of at least 20%, at least 25%, at least 30%, at least 35%, at least 40% or at least 50% relative to the GCase activity of a healthy subject. Optionally, a patient administered with the polynucleotide, viral particle or composition may have a stable GCase activity level of at least 1, at least 2, at least 3, at least 4, at least 5, at least 6, at least 7, at least 8 or at least 9 µmol/h/ml. Optionally, the GCase activity is measured using a fluorometric substrate which is specific for GCase. Optionally, the GCase activity is measured fluorometrically with 4-Methylumbelliferyl-B-D-glucopyranoside (4MU-Glc) as a substrate. Optionally, the GCase activity is measured in the serum, macrophages, spleen, liver and/or bone marrow of the subject.

Optionally, the GCase activity level is stable after at least 5 weeks, at least 10 weeks, at least 15 weeks, at least 20 weeks, at least 30 weeks, at least 40 weeks, or at least 50 weeks from administration of the polynucleotide, viral particle or composition. For example, where a patient has a stable GCase activity level of at least 20% after at least 5 weeks from when the patient is administered with the polynucleotide, viral particle or composition, there is a GCase activity level of at least 20% that maintains at at least 20% for a continuous period of at least 5, at least 10, at least 15, at least 20, at least 30 or at least 40, or at least 50 weeks following the initial at least 5 weeks from administration.

Optionally, the GCase activity level is at or above a certain level (e.g. 20%, 25%, 30%, 35%, or 40%; and/or at least 1, at least 2, at least 3, at least 4, at least 5, at least 6, at least 7, at least 8 or at least 9 µmol/h/ml) at a time point at least 5, at least 10, at least 20, at least 30, at least 40 or at least 50 weeks after administration of the polynucleotide, viral particle or composition. For example, the GCase activity level is at or above a certain level (e.g. 20%, 25%, 30%, 35%, or 40%; and/or at least 1, at least 2, at least 3, at least 4, at least 5, at least 6, at least 7, at least 8 or at least 9 µmol/h/ml) at a time point of around 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51 or 52 weeks after administration of the polynucleotide, viral particle or composition.

The invention will now be described with reference to the following examples, which are merely illustrative and should not in any way be construed as limiting the scope of the present invention.

| Sequence Listing | |
|---|---|
| Sequence identity number | Sequence description |
| 1 | Codon-optimised GBA nucleotide sequence from FLF-PL28, without signal peptide portion |
| 2 | Codon-optimised GBA nucleotide sequence from FLF-PL21, without signal peptide portion |
| 3 | Codon-optimised GBA nucleotide sequence from FLF-PL30, without signal peptide portion |
| 4 | Codon-optimised GBA nucleotide sequence from FLF-PL36, without signal peptide portion |
| 5 | Codon-optimised GBA nucleotide sequence from FLF-PL28, with signal peptide portion |
| 6 | Codon-optimised GBA nucleotide sequence from FLF-PL21, with signal peptide portion |
| 7 | Codon-optimised GBA nucleotide sequence from FLF-PL30, with signal peptide portion |
| 8 | Codon-optimised GBA nucleotide sequence from FLF-PL36, with signal peptide portion |
| 9 | Wild type human GBA nucleotide sequence with signal peptide (from GenBank NM_000157.3) |
| 10 | LSP-S transcription regulatory element |
| 11 | HCR enhancer portion of LSP-S |
| 12 | A1AT promoter portion of LSP-S |
| 13 | CAG promoter |
| 14 | LSP-L transcription regulatory element |
| 15 | A1AT promoter portion of LSP-L |
| 16 | HCR enhancer portion of LSP-L |

| Sequence Listing | |
|---|---|
| Sequence identity number | Sequence description |
| 17 | Wild type GBA nucleotide sequence corresponding to signal peptide |
| 18 | Wild type GCase polypeptide sequence of signal peptide |
| 19 | Polypeptide sequence of liver-tropic capsid |
| 20 | Polypeptide sequence of liver-tropic capsid |
| 21 | Polypeptide sequence of CNS-tropic capsid |
| 22 | Nucleotide sequence of SV40 intron |
| 23 | Nucleotide sequence of bovine growth hormone poly A sequence |
| 24 | Polypeptide sequence of liver-tropic capsid |
| 25 | Polypeptide sequence of wild type human GCase |

ASPECTS OF THE INVENTION

The invention is further described in the following aspects.

1. A polynucleotide comprising a GBA nucleotide sequence, wherein the GBA nucleotide sequence encodes a β-Glucocerebrosidase (GCase) protein or fragment thereof and wherein at least a portion of the GBA nucleotide sequence is not wild type.
2. The polynucleotide of aspect 1, wherein the portion of the GBA nucleotide sequence that is not wild type is codon-optimised.
3. The polynucleotide of aspect 1 or 2, wherein the GBA nucleotide sequence encodes a GCase protein or a fragment thereof and comprises a sequence that is at least 95%, at least 96%, at least 97%, at least 98%, at least 99%, at least 99.5%, at least 99.8%, or 100% identical to a nucleotide sequence of any one of SEQ ID NO: 1-8.
4. The polynucleotide of any one of aspects 1 to 3, wherein the GBA nucleotide sequence comprises a sequence of SEQ ID NO: 1 or a variant of SEQ ID NO: 1 encoding a GCase protein having GCase activity.
5. The polynucleotide of aspect 4, wherein the variant of SEQ ID NO: 1 is identical to SEQ ID NO: 1 except that it comprises nucleotide substitutions such that the GCase protein has 1, up to 2, up to 3, up to 4, up to 5, up to 6, up to 7, up to 8, up to 9, or up to 10 amino acid substitutions relative to the wild type GCase amino acid sequence of SEQ ID NO: 25.
6. The polynucleotide of aspect 4 or 5, wherein the variant of SEQ ID NO: 1 has 1, up to 2, up to 3, up to 4, up to 5, up to 6, up to 7, up to 8, up to 9, up to 10, up to 20, or up to 30 nucleotide substitutions relative to the sequence of SEQ ID NO: 1.
7. The polynucleotide of any one of aspects 4 to 6, wherein the variant of SEQ ID NO: 1 has 1, up to 2, up to 3, up to 4, up to 5, or up to 6 nucleotide substitutions relative to the sequence of SEQ ID NO: 1.
8. The polynucleotide of any one of aspects 4 to 7, wherein the variant of SEQ ID NO: 1 has up to 4 nucleotide substitutions relative to the sequence of SEQ ID NO: 1 and/or encodes a GCase protein having up to 3 amino acid substitutions relative to the wild type amino GCase sequence of SEQ ID NO: 25.
9. The polynucleotide of any one of aspects 4 to 8, wherein the variant of SEQ ID NO: 1 has up to 3 nucleotide substitutions relative to the sequence of SEQ ID NO: 1 and/or encodes a GCase protein having up to 2 amino acid substitutions relative to the wild type GCase amino acid sequence of SEQ ID NO: 25.
10. The polynucleotide of any one of aspects 4 to 9, wherein the variant of SEQ ID NO: 1 has 1 nucleotide substitution relative to the sequence of SEQ ID NO: 1 and/or encodes a GCase protein having up to 1 amino acid substitution relative to the wild type GCase amino acid sequence of SEQ ID NO: 25.
11. The polynucleotide of any one of aspects 1 to 3, wherein the GBA nucleotide sequence comprises a sequence of SEQ ID NO: 5 or a variant of SEQ ID NO: 5 encoding a GCase protein having GCase activity.
12. The polynucleotide of aspect 11, wherein the variant of SEQ ID NO: 5 is identical to SEQ ID NO: 5 except that it comprises nucleotide substitutions such that the GCase protein has 1, up to 2, up to 3, up to 4, up to 5, up to 6, up to 7, up to 8, up to 9, or up to 10 amino acid substitutions relative to the wild type GCase sequence of SEQ ID NO: 25.
13. The polynucleotide of aspect 11 or 12, wherein the variant of SEQ ID NO: 5 has 1, up to 2, up to 3, up to 4, up to 5, up to 6, up to 7, up to 8, up to 9, up to 10, up to 20, or up to 30 nucleotide substitutions relative to the sequence of SEQ ID NO: 5.
14. The polynucleotide of any one of aspects 11 to 13, wherein the variant of SEQ ID NO: 5 has 1, up to 2, up to 3, up to 4, up to 5, or up to 6 nucleotide substitutions relative to the sequence of SEQ ID NO: 5.
15. The polynucleotide of any one of aspects 11 to 14, wherein the variant of SEQ ID NO: 5 has up to 4 nucleotide substitutions relative to the sequence of SEQ ID NO: 5 and/or encodes a GCase protein having up to 3 amino acid substitutions relative to the wild type GCase amino acid sequence of SEQ ID NO: 25.
16. The polynucleotide of any one of aspects 11 to 15, wherein the variant of SEQ ID NO: 5 has up to 3 nucleotide substitutions relative to the sequence of SEQ ID NO: 5 and/or encodes a GCase protein having up to 2 amino acid substitutions relative to the wild type GCase amino acid sequence of SEQ ID NO: 25.
17. The polynucleotide of any one of aspects 11 to 16, wherein the variant has 1 nucleotide substitution relative to the sequence of SEQ ID NO: 5 and/or encodes a GCase protein having up to 1 amino acid substitution relative to the wild type GCase amino acid sequence of SEQ ID NO: 25.
18. The polynucleotide of any one of the preceding aspects, wherein the GBA nucleotide sequence encodes a GCase protein having 1, up to 2, up to 3, up to 4, or up to 5 amino acid substitutions relative to the wild type GCase amino acid sequence of SEQ ID NO: 25.
19. The polynucleotide of any one of the preceding aspects, wherein the GBA nucleotide sequence encodes a GCase protein having up to 3 amino acid substitutions relative to the wild type GCase amino acid sequence of SEQ ID NO: 25.
20. The polynucleotide of any one of the preceding aspects, wherein the GBA nucleotide sequence encodes a GCase protein having up to 2 amino acid substitutions relative to the wild type GCase amino acid sequence of SEQ ID NO: 25.
21. The polynucleotide of any one of the preceding aspects, wherein the GBA nucleotide sequence encodes a variant GCase protein having up to 1 amino acid substitution relative to the wild type GCase amino acid sequence of SEQ ID NO: 25.
22. A polynucleotide comprising a GBA nucleotide sequence, wherein the GBA nucleotide sequence encodes a GCase protein or a fragment thereof and comprises a sequence that is at least 95%, at least 96%, at least 97%, at least 98%, at least 99%, at least 99.5%, at least 99.8%, or 100% identical to a fragment of at least 1000, at least 1200, at least 1300, less than 1494, less than 1611, between 1000 and 1494, between 1000 and 1611, between 1300 and 1494, between 1300 and 1611, around 1494, or around 1611 nucleotides of any one of SEQ ID NO: 1-8.
23. The polynucleotide of any one of the preceding aspects, wherein the GBA nucleotide sequence comprises a sequence that is at least 98% identical to a fragment of at least 1300 nucleotides of any one of SEQ ID NO: 1-8.
24. The polynucleotide of any one of the preceding aspects, wherein the GBA nucleotide sequence comprises a sequence that is at least 99% identical to a fragment of at least 1300 nucleotides of any one of SEQ ID NO: 1-8.
25. The polynucleotide of any one of the preceding aspects, wherein the GBA nucleotide sequence comprises a sequence that is at least 98% identical to a nucleotide sequence of any one of SEQ ID NO: 1-8.
26. The polynucleotide of any one of the preceding aspects, wherein the GBA nucleotide sequence comprises a sequence that is at least 99% identical to a nucleotide sequence of any one of SEQ ID NO: 1-8.
27. The polynucleotide of any one of the preceding aspects, wherein the GBA nucleotide sequence comprises a sequence that is at least 98% identical to a fragment of at least 1300 nucleotides of SEQ ID NO: 1.
28. The polynucleotide of any one of the preceding aspects, wherein the GBA nucleotide sequence comprises a sequence that is at least 99% identical to a fragment of at least 1300 nucleotides of SEQ ID NO: 1.
29. The polynucleotide of any one of the preceding aspects, wherein the GBA nucleotide sequence comprises a sequence that is at least 98% identical SEQ ID NO: 1.
30. The polynucleotide of any one of the preceding aspects, wherein the GBA nucleotide sequence comprises a sequence that is at least 99% identical SEQ ID NO: 1.
31. The polynucleotide of any one of the preceding aspects, wherein the GBA nucleotide sequence comprises a sequence that is at least 98% identical to SEQ ID NO: 5.
32. The polynucleotide of any one of the preceding aspects, wherein the GBA nucleotide sequence comprises a sequence that is at least 99% identical to SEQ ID NO: 5.
33. The polynucleotide of any one of the preceding aspects, wherein at least a portion of the GBA nucleotide sequence is codon-optimised.
34. The polynucleotide of aspect 33, wherein the portion of the GBA nucleotide sequence that is codon-optimised is codon-optimised for expression in human liver cells.
35. The polynucleotide of aspect 33, wherein the GBA nucleotide sequence is codon-optimised for expression in human liver cells.
36. The polynucleotide of any one of aspects 2 to 35, wherein the portion of the GBA nucleotide sequence that is codon-optimised is a contiguous portion.
37. The polynucleotide of any one of aspects 2 to 36, wherein the portion of the GBA nucleotide sequence that is codon-optimised is at least 1000, at least 1200, at least 1300, less than 1494, between 1000 and 1494, between 1300 and 1494, or around 1494 nucleotides in length.
38. The polynucleotide of any one of aspects 2 to 37, wherein the portion of the GBA nucleotide sequence that is codon-optimised corresponds to a mature GCase protein.
39. The polynucleotide of any one of aspects 2 to 38, wherein the portion of the GBA nucleotide sequence that is codon-optimised does not encode all or a portion of a signal peptide.
40. The polynucleotide of any one of aspects 2 to 39, wherein the GBA nucleotide sequence or the portion of the GBA nucleotide sequence that is codon-optimised comprises a reduced number of CpGs compared to a corresponding portion of a wild type GBA nucleotide sequence.
41. The polynucleotide of aspect 40, wherein the GBA nucleotide sequence or the portion of the GBA nucleotide sequence that is codon-optimised comprises less than 40, less than 20, less than 18, less than 10, or less than 5 CpGs.
42. The polynucleotide of aspect 41, wherein the GBA nucleotide sequence or the portion of the GBA nucleotide sequence that is codon-optimised comprises less than 5, less than 4, less than 3, or less than 2 CpGs per 100 nucleotides.
43. The polynucleotide of aspect 41 or 42, wherein the GBA nucleotide sequence or the portion of the GBA nucleotide sequence that is codon-optimised is CpG-free.
44. The polynucleotide of any one of aspects 40 to 43, wherein the wild type GBA nucleotide sequence is SEQ ID NO: 9.
45. The polynucleotide of any one of aspects 2 to 44, wherein the portion of the GBA nucleotide sequence that is codon-optimised is at least 80%, at least 85%, at least 90%, at least 95%, at least 98%, at least 99%, at least 99.5%, at least 99.8%, or 100% identical to a fragment of at least 1000, at least 1200, at least 1300, less than 1494, between 1000 and 1494, between 1300 and 1494, or around 1494 nucleotides of any one of SEQ ID NO: 1-4.

46. The polynucleotide of aspect 45, wherein the portion of the GBA nucleotide sequence that is codon-optimised is at least 80%, at least 85%, at least 90%, at least 95%, at least 98%, at least 99%, at least 99.5%, at least 99.8%, or 100% identical to any one of SEQ ID NO: 1-4.

47. The polynucleotide of any one of aspects 2 to 46, wherein the portion of the GBA nucleotide sequence that is codon-optimised is at least 80%, at least 85%, at least 90%, at least 95%, at least 98%, at least 99%, at least 99.5%, at least 99.8%, or 100% identical to a fragment of at least 1000, at least 1200, at least 1300, less than 1494, between 1000 and 1494, between 1300 and 1494, or around 1494 nucleotides of SEQ ID NO: 1.

48. The polynucleotide of aspect 47, wherein the portion of the GBA nucleotide sequence that is codon-optimised is at least 80%, at least 85%, at least 90%, at least 95%, at least 98%, at least 99%, at least 99.5%, at least 99.8%, or 100% identical to SEQ ID NO: 1.

49. The polynucleotide of any one of aspects 2 to 48, wherein the portion of the GBA nucleotide sequence that is codon-optimised is at least 99.5%, at least 99.8%, or 100% identical to a fragment of at least 1300 nucleotides of SEQ ID NO: 1.

50. The polynucleotide of aspect 49, wherein the portion of the GBA nucleotide sequence that is codon-optimised is at least 99%, at least 99.5%, at least 99.8%, or 100% identical to SEQ ID NO: 1.

51. The polynucleotide of any one of the preceding aspects, wherein the GBA nucleotide sequence comprises a portion that is not codon-optimised.

52. The polynucleotide of aspect 51, wherein the portion that is not codon-optimised encodes all or a portion of a GCase signal peptide.

53. The polynucleotide of aspect 51 or 52, wherein the portion that is not codon-optimised is at least 80, at least 90, at least 100, at least 110, less than 200, less than 170, less than 140, or around 117 nucleotides.

54. The polynucleotide of any one of aspects 51 to 53, wherein the portion that is not codon-optimised comprises 1 or more CpGs.

55. The polynucleotide of any one of the preceding aspects, wherein the polynucleotide further comprises a transcription regulatory element.

56. The polynucleotide of aspect 55, wherein the transcription regulatory element comprises a liver-specific promoter.

57. The polynucleotide of aspect 55 or 56, wherein the transcription regulatory element comprises an A1AT promoter or a fragment of an A1AT promoter.

58. The polynucleotide of aspect 57, wherein the fragment of an A1AT promoter is at least 100, at least 120, at least 150, at least 180, less than 255, between 100 and 255, between 150 and 225, between 150 and 300, or between 180 and 255 nucleotides in length.

59. The polynucleotide of aspect 58, wherein the fragment of an A1AT promoter is between 180 and 255 nucleotides in length.

60. The polynucleotide of any one of the preceding aspects, wherein the polynucleotide comprises a promoter that is at least 80%, at least 85%, at least 90%, at least 95%, at least 98%, at least 99%, at least 99.5%, at least 99.8%, or 100% identical to SEQ ID NO: 12 or SEQ ID NO: 15.

61. The polynucleotide of aspect 60, wherein the polynucleotide comprises a promoter that is at least 98%, at least 99%, at least 99.5%, at least 99.8%, or 100% identical to SEQ ID NO. 12 or SEQ ID NO: 15.

62. The polynucleotide of aspect 61, wherein the polynucleotide comprises a promoter of SEQ ID NO. 12 or SEQ ID NO: 15.

63. The polynucleotide of any one of aspects 55 to 62, wherein the transcription regulatory element comprises a fragment of an A1AT promoter that is equal to or less than 418 nucleotides, equal to or less than 255 nucleotides, or equal to or less than 185 nucleotides in length and comprises SEQ ID NO: 12.

64. The polynucleotide of any one of aspects 55 to 63, wherein the transcription regulatory element comprises an enhancer.

65. The polynucleotide of aspect 64, wherein the enhancer is an HCR enhancer or a fragment of an HCR enhancer.

66. The polynucleotide of aspect 65, wherein the fragment of an HCR enhancer is a fragment of at least 80, at least 90, at least 100, less than 192, between 80 and 192, between 90 and 192, between 100 and 250, or between 117 and 192 nucleotides in length.

67. The polynucleotide of aspect 66, wherein the fragment of an HCR enhancer is between 117 and 192 nucleotides in length.

68. The polynucleotide of any one of the preceding aspects, wherein the polynucleotide comprises an enhancer that is at least 80%, at least 85%, at least 90%, at least 95% at least 98%, at least 99%, at least 99.5%, at least 99.8%, or 100% identical to SEQ ID NO: 11 or SEQ ID NO: 16.

69. The polynucleotide of aspect 68, wherein the polynucleotide comprises an enhancer that is at least 98%, at least 99%, at least 99.5%, at least 99.8%, or 100% identical to SEQ ID NO: 11 or SEQ ID NO: 16.

70. The polynucleotide of aspect 69, wherein the polynucleotide comprises an enhancer of SEQ ID NO: 11 or SEQ ID NO: 16.

71. The polynucleotide of any one of aspects 55 to 70, wherein the transcription regulatory element comprises a fragment of an HCR enhancer that is equal to or less than 321 nucleotides, equal to or less than 192 nucleotides or equal to or less than 117 nucleotides in length and comprises SEQ ID NO: 11.

72. The polynucleotide of any one of aspects 55 to 71, wherein the transcription regulatory element is at least 80%, at least 85%, at least 90%, at least 95%, at least 98%, at least 99%, at least 99.5%, at least 99.8%, or 100% identical to SEQ ID NO: 10.

73. The polynucleotide of aspect 72, wherein the transcription regulatory element has a sequence of SEQ ID NO: 10.

74. The polynucleotide of any one of the preceding aspects, wherein:
(i) the GBA nucleotide sequence comprises a sequence that is at least 95%, at least 98%, at least 99%, at least 99.5%, at least 99.8%, or 100% identical to SEQ ID NOs: 1 or 5; and
(ii) the polynucleotide comprises a promoter that is at least 98%, at least 99%, at least 99.5%, at least 99.8%, or 100% identical to SEQ ID NO. 12 and/or an enhancer element that is at least 98%, at least 99%, at least 99.5%, at least 99.8% or 100% identical to SEQ ID NO: 11.

75. The polynucleotide of any one of the preceding aspects, wherein:
(i) the GBA nucleotide sequence comprises a sequence that is at least 95%, at least 98%, at least 99%, at least 99.5%, at least 99.8%, or 100% identical to SEQ ID NOs: 1 or 5; and
  (ii) the polynucleotide comprises a transcription regulatory element that is at least 98%, at least 99%, at least 99.5%, at least 99.8%, or 100% identical to SEQ ID NO. 10.
76. The polynucleotide of aspect 57, wherein the A1AT promoter or fragment of an A1AT promoter is at least 200, at least 250, at least 300, less than 500, between 200 and 500, between 250 and 500, between 350 and 450, or around 418 nucleotides in length.
77. The polynucleotide of aspect 76, wherein the A1AT promoter or fragment of an A1AT promoter is between 350 and 450 nucleotides in length.
78. The polynucleotide of aspect 65, wherein the HCR enhancer or fragment of an HCR enhancer is a fragment of at least 150, at least 190, at least 230, less than 400, between 150 and 400, between 190 and 370, between 230 and 340, between 250 and 340, or around 321 nucleotides in length.
79. The polynucleotide of aspect 78, wherein the HCR enhancer or fragment of an HCR enhancer is between 250 and 340 nucleotides in length.
80. The polynucleotide of any one of aspects 55 to 79, wherein the transcription regulatory element is at least 80%, at least 85%, at least 90%, at least 95%, at least 98%, at least 99%, at least 99.5%, at least 99.8%, or 100% identical to SEQ ID NO: 14.
81. The polynucleotide of aspect 80, wherein the transcription regulatory element has a sequence of SEQ ID NO: 14.
82. The polynucleotide of any one of aspects 1 to 56 or 76 to 79, wherein:
  (i) the GBA nucleotide sequence comprises a sequence that is at least 95%, at least 98%, at least 99%, at least 99.5%, at least 99.8%, or 100% identical to SEQ ID NOs: 1 or 5; and
  (iii) the polynucleotide comprises a transcription regulatory element that is at least 98%, at least 99%, at least 99.5%, at least 99.8%, or 100% identical to SEQ ID NO: 14.
83. The polynucleotide of any one of aspects 1 to 56 or 76 to 79, wherein:
  (i) the GBA nucleotide sequence comprises a sequence that is at least 95%, at least 98%, at least 99%, at least 99.5%, at least 99.8%, or 100% identical to SEQ ID NOs: 1 or 5; and
  (ii) the polynucleotide comprises a promoter that is at least 98%, at least 99%, at least 99.5%, at least 99.8%, or 100% identical to SEQ ID NO. 15 and/or an enhancer element that is at least 98%, at least 99%, at least 99.5%, at least 99.8% or 100% identical to SEQ ID NO: 16.
84. The polynucleotide of any one of the preceding aspects, wherein the GCase encoded by the GBA nucleotide sequence is expressed in human liver cells at higher levels compared to a GCase encoded by a wild type GBA nucleotide sequence in an otherwise identical reference polynucleotide.
85. The polynucleotide of any one of the preceding aspects, wherein the GCase encoded by the GBA nucleotide sequence is expressed in human liver cells at least 1.1×, at least 1.2×, at least 1.3×, at least 1.4×, or at least 1.5× higher compared to a GCase encoded by a wild type GBA nucleotide sequence in a reference polynucleotide.
86. The polynucleotide of aspect 84 or 85, wherein the reference polynucleotide comprises a wild type GBA nucleotide sequence of SEQ ID NO: 9.
87. The polynucleotide of aspect 86, wherein the reference polynucleotide comprises a promoter of SEQ ID NO: 13.
88. The polynucleotide of any one of the preceding aspects, wherein the GCase encoded by the GBA nucleotide sequence is expressed in human liver cells at higher or non-statistically significant different levels compared to GCase encoded by an otherwise identical reference polynucleotide comprising a GBA nucleotide sequence of SEQ ID NO: 9 and operably linked to a promoter of SEQ ID NO: 13.
89. The polynucleotide of any one of the preceding aspects, wherein the polynucleotide comprises DNA or RNA.
90. A viral particle comprising a recombinant genome comprising the polynucleotide of any one of the preceding aspects.
91. The viral particle of aspect 90, which is an AAV, adenoviral, or lentiviral viral particle.
92. The viral particle of aspect 91, which is an AAV viral particle.
93. The viral particle of any one of aspects 90 to 92, wherein the viral particle comprises a liver-tropic or CNS-tropic capsid.
94. The viral particle of aspect 93, wherein the liver-tropic capsid comprises a sequence at least 98%, at least 99%, or at least 99.5% identical to a fragment of at least 600, at least 650, at least 700, between 600 and 736, between 650 and 736, or between 700 and 736 amino acids of SEQ ID NO: 19 or 20.
95. The viral particle of aspect 94, wherein the liver-tropic capsid comprises a sequence at least 99% identical to SEQ ID NO: 19.
96. The viral particle of aspect 94, wherein the liver-tropic capsid comprises a sequence at least 99% identical to SEQ ID NO: 20.
97. The viral particle of aspect 93, wherein the CNS-tropic capsid comprises a sequence at least 98%, at least 99%, or at least 99.5% identical to a fragment of at least 600, at least 650, at least 700, between 600 and 736, between 650 and 736 or between 700 and 736 amino acids of SEQ ID NO: 21.
98. The viral particle of aspect 97, wherein the CNS-tropic capsid comprises a sequence at least 99% identical to SEQ ID NO: 21.
99. The viral particle of any one of aspects 90 to 98, wherein the recombinant genome further comprises:
  a) AAV2 ITRs;
  b) a poly A sequence; and/or
  c) an intron.
100. The viral particle of aspect 99, wherein the recombinant genome is single-stranded.
101. The viral particle of any one of aspects 90 to 100, wherein on transduction into Huh-7 cells, the viral particle expresses GCase or a fragment thereof such that the GCase activity in the transduced cell is greater than the activity of GCase or a fragment thereof in a cell transduced with an otherwise identical viral particle comprising a GBA nucleotide sequence of SEQ ID NO: 9.
102. The viral particle of any one of aspects 90 to 101, wherein on transduction into Huh-7 cells, the viral particle expresses GCase or a fragment thereof such that the GCase activity in the transduced cell is at least 2×, at least 3×, at least 4×, at least 5×, at least 10×, or at least 20× greater than the activity of GCase or a fragment thereof in a cell transduced with an otherwise identical viral particle comprising a GBA nucleotide sequence of SEQ ID NO: 9.

103. The viral particle of aspect 101 or 102, wherein the activity is measured using a fluorometric substrate which is specific for GCase.

104. A composition comprising the polynucleotide or viral particle of any one of the preceding aspects and a pharmaceutically acceptable excipient.

105. The polynucleotide, viral particle or composition of any one of the preceding aspects for use in a method of treatment.

106. The polynucleotide, viral particle or composition for use of aspect 105, wherein the method of treatment comprises administering an effective amount of the polynucleotide, composition or viral particle of any one of aspects 1 to 104 to a patient.

107. A method of treatment comprising administering an effective amount of the polynucleotide, composition or viral particle of any one of aspects 1 to 104 to a patient.

108. Use of the polynucleotide, viral particle or composition of any one of aspects 1 to 104 in the manufacture of a medicament for use in a method of treatment.

109. The use of aspect 108, wherein the method of treatment comprises administering an effective amount of the polynucleotide or viral particle of any one of aspects 1 to 104 to a patient.

110. The polynucleotide, viral particle, composition, use or method of any one of aspects 105 to 109, wherein the method of treatment is a method of treating a disease associated with GCase deficiency.

111. The polynucleotide, viral particle, composition, use or method of any one of aspects 105 to 109, wherein the method of treatment is a method of treating Parkinson's disease.

112. The polynucleotide, viral particle, composition, use or method of any one of aspects 105 to 109, wherein the method of treatment is a method of treating Gaucher disease.

113. The polynucleotide, viral particle, composition, use or method of aspect 112, wherein the Gaucher disease is Gaucher disease type I.

114. The polynucleotide, viral particle, composition, use or method of aspect 112, wherein the Gaucher disease is Gaucher disease type II.

115. The polynucleotide, viral particle, composition, use or method of aspect 112, wherein the Gaucher disease is Gaucher disease type III.

116. The polynucleotide, viral particle, composition, use or method of any one of aspects 112 to 115, wherein the patient has antibodies or inhibitors to a recombinant GCase with which the patient has previously been treated as part of an enzyme replacement therapy.

117. Use of the polynucleotide, viral particle or composition of any one of aspects 1 to 104 in the manufacture of a medicament for achieving a stable GCase activity in a subject.

118. Use of the polynucleotide, viral particle or composition of any one of aspects 1 to 104 in the manufacture of a medicament for providing greater GCase bioavailability in a subject compared to the bioavailability from GCase enzyme replacement therapy, wherein the bioavailability is measured over a period of 2 weeks from administration.

119. A method of achieving a stable GCase activity in a subject by administering to the subject the polynucleotide, viral particle or composition of any one of aspects 1 to 104.

120. A method of providing greater GCase bioavailability in a subject compared to the bioavailability from GCase enzyme replacement therapy by administering to the subject the polynucleotide, viral particle or composition of any one of aspects 1 to 104, wherein the bioavailability is measured over a period of 2 weeks from administration.

121. The method or use of any one of aspects 117 to 120, wherein achieving a stable GCase activity in a subject or providing greater GCase bioavailability in a subject treats a disease in the subject.

122. The polynucleotide, viral particle or composition of any one of aspects 1 to 104, for use in a method of expressing the GBA nucleotide sequence and achieving a stable GCase activity in a subject.

123. The polynucleotide, viral particle or composition of any one of aspects 1 to 104, for use in a method of expressing the GBA nucleotide sequence and providing greater GCase bioavailability in a subject compared to the bioavailability from GCase enzyme replacement therapy, wherein the bioavailability is measured over a period of 2 weeks from administration.

124. The polynucleotide, viral particle or composition for use of aspect 122 or 123, wherein achieving a stable GCase activity and/or providing greater GCase bioavailability leads to the treatment of a disease in the subject.

125. The polynucleotide, viral particle or composition for use, use or method of any one of aspects 117 to 124, wherein the GCase activity and/or bioavailability is measured using a fluorometric substrate which is specific for GCase.

126. The polynucleotide, viral particle or composition for use, use or method of any one of aspects 117 to 125, wherein the GCase activity is measured in the serum or plasma of the subject.

127. The polynucleotide, viral particle or composition for use, use or method of any one of aspects 117 to 126, wherein the GCase activity is measured in the macrophages of the subject.

128. The polynucleotide, viral particle or composition for use, use or method of any one of aspects 117 to 127, wherein the GCase activity is stable at a level of at least 1, at least 2, at least 3, at least 4, at least 5, at least 6, at least 7, at least 8, or at least 9 µmol/h/ml in the subject.

129. The polynucleotide, viral particle or composition for use, use or method of any one of aspects 117 to 128, wherein the GCase activity is stable at a level of at least 3 µmol/h/ml in the subject.

130. The polynucleotide, viral particle or composition for use, use or method of any one of aspects 117 to 129, wherein the GCase activity is stable at a level of at least 5 µmol/h/ml in the subject.

131. The polynucleotide, viral particle or composition for use, use or method of any one of aspects 117 to 130, wherein the GCase activity is stable at a level of at least 9 µmol/h/ml in the subject.

132. The polynucleotide, viral particle or composition for use, use or method of any one of aspects 117 to 131, wherein the method comprises administering an effective dose of the polynucleotide, viral particle or composition to the subject.

133. The polynucleotide, viral particle or composition for use, use or method of any one of aspects 117 to 132, wherein the stable GCase activity is a GCase activity of at least 10%, at least 20%, at least 30%, at least 40%, or at least 50% relative to the GCase activity of a healthy subject.
134. The polynucleotide, viral particle or composition for use, use or method of any one of aspects 117 to 133, wherein the stable GCase activity is a GCase activity of between 10% and 100%, between 20% and 90%, between 30% and 70%, between 40% and 70%, or between 50% and 70% relative to the GCase activity of a healthy subject.
135. The polynucleotide, viral particle or composition for use, use or method of any one of aspects 117 to 134, wherein the stable GCase activity is stable for at least 5 weeks from administration.
136. The polynucleotide, viral particle or composition for use, use or method of any one of aspects 117 to 135, wherein the stable GCase activity is stable for at least 10 weeks from administration.
137. The polynucleotide, viral particle or composition for use, use or method of any one of aspects 117 to 136, wherein the stable GCase activity is stable for at least 15 weeks from administration.
138. The polynucleotide, viral particle or composition for use, use or method of any one of aspects 117 to 137, wherein the stable GCase activity is stable for at least 20 weeks from administration.
139. The polynucleotide, viral particle or composition for use, use or method of any one of aspects 117 to 138, wherein the stable GCase activity is stable for at least 25 weeks from administration.
140. The polynucleotide, viral particle or composition for use, use or method of any one of aspects 117 to 139, wherein the stable GCase activity is stable for at least 30 weeks from administration.
141. The polynucleotide, viral particle or composition for use, use or method of any one of aspects 117 to 140, wherein the stable GCase activity is stable for at least 35 weeks from administration.
142. The polynucleotide, viral particle or composition for use, use or method of any one of aspects 117 to 141, wherein the stable GCase activity is stable for at least 40 weeks after administration.
143. The polynucleotide, viral particle or composition for use, use or method of any one of aspects 117 to 142, wherein the method achieves a greater GCase activity in the liver, spleen, and/or bone marrow of the subject at least 5, at least 10, at least 15, at least 20, at least 25, at least 30, or at least 35 weeks after administration when compared to the activity measured in a subject administered an effective dose of a GCase enzyme replacement therapy, when measured in the same assay at the same time point after administration.
144. The polynucleotide, viral particle or composition for use, use or method of any one of aspects 117 to 143, wherein the method achieves a greater GCase bioavailability in the liver spleen and/or bone marrow subject over a period of at least 5, at least 10, at least 15, at least 20, at least 25, at least 30, or at least 35 weeks after administration when compared to the bioavailability measured in a subject administered an effective dose of a GCase enzyme replacement therapy, when measured in the same assay at the same time point after administration.
145. The polynucleotide, viral particle or composition for use, use or method of any one of aspects 118, 120 or 123 to 144, wherein the GCase enzyme replacement therapy comprises administration of a GCase polypeptide having the sequence of SEQ ID NO: 25.
146. The polynucleotide, viral particle or composition for use, use or method of aspect 145, wherein the GCase enzyme replacement therapy comprises administration of the GCase polypeptide at a dose of between 40 and 100, between 50 and 80, between 60 and 70, or around 60 U/kg BW.
147. The polynucleotide, viral particle or composition for use, use or method of any one of aspects 121 or 124 to 146, wherein the disease is Gaucher disease.
148. The polynucleotide, viral particle or composition for use, use or method of aspect 147, wherein the Gaucher disease is Gaucher disease type I.
149. The polynucleotide, viral particle or composition for use, use or method of aspect 147, wherein the Gaucher disease is Gaucher disease type II.
150. The polynucleotide, viral particle or composition for use, use or method of aspect 147, wherein the Gaucher disease is Gaucher disease type III.
151. The polynucleotide, viral particle or composition for use, use or method of any one of aspects 117 to 150, wherein the patient has antibodies or inhibitors to a recombinant GCase with which the patient has previously been treated as part of an enzyme replacement therapy.
152. Use of the polynucleotide, viral particle or composition of any one of aspects 1 to 104 in the manufacture of a medicament for reducing the levels of hexosylceramide and/or hexosylsphingosine in a subject suffering from a disease or condition associated with GCase deficiency.
153. A method of reducing the levels of hexosylceramide and/or hexosylsphingosine in a subject suffering from a disease or condition associated with GCase deficiency by administering to the subject the polynucleotide, viral particle or composition of any one of aspects 1 to 104.
154. The use or method of aspect 152 or 153 wherein reducing the levels of hexosylceramide and/or hexosylsphingosine in a subject treats the disease or condition associated with GCase deficiency.
155. The polynucleotide, viral particle or composition of any one of aspects 1 to 104, for use in a method of reducing hexosylceramide and/or hexosylsphingosine levels in a subject suffering from a disease or condition associated with GCase deficiency, optionally wherein reducing hexosylceramide and/or hexosylsphingosine levels leads to the treatment of the disease or condition associated with GCase deficiency.
156. The polynucleotide, viral particle or composition for use, use or method of any one of aspects 152 to 155, wherein the hexosylceramide and/or hexosylsphingosine levels are reduced by 2 times or more, 3 times or more, 4 times or more, 5 times or more, 6 times or more, 2 to 3 times, 2 to 4 times, 2 to 5 times, 2 to 6 times, or 3 to 5 times when compared to the hexosylceramide and/or hexosylsphingosine levels at the time of administration of the polynucleotide, viral particle or composition of any one of aspects 1 to 104.
157. The polynucleotide, viral particle or composition for use, use or method of any one of aspects 152 to 156, wherein the reduction in hexosylceramide and/or hexosylsphingosine levels is greater than the reduction achieved in a subject administered an effective dose of a GCase enzyme replacement therapy, optionally when the hexosylceramide and/or hexosylsphingosine levels are measured at least 6 weeks, at least 8 weeks, at least 10 weeks or at least 12 weeks after administration.

158. The polynucleotide, viral particle or composition for use, use or method of aspect 157, wherein the GCase enzyme replacement therapy comprises administration of a GCase polypeptide having the sequence of SEQ ID NO: 25.

159. The polynucleotide, viral particle or composition for use, use or method of aspect 158, wherein the GCase enzyme replacement therapy comprises administration of the GCase polypeptide at a dose of between 40 and 100, between 50 and 80, between 60 and 70, or around 60 U/kg BW.

160. The polynucleotide, viral particle or composition for use, use or method of any one of aspects 152 to 159, wherein the hexosylceramide and/or hexosylsphingosine levels are measured in the macrophages of the subject.

161. The polynucleotide, viral particle or composition for use, use or method of any one of aspects 152 to 160, wherein the hexosylceramide and/or hexosylsphingosine levels are measured in the spleen of the subject.

162. The polynucleotide, viral particle or composition for use, use or method of any one of aspects 152 to 161, wherein the hexosylceramide and/or hexosylsphingosine levels are measured in the liver of the subject.

163. The polynucleotide, viral particle or composition for use, use or method of any one of aspects 152 to 162, wherein the hexosylceramide and/or hexosylsphingosine levels are measured in the serum of the subject.

164. The polynucleotide, viral particle or composition for use, use or method of any one of aspects 152 to 163, wherein the hexosylceramide and/or hexosylsphingosine levels are measured by mass spectrometry.

165 The polynucleotide, viral particle or composition for use, use or method of any one of aspects 152 to 164, wherein the disease is Gaucher disease.

166. The polynucleotide, viral particle or composition for use, use or method of aspect 165, wherein the Gaucher disease is Gaucher disease type I.

167. The polynucleotide, viral particle or composition for use, use or method of aspect 165, wherein the Gaucher disease is Gaucher disease type II.

168. The polynucleotide, viral particle or composition for use, use or method of aspect 165, wherein the Gaucher disease is Gaucher disease type III.

169. The polynucleotide, viral particle or composition for use, use or method of any one of aspects 152 to 168, wherein the patient has antibodies or inhibitors to a recombinant GCase with which the patient has previously been treated as part of an enzyme replacement therapy.

FURTHER ASPECTS OF THE INVENTION

The invention is also described in the following aspects.

1. A polynucleotide comprising a GBA nucleotide sequence, wherein the GBA nucleotide sequence encodes a β-Glucocerebrosidase (GCase) protein or fragment thereof and wherein at least a portion of the GBA nucleotide sequence is not wild type, optionally wherein the portion of the GBA nucleotide sequence that is not wild type is codon-optimised, more optionally wherein the GBA nucleotide sequence encodes a GCase protein or a fragment thereof and comprises a sequence that is at least 95%, at least 96%, at least 97%, at least 98%, at least 99%, at least 99.5%, at least 99.8%, or 100% identical to a nucleotide sequence of any one of SEQ ID NO: 1-8.

2. A polynucleotide comprising a GBA nucleotide sequence, wherein the GBA nucleotide sequence encodes a GCase protein or a fragment thereof and comprises a sequence that is at least 95%, at least 96%, at least 97%, at least 98%, at least 99%, at least 99.5%, at least 99.8%, or 100% identical to a fragment of at least 1000, at least 1200, at least 1300, less than 1494, less than 1611, between 1000 and 1494, between 1000 and 1600, between 1300 and 1494, between 1300 and 1611, around 1494, or around 1611 nucleotides of any one of SEQ ID NO: 1-8.

3. The polynucleotide of any one of aspects 1 to 2, wherein at least a portion of the GBA nucleotide sequence is codon-optimised.

4. The polynucleotide of aspect 3, wherein:
   (a) the at least a portion of the GBA nucleotide sequence that is codon-optimised is codon-optimised for expression in human liver cells;
   (b) the portion of the GBA nucleotide sequence that is codon-optimised is a contiguous portion;
   (c) the portion of the GBA nucleotide sequence that is codon-optimised is at least 1000, at least 1200, at least 1300, less than 1494, between 1000 and 1494, between 1300 and 1494, or around 1494 nucleotides in length;
   (d) the portion of the GBA nucleotide sequence that is codon-optimised corresponds to a mature GCase protein;
   (e) the portion of the GBA nucleotide sequence that is codon-optimised does not encode all or a portion of a signal peptide;
   (f) the GBA nucleotide sequence or the portion of the GBA nucleotide sequence that is codon-optimised comprises a reduced number of CpGs compared to a corresponding portion of a wild type GBA nucleotide sequence; optionally wherein the GBA nucleotide sequence or the portion of the GBA nucleotide sequence that is codon-optimised comprises less than 40, less than 20, less than 18, less than 10, or less than 5 CpGs, more optionally wherein the GBA nucleotide sequence or the portion of the GBA nucleotide sequence that is codon-optimised comprises less than 5, less than 4, less than 3, or less than 2 CpGs per 100 nucleotides, more optionally wherein the GBA nucleotide sequence or the portion of the GBA nucleotide sequence that is codon-optimised is CpG-free, preferably wherein the wild type GBA nucleotide sequence is SEQ ID NO: 9; and/or
   (g) the portion of the GBA nucleotide sequence that is codon-optimised is at least 80%, at least 85%, at least 90%, at least 95%, at least 98%, at least 99%, at least 99.5%, at least 99.8%, or 100% identical to a fragment of at least 1000, at least 1200, at least 1300, less than 1494, between 1000 and 1494, between 1300 and 1494, or around 1494 nucleotides of any one of SEQ ID NO: 1-4.

5. The polynucleotide of any one of the preceding aspects, wherein the GBA nucleotide sequence comprises a portion that is not codon-optimised, optionally wherein:
   (a) the portion that is not codon-optimised encodes all or a portion of a GCase signal peptide;

(b) the portion that is not codon-optimised is at least 80, at least 90, at least 100, at least 110, less than 200, less than 170, less than 140, or around 117 nucleotides; and/or (c) the portion that is not codon-optimised comprises 1 or more CpGs.

6. The polynucleotide of any one of the preceding aspects, wherein the polynucleotide further comprises a transcription regulatory element, optionally wherein the transcription regulatory element comprises a liver-specific promoter and/or an enhancer.

7. The polynucleotide of aspect 6, wherein the transcription regulatory element comprises an A1AT promoter or a fragment of an A1AT promoter, optionally wherein
   (a) the A1AT promoter or the fragment of an A1AT promoter is at least 100, at least 120, at least 150, at least 180, less than 255, between 100 and 255, between 150 and 225, between 150 and 300, or between 180 and 255 nucleotides in length, more optionally wherein the fragment of an A1AT promoter is between 180 and 255 nucleotides in length;
   (b) the A1AT promoter or the fragment of an A1AT promoter is at least 200, at least 250, at least 300, less than 500, between 200 and 500, between 250 and 500, between 350 and 450, or around 418 nucleotides in length, more optionally wherein the fragment of an AAT promoter is between 350 and 450 nucleotides in length;
   (c) the polynucleotide comprises a promoter that is at least 80%, at least 85%, at least 90%, at least 95%, at least 98%, at least 99%, at least 99.5%, at least 99.8%, or 100% identical to SEQ ID NO: 12 or SEQ ID NO: 15.

8 The polynucleotide of aspects 6 or 7, wherein the enhancer is an HCR enhancer or a fragment of an HCR enhancer, optionally wherein:
   (a) the HCR enhancer or the fragment of an HCR enhancer is a fragment of at least 80, at least 90, at least 100, less than 192, between 80 and 192, between 90 and 192, between 100 and 250, or between 117 and 192 nucleotides in length, more optionally wherein the fragment of an HCR enhancer is between 117 and 192 nucleotides in length;
   (b) the HCR enhancer or the fragment of an HCR enhancer is a fragment of at least 150, at least 190, at least 230, less than 400, between 150 and 400, between 190 and 370, between 230 and 340, between 250 and 340, or around 321 nucleotides in length, more optionally wherein the fragment of an HCR enhancer is between 250 and 340 nucleotides in length
   (c) the polynucleotide comprises an enhancer that is at least 80%, at least 85%, at least 90%, at least 95% at least 98%, at least 99%, at least 99.5%, at least 99.8%, or 100% identical to SEQ ID NO: 11 or SEQ ID NO: 16.

9. The polynucleotide of aspect 6, wherein the transcription regulatory element is at least 80%, at least 85%, at least 90%, at least 95%, at least 98%, at least 99%, at least 99.5%, at least 99.8%, or 100% identical to SEQ ID NO: 10 or 14.

10. The polynucleotide of any one of the preceding aspects, wherein the GCase encoded by the GBA nucleotide sequence is expressed in human liver cells at higher levels compared to a GCase encoded by a wild type GBA nucleotide sequence in an otherwise identical reference polynucleotide, optionally wherein the GCase encoded by the GBA nucleotide sequence is expressed in human liver cells at least 1.1×, at least 1.2×, at least 1.3×, at least 1.4×, or at least 1.5× higher compared to a GCase encoded by a wild type GBA nucleotide sequence in an otherwise identical reference polynucleotide, more optionally wherein the reference polynucleotide comprises a wild type GBA nucleotide sequence of SEQ ID NO: 9, optionally wherein the reference polynucleotide comprises a promoter of SEQ ID NO: 13.

11. A viral particle comprising a recombinant genome comprising the polynucleotide of any one of the preceding aspects.

12. The viral particle of aspect 11, which is an AAV, adenoviral, or lentiviral viral particle, optionally which is an AAV viral particle.

13. The viral particle of any one of aspects 11-12, wherein the viral particle comprises a liver-tropic or CNS-tropic capsid.

14. The viral particle of aspect 13, wherein the liver-tropic capsid comprises a sequence at least 98%, at least 99%, at least 99.5% to a fragment of at least 600, at least 650, at least 700, between 600 and 736, between 650 and 736 or between 700 and 736 amino acids of SEQ ID NO: 19, 20 or 24.

15. The viral particle of aspect 13, wherein the CNS-tropic capsid comprises a sequence at least 98%, at least 99%, at least 99.5% to a fragment of at least 600, at least 650, at least 700, between 600 and 736, between 650 and 736 or between 700 and 736 amino acids of SEQ ID NO: 21.

16. The viral particle of any one of aspects 11 to 15, wherein the recombinant genome further comprises:
    a) AAV2 ITRs;
    b) a poly A sequence; and/or
    c) an intron;
    optionally wherein the recombinant genome is single-stranded.

17. The viral particle of any one of aspects 11 to 16, wherein on transduction into Huh-7 cells, the viral particle expresses GCase or a fragment thereof such that the GCase activity in the transduced cell is greater than the activity of GCase or a fragment thereof in a cell transduced with an otherwise identical viral particle comprising a GBA nucleotide sequence of SEQ ID NO: 9, optionally wherein on transduction into Huh-7 cells, the viral particle expresses GCase or a fragment thereof such that the GCase activity in the transduced cell is at least 2×, at least 3×, at least 4×, at least 5×, at least 10×, or at least 20× greater than the activity of GCase or a fragment thereof in a cell transduced with an otherwise identical viral particle comprising a GBA nucleotide sequence of SEQ ID NO: 9, more optionally wherein the activity is measured using a fluorometric substrate which is specific for GCase.

18. A composition comprising the polynucleotide or viral particle of any one of the preceding aspects and a pharmaceutically acceptable excipient.

19. The polynucleotide, viral particle or composition of any one of the preceding aspects for use in a method of treatment.

20. The polynucleotide, viral particle or composition for use of aspect 19, wherein the method of treatment comprises administering an effective amount of the polynucleotide, composition or viral particle of any one of aspects 1 to 17 to a patient.

21. The polynucleotide, viral particle, or composition for use of any one of aspects 19 to 20, wherein the method of treatment is a method of treating a disease associated with GCase deficiency.
22. The polynucleotide, viral particle, or composition for use of any one of aspects 19 to 20, wherein the method of treatment is a method of treating Parkinson's disease.
23. The polynucleotide, viral particle, or composition for use of any one of aspects 19 to 20, wherein the method of treatment is a method of treating Gaucher disease.
24. The polynucleotide, viral particle, or composition for use of aspect 23, wherein the Gaucher disease is Gaucher disease type I, II or III.
25. The polynucleotide, viral particle, or composition for use of any one of aspects 23 to 24, wherein the patient has antibodies or inhibitors to a recombinant GCase with which the patient has previously been treated as part of an enzyme replacement therapy.

EXAMPLES

Example 1—Methods

Unless specified otherwise, the following general methods were followed in the examples described below.
rAAV production AAV2/8 particles were produced by transient transfection of HEK293T cells with plasmids encoding the AAV Rep and Cap, and adenoviral helper functions, as well the recombinant genome containing the GBA construct. AAV2/8 particles were purified by aPOROS® CaptureSelect® affinity column and were titered by qPCR and characterised by alkaline gel analysis.
Mouse Study Design AAV viral particles carrying the GBA transgene under transcriptional control of the hepatocyte-specific promoters were administered into the tail vein of wild type (C57BL/6) male mice at age of 6-8 weeks. AAV dose ranged from $6 \times 10^{11}$ vg/kg to $6 \times 10^{12}$ vg/kg, as herein for each study. For each experiment, an additional group of animals was left untreated to serve as a control for the effects of treatment. To assess the kinetics and durability of transgene expression, serum GCase levels were measured at various time intervals (4-, 8-, and 12-weeks) post injection. Mice were followed up to 12 weeks post AAV treatment and sacrificed for biochemical and pathological analysis.
Serum and Tissue GBA Activity Assay β-Glucocerebrosidase (acid β-glucosidase; GCase) activity was determined fluorometrically with 4-Methylumbelliferyl-β-D-glucopyranoside (4MU-Glc) as a substrate. Serum samples were obtained from mouse blood and stored at −80° C. Tissues (liver, spleen, bone marrow) were harvested and snap frozen and lysed. β-Glucocerebrosidase (acid β-glucosidase, GCase) activity was determined fluorometrically with 4-Methylumbelliferyl-B-D-glucopyranoside (4MU-Glc) as a substrate. On the day of the assay, serum was diluted (0.5 µL, 1:50) and assayed in 50 mM Sodium Citrate, 25 mM Taurocholate, pH=5.75, 6 mM 4MU-Glc, for 30 min at 37° C. For tissue samples, the tissue protein lysate was assayed directly. The reaction was stopped by adding one volume (100 µl) of stop solution (0.5 M Glycine, 0.3 M NaOH, pH 10.0). Relative fluorescence levels (RFU) were evaluated with a Spectramax® I3X (Molecular devices) microplate reader using excitation and emission wavelengths of 365 nm and 445 nm, respectively. Fluorescence levels were then converted to nanomoles/h/mL (serum) or nmol/h/mg of total protein (tissue) based on a 4-Methylumbelliferone (4-MU, Sigma-Aldrich) standard curve.
Vector Genome Copy Number To determine the number of vector genomes per liver cell post-rAAV injection, DNA was isolated from frozen liver samples using QIAGEN DNeasy® Blood and Tissue Kit (QIAGEN) following manufacturers' instructions. Following DNA isolation, qPCR was performed using primer sets which bind to a region common to both LSP-S and LSP-L promoters, allowing estimation of AAV copy number.
Immunohistochemistry Rabbit anti-human GCase (Abcam ab125065; 1:100) was used to visualize GCase in mouse tissue. The rat anti-F4/80 (Abcam ab6640; 1:100) was used to visualize mouse macrophages. The formalin-fixed mouse tissues were deparaffinized with xylene and ethanol washes, followed by antigen retrieval according to Ventana® CC1 buffer product use recommendations. Immunohistochemistry staining was performed using the Ventana® Discovery XT instrument, using the Ventana® DAB Map detection Kit (760-124). Sections were counterstained with haematoxylin. FITC- and Texas red-conjugated secondary antibodies were used during immunofluorescent staining. DAPI was used to visualize nuclei. The signals were visualized by confocal fluorescence microscopy (Zeiss).
Huh-7 Transfection and Potency Assay The day before transfection, the liver hepatocyte cell line Huh-7 was plated in a 12 well plate at the cell density of $3 \times 10^5$ cells per well. For transfection, FuGENE® transfection reagent was used at the ratio of 4 µl per µg of plasmid and added overnight to Huh-7 cells in the presence of 10% of serum (foetal bovine serum, FBS). Transfection medium was changed, and cells were incubated for 24 hours with medium supplemented with Insulin-Transferrin-Selenium (ITS, ThermoFisher Scientific) and 25 mM Hepes buffer. Huh-7 cell transduction, was performed at defined multiplicity of infection (MOI) in the presence of serum for 24 hours, followed by a medium change and incubation for 24 hours in fresh medium. 20 µl of medium was used to measure GCase activity using 4MU-Glc as a substrate, as described above.
Statistical Analysis Statistical analysis was performed using Prism® 7 (Graph Pad) software. Columns analysis was performed by one-way ANOVA. P-values and sample size are indicated in Figure descriptions.

To approximate bioavailability (AUC), a one-phase decay model equation: $Y=(Y0-Plateau)*exp(-K*X)+Plateau$ was used in GraphPad Prism® software. Y0 is the Y-value when X (time) is zero and it is expressed in the same units as Y. Plateau is the Y-value at infinite times, expressed in the same units as Y. K is the rate constant, expressed in reciprocal of the X-axis time units (i.e. if X is in minutes, then K is expressed in minutes$^{-1}$). Tau is the time constant, expressed in the same units as the X-axis and is computed as the reciprocal of K. Half-life is in the time units of the X-axis, computed as $\ln(2)/K$. Span is the difference between Y0 and Plateau, expressed in the same units as the Y-values. The linear trapezoidal method was used for the AUC calculation. AUC is expressed as U*h/L where one unit is defined as the amount of enzyme required to hydrolyse 1 µmol/h of 4-methylumbelliferyl-β-D-glucopyranoside substrate at 37° C.

Example 2—GBA Constructs

In order to evaluate if a liver-directed gene therapy approach could be used to treat Gaucher disease (GD), the human full-length GBA coding sequence (as found in GenBank accession no. NM_000157.3; SEQ ID NO: 9) was cloned into a liver-specific promoter-driven adeno-associated virus (AAV) vector. In FLF-PL01 AAV construct (FIG. 1A) the GBA wild type sequence (GBAwt, non-codon-optimized) is driven by a liver-specific promoter referred to herein as 'LSP-S' (SEQ ID NO: 10). In order to determine a sequence optimal for expression, sequences were designed using a number of different codon optimisation strategies. In one example AAV construct (FLF-PL28) the GBA codon sequence was optimized and is driven by the same liver specific promoter LSP-S (FIG. 1B). The FLF-PL64 construct contains the same GBA codon-optimized sequence as FLF-PL28 but differs in containing a longer transcription regulatory element, referred to here as 'LSP-L' (SEQ ID NO: 14) instead of LSP-S (FIG. 1C).

Example 3—Analysis of Wild Type GBA Transgene Expression

In order to evaluate if the (wild type) GBA construct FLF-PL01 could lead to liver expression and subsequent secretion of β-glucocerebrosidase (GCase) into the bloodstream, FLF-PL01 was pseudotyped into AAV2/8. rAAV particles were produced and titered as described above, and characterised by alkaline gel analysis, prior to be used in mice. Eight-week-old wild type (C57BL/6) mice were treated with a single injection of AAV2/8-FLF-PL01 at a dose ranging from $6\times10^{11}$ to $6\times10^{12}$ vg/kg. Control (naïve) mice were left untreated. Serum samples were collected at four, eight, and 12 weeks post-AAV injection and used to evaluate levels of circulating active GCase. GCase activity was determined and immunohistochemistry staining was performed as described above. Sections were counterstained with haematoxylin.

Injection of wild-type mice with AAV2/8-FLF-PL01 resulted in an increase in expression of human GCase in the liver of treated animals (FIG. 2A). An increased level of GCase expression in liver could be observed with increased vector dose, with around 12-fold increase observed at the vector dose of $6\times10^{11}$ vg/kg group, 43-fold at the dose of $2\times10^{12}$ vg/kg, and 57-fold at the dose of $6\times10^{12}$ vg/kg (FIG. 2B). This data shows that AAV2/8-FLF-PL01 drove expression of GCase to levels that result in significant release of GCase to the bloodstream and possible access to macrophages in GD affected tissues.

Example 4—Analysis of In Vitro GCase Expression from Codon-Optimised Constructs

Figure 3:
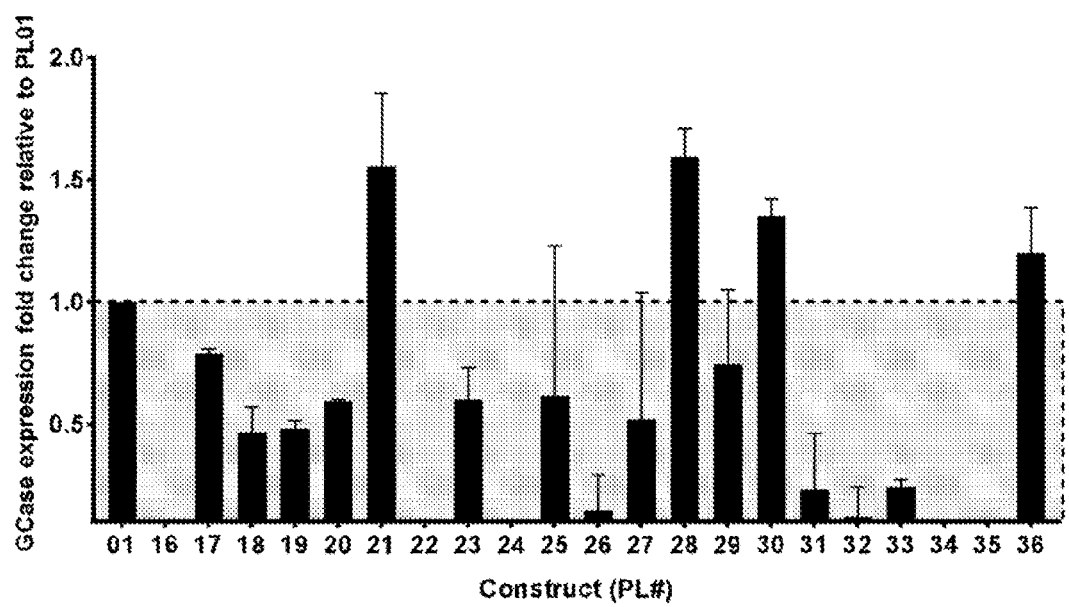
FIG. 3—Relative GCase levels observed for each tested GBA codon-optimised construct (FLF-PL16 to FLF-PL36; '16' to '36') upon transfection onto Huh-7 cells. Each construct was tested independently in 3 to 5 experiments. Data shown here represent GCase activity relative to wild type GBA construct FLF-PL01 ('01'). Error bars represent mean±SD.

Codon usage tables of various liver expressed sequences were used in order to generate GBA sequences codon-optimised throughout the stretch corresponding to the mature GCase protein (but not the signal peptide-encoding region). With the exception of one such codon-optimised GBA sequence ('FLF-PL36') the resulting sequences were then further manually altered to remove CpGs, cryptic splice sites, premature stop codons and unwanted amino acid substitutions. Twenty-one codon-optimised GBA sequences were created and tested for GCase expression levels upon transfection in the human liver cell line Huh-7. Huh-7 cells were plated onto a 12 well plate at the cell density of $3\times10^5$ per well and transfected as described above. Twenty microliters of medium was used to measure GCase activity using 4MU-Glc as a substrate. Results from this analysis allowed the identification of GBA codon-optimizations (FLF-PL21, -PL28, -PL30, and -PL36) that demonstrated increased expression of GCase (relative to wild type GBA sequence, FLF-PL01) when transfected in Huh-7 cells (FIG. 3).

Example 5—Analysis of In Vivo GCase Activity from Codon-Optimised Constructs

The four constructs (FLF-PL21, FLF-PL28, FLF-PL30 and FLF-PL36) identified in example 4 were pseudotyped as AAV2/8 and injection into wild-type mice at the dose of $2\times10^{12}$ vg/kg. Also included in the experiment was the non-codon-optimised construct FLF-PL01, as well as a construct (FLF-PL37) containing the same wild type GBA sequence as FLF-PL01 driven by the strong synthetic promoter CAG. Control (naïve) mice were left untreated. At time points up to 36 weeks after injection, animals were sacrificed, and serum and tissues samples were collected.

Figure 4:
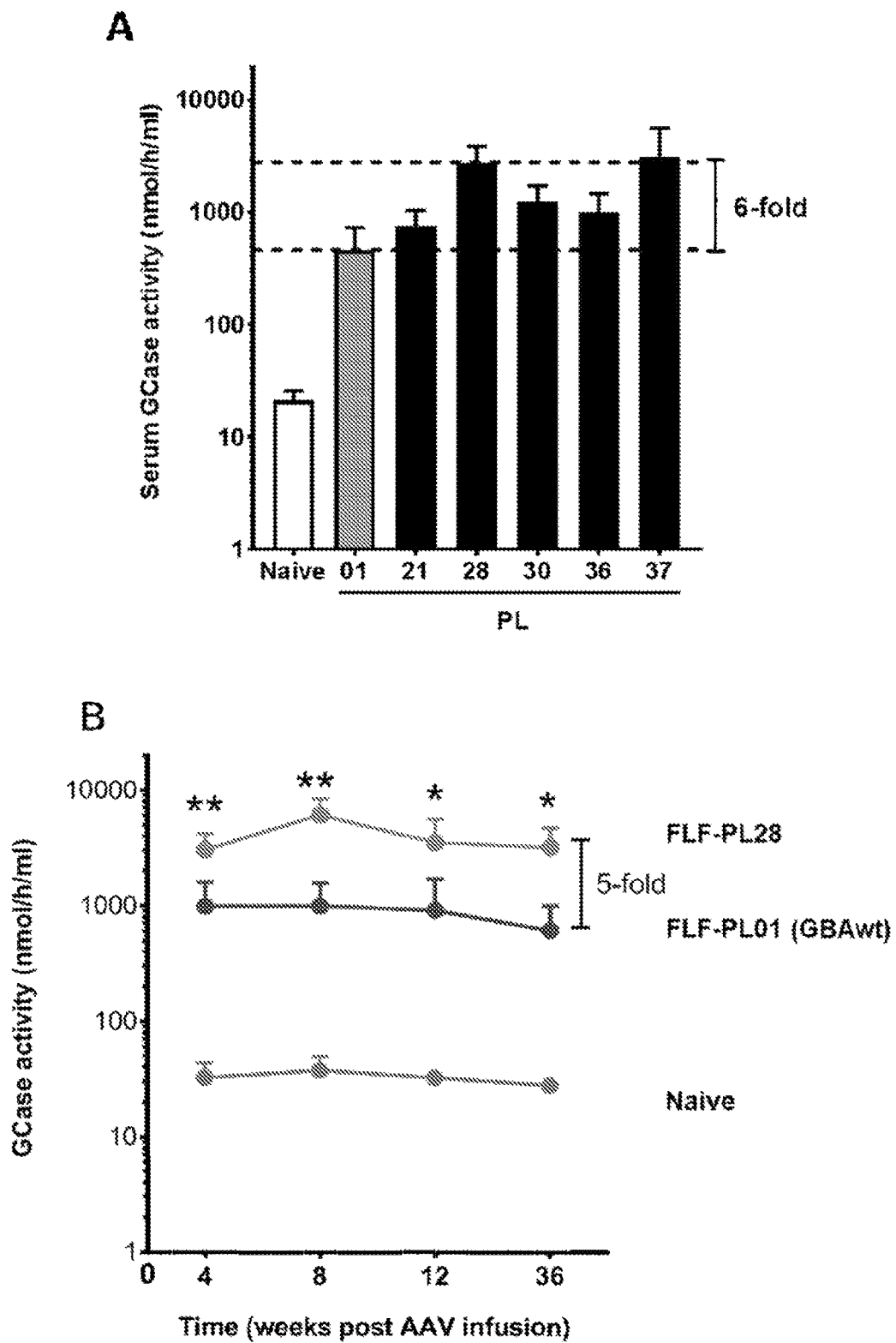
FIG. 4—Measurement of GCase activity present in the mouse bloodstream upon injection of vectors AAV2/8-FLF-PL-01, 21, 28, 30, 36 and 37 (see example 5 for description of constructs). (A) GCase activity levels found in mouse serum 8-weeks after injection of tested GBA constructs. (B) GCase activity levels observed in mouse serum at 4-, 8-, 12-, and 36-weeks post-injection of constructs FLF-PL01 and FLF-PL28. Error bars represent mean±SD, n=5-8 animals per experimental group. *$p \leq 0.05$; **$p \leq 0.001$ (one-way ANOVA).

FIG. 4A shows the results at 8 weeks post-injection of GCase activity found in mice injected either with the non-codon optimized GBA sequence driven by the LSP-S promoter (FLF-PL01), the codon-optimized GBA constructs (FLF-PL21, FLF-PL28, FLF-PL30 and FLF-PL36) also driven by the LSP-S promoter, and the GBA non-codon-optimized sequence driven by CAG promoter (FLF-PL37). All four GBA codon-optimized constructs showed increased levels of GCase activity present in the bloodstream when injected in mice (FIG. 4A), relative to FLF-PL01. The FLF-PL28 construct exhibited the greatest increase (about 6-fold) in GCase release to the bloodstream compared to the non-codon-optimised construct driven by the same LSP-S promoter (FLF-PL01). The elevated level of GCase driven by FLF-PL28 relative to FLF-PL01 was observed throughout the 36-week study period (FIG. 4B).

Of particular note, the levels of GCase observed in liver-specific promoter-containing FLF-PL28-injected mice were as high as the GCase levels driven by the FLF-PL37 construct in which wild type GBA sequence is expressed from the ubiquitous and strong CAG promoter (FIG. 4A).

Figure 5:
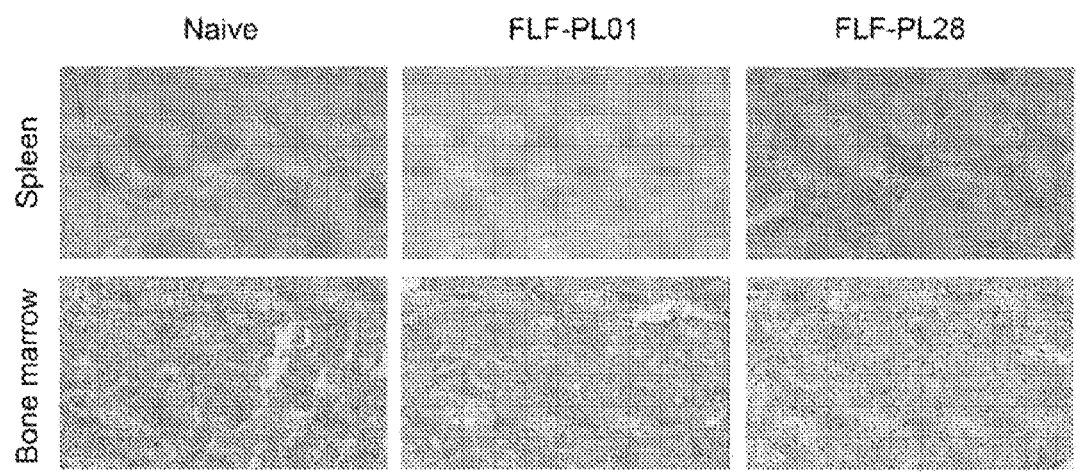
FIG. 5—Uptake levels of GCase in spleen and bone marrow tissue following AAV2/8-FLF-PL28 injection in wild type mice. Representative image of spleen and bone marrow tissue stained for GBA is shown for naïve or AAV2/8-PL28 treatment mice at 4-weeks post-injection. DAB (3,3'-Diaminobenzidine) was used to visualize GBA and haematoxylin was used as counterstain.

At end-stage, spleen and bone marrow were collected and fixed in formalin, followed by paraffin embedding. GBA immunostaining analysis performed on paraffin sections shows that, in agreement with the circulating GCase levels, tissue uptake of GCase is increased in mice treated with the FLF-PL28 GBA codon-optimised construct compared to non-codon-optimised construct FLF-PL01 (FIG. 5).

Figure 6:
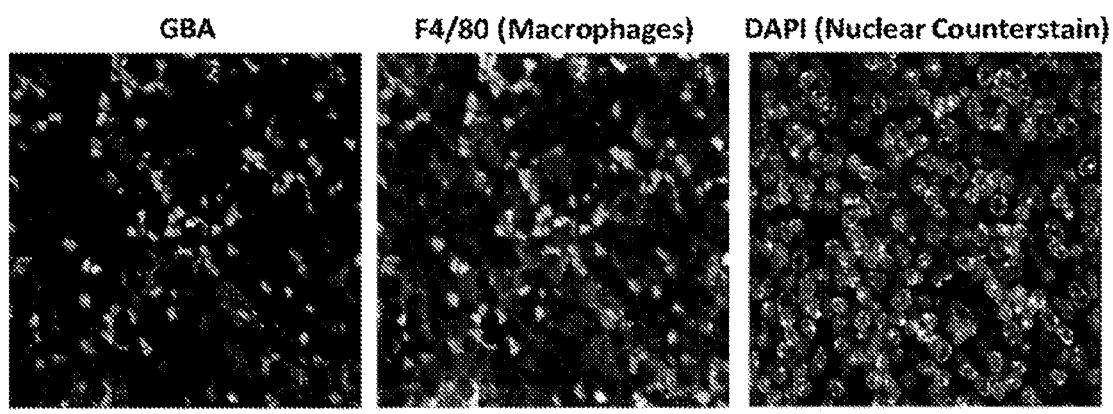
FIG. 6—Levels of co-localization of human GCase with canonical murine macrophage marker F4/80 observed in spleen upon injection of wild type mice with AAV2/8-FLF-PL28. Representative immunofluorescence image of spleen tissue stained for GBA and F4/80 antibodies. DAPI (Blue) was used to visualise nuclei.

In order to evaluate levels of macrophage uptake in spleen upon liver-directed GBA expression by FLF-PL28, immunofluorescence analysis with the mouse pan-macrophage marker F4/80 and a GBA antibody was performed. The majority of F4/80 positive cells display expression of the human-specific GBA, suggesting that the majority of GCase uptake in spleen occurs in macrophages (FIG. 6).

Example 6—Analysis of Promoter Effect on In Vivo GCase Activity

To test if promoter engineering could further increase expression from a GBA codon-optimised sequence, the GBA construct from FLF-PL28 was placed under a liver-specific promoter (referred to herein as 'LSP-L'; SEQ ID NO: 14) to generate construct FLF-PL64 (Example 2, FIG. 1C).

AAV2/8 vectors were prepared with the new construct and injected into wild type mice at the dose of $2\times10^{12}$ vg/kg. Control (naïve) mice were left untreated. After 5 weeks, animals were sacrificed, and serum and tissues were collected.

Figure 7:
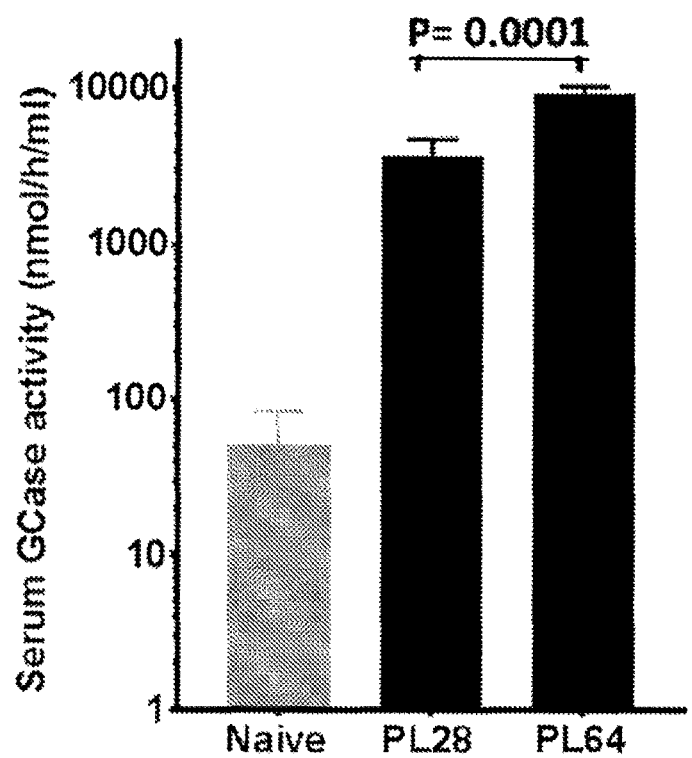
FIG. 7—Levels of GCase activity found in mouse bloodstream 4 weeks post-injection of AAV2/8-FLF-PL28 and FLF-PL64. GCase activity was determined for mouse serum collected 4-weeks post-injection at the dose of $2 \times 10^{12}$ vg/kg. Error bars represents mean±SD. N=5, C57BL/6 mice in each treatment group.

GCase activity analysis in serum shows that AAV2/8-FLF-PL64 results in an increased expression (about 2.5-fold, P=0.0001, one-way ANOVA) of GCase in the mouse bloodstream compared to mice treated with AAV2/8-FLF-PL28 (FIG. 7).

Figure 8:
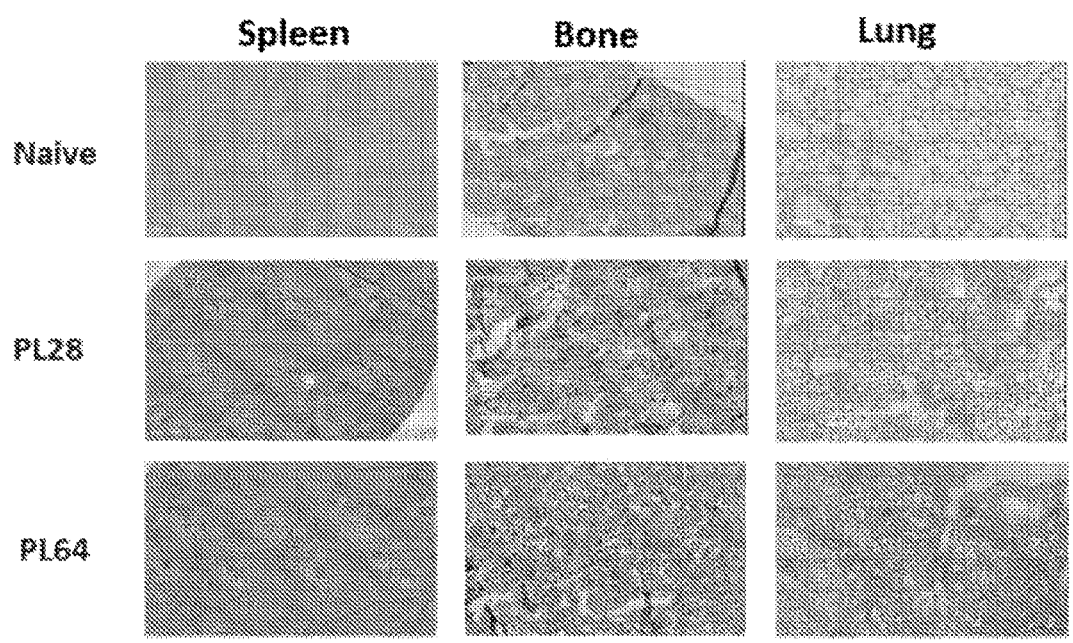
FIG. 8—Uptake levels observed in spleen, bone marrow and lung following AAV2/8-FLF-PL28 and FLF-PL64 injection observed in mice 5-weeks post treatment.

Like construct FLF-PL28, FLF-PL64 allows robust uptake of GCase into GD target tissues such spleen, bone marrow and lung (FIG. 8).

Example 7—Liver Expression Selectivity from AAV Vectors with GBA Constructs

To analyse the selectivity of the LSP-L promoter for a hepatic cell line, eight human-derived cell lines from a variety of tissues were selected. Details of each cell line and its origin are summarized in the table below.

TABLE 1

Human-derived cell lines evaluated in this example

| Cell line | Origin | Growth | Species of origin |
|---|---|---|---|
| HUH-7 | Hepatocellular carcinoma (Liver) | Adherent | Human |
| HEK293T | Kidney | Adherent | Human |
| PANC-1 | Pancreas (epithelioid carcinoma) | Adherent | Human |
| BxPC-3 | Pancreas (adenocarcinoma) | Adherent | Human |
| MCF7 | Breast (epithelial; adenocarcinoma) | Adherent | Human |
| 1643 | Neuroblastoma | Adherent | Human |
| MRC-9 | Normal lung fibroblast (embryo) | Adherent | Human |
| 697 | B-cell leukaemia (early B-cell) | Suspension | Human |

The eight human-derived cell lines as described above in Table 1 were grown in either DMEM, IMDM or RPMI media, supplemented with 10% FBS. For each cell line, $2 \times 10+$ cells/well were transduced at a multiplicity of infection (MOI) of $1 \times 10^5$ vg/cell with AAV-FLF-PL64 (AAV with liver tropic capsid=SEQ ID NO: 20). All experiments were performed in duplicate. Cells in suspension were counted and transduced in serum-free media (300 µl/well) into 48-well plates. For the adherent cell lines, media was aspirated, followed by washing with PBS (1×) and treatment with 5 ml of TrypLE™ enzyme for five minutes at 37° C., 5% $CO_2$, to dissociate the cells. The reaction was stopped by adding 5 ml of complete media. Dissociated cells were counted using a Countess™ II Automated Cell Counter (ThermoFisher) and centrifuged (250×g for five minutes), followed by resuspension in complete media at a density of $2 \times 10^5$ cells/ml. These cells were plated into 96-well plates ($2 \times 10+$ cells/well) to adhere for five hours prior to transduction. Transduction mix was prepared in X-VIVO™ media (50 µl/well) and added to the cells. After three hours, 100 µl/well of complete media was added. One day post-transduction, the media for each cell line was changed to complete media (+25 mM HEPES for secretion analysis).

GCase activity was determined fluorometrically with 4-Methylumbelliferyl-β-D-glucopyranoside (4MU-Glc) as substrate.

Figure 10:
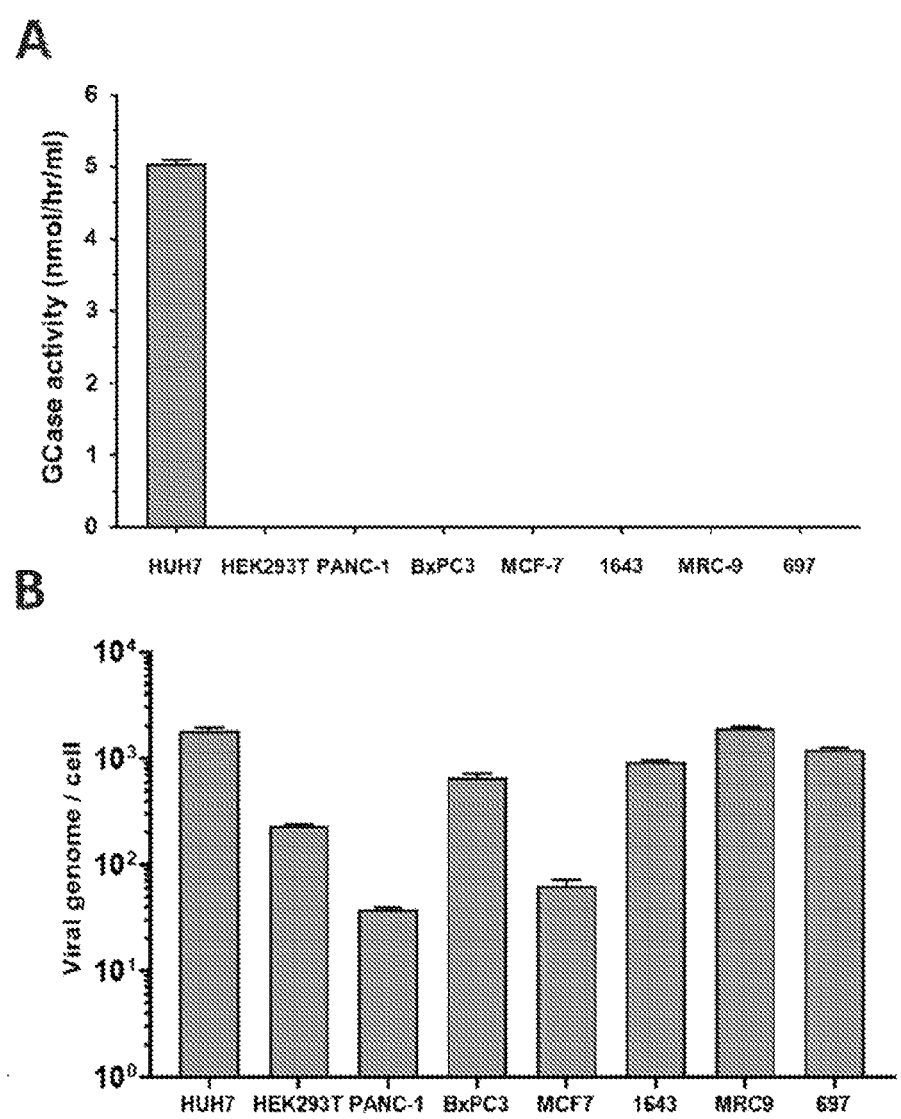
FIG. 10—Levels of GCase secretion by human-derived cell lines following transduction with AAV-FLF-PL64. Cells were transduced at a MOI of $1 \times 10^5$ vg/cell with the vector AAV-FLF-PL64. (A) Levels of active GBA were determined fluorometrically with 4MU-Glc as the substrate. (B) The level of transduction for each cell line was obtained by qPCR using primers specific for the polyA sequence. Blank values for each cell line were subtracted to obtain a value for the level of active GCase. Error bars represent mean±SD of duplicate wells.

GCase activity was measured from the culture supernatant for each cell line to determine the levels of GCase secreted following transduction with AAV-FLF-PL64 (FIG. 10). When the LSP-L promoter drives the GBA transgene, GCase secretion was detected in the HUH-7 cell line alone. The level of active GCase observed in HUH-7 cells was approximately 5.0 nmol/h/ml [5.1±0.1 nmol/h/ml]. No detectable levels of active GCase were observed for any of the other cell lines analysed.

Example 8—Comparison with ERT therapy

The goal of this example was to compare FLF-PL64 with the enzyme replacement therapy velaglucerase alfa (VPRIV®) (60 U/kg BW) when administered in mice as a single injection. Velaglucerase alfa (VPRIV®) contains the same amino acid sequence and a similar glycosylation pattern as the native enzyme, GCase (i.e. SEQ ID NO: 25), and therefore provides a suitable comparison. Patients undergoing enzyme replacement therapy (ERT) would be typically treated with an IV infusion of ERT (duration of infusion of 1-2 hours, clinical dose of velaglucerase alfa ((VPRIV®) is 60 U/kg) on alternate weeks.

Velaglucerase alfa enzyme replacement therapy (VPRIV®) powder (400 Units, Shire), for preparation of a solution for infusion, was obtained and maintained under refrigeration and protection from light until reconstitution. One vial (400 U) was reconstituted with 4.3 ml of sterile water to achieve a solution at 100 U/ml, as recommended by the manufacturer. Following reconstitution, the enzyme replacement therapy velaglucerase alfa (VPRIV®) solution was promptly snap frozen as single-use aliquots and stored at (−80° C.) for later use.

A single IV injection of either the enzyme replacement therapy velaglucerase alfa (VPRIV®) (60 U/kg BW) or FLF-PL64 (formulated as AAV2/8 particles, $2 \times 10^{12}$ vg/kg), was administered to wild type mice. Levels of active GCase in serum and tissue were determined at various time points for up to one week and also at three weeks and five weeks post-injection. The levels of active GCase were determined fluorometrically with 4-Methylumbelliferyl-β-D-glucopyranoside (4MU-Glc).

As shown in FIG. 11(A), the enzyme from the enzyme replacement therapy velaglucerase alfa (VPRIV®) is rapidly cleared from murine blood. The enzyme from the enzyme replacement therapy velaglucerase alfa (VPRIV®) reached a Cmax of 12.7 µmol/h/ml at two minutes post-injection; with an estimated half-life of approximately 5.6 minutes. At approximately 20 minutes post-injection, only residual levels of active GCase could be detected in serum. These levels remained close to untreated controls for the remainder of the study period. A comparison of treatment with the enzyme replacement therapy velaglucerase alfa (VPRIV®) or with FLF-PL64 was made by analysing mice with stable expression of GCase (FIG. 11B). Treatment with FLF-PL64 also led to increased levels of active GCase in murine blood (Cmax 9.4 µmol/h/ml) (FIG. 11B). However, although levels of active GCase were not as high as observed post-enzyme replacement therapy (velaglucerase alfa (VPRIV®)) injection, these levels remained constant for the duration of the study. Table 2 below shows the predicted bioavailability during a 2-week interval in mice following injection of either enzyme replacement therapy (ERT) or FLF-PL64.

TABLE 2

Predicted bioavailability (AUC) during a 2-week interval in C57BL/6 mice upon single injection of ERT (60 U/kg BW) or AAV-FLF-PL64 ($2 \times 10^{12}$ vg/kg).

| | ERT (VPRIV ®) | FLF-PL64 |
|---|---|---|
| $AUC_{2\ week}$ (min · U/ml) | 18.6 ± 5.6 | 3,161.6 ± 348.2 |

Figure 12:
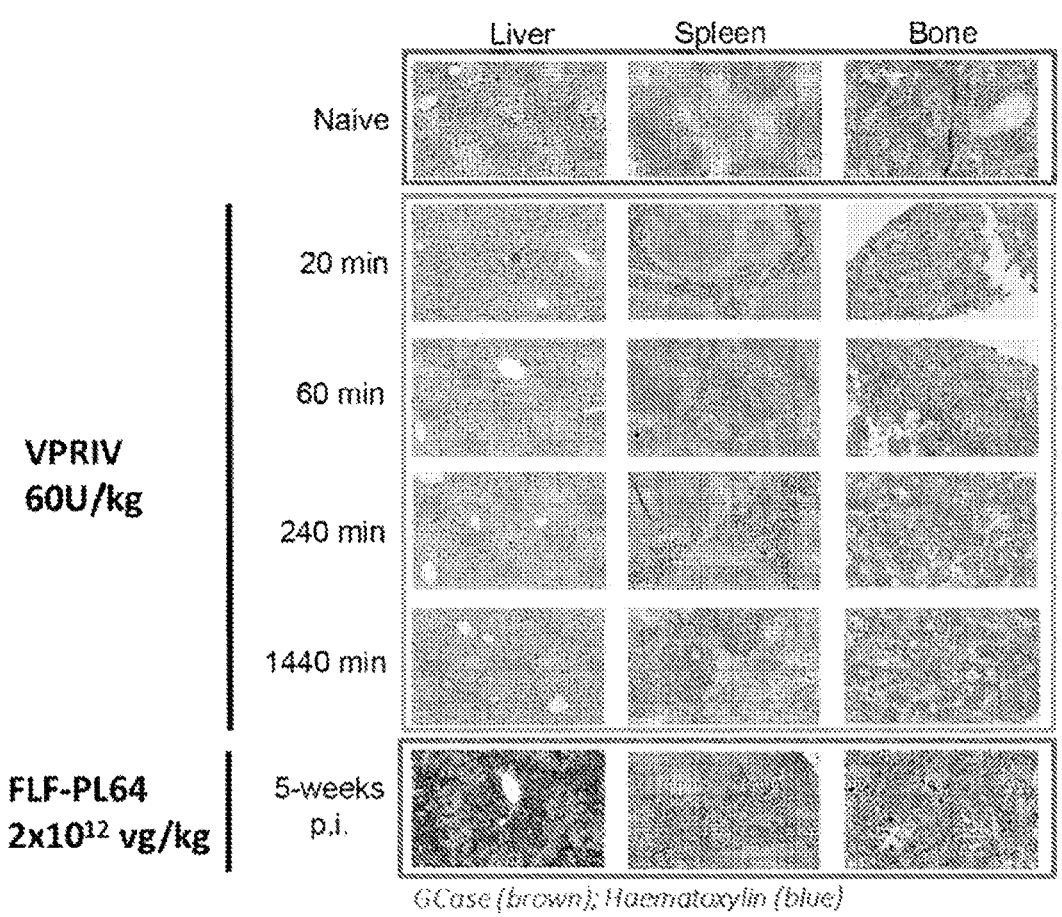
FIG. 12: GCase immunostaining in murine liver, spleen and bone following administration of the enzyme replacement therapy velaglucerase alfa (VPRIV®) or FLF-PL64. DAB (3,3'-Diaminobenzidine) was used to visualise GCase and haematoxylin was used as counterstain. FLF-PL64 samples were obtained at five weeks post-injection, while enzyme replacement therapy velaglucerase alfa (VPRIV®) treated samples were collected at the time labelled. Each image represents n=5, C57BL/6 mice for each treatment group. All pictures are at the same magnification.

FIG. 12 shows GCase immunostaining in murine liver, spleen and bone marrow following administration of enzyme replacement therapy velaglucerase alfa (VPRIV®) or AAV2/8-FLF-PL64. A representative image for each animal group is shown. DAB (3,3'-Diaminobenzidine) was used to visualise GCase and haematoxylin was used as counterstain. FLF-PL64 treated samples were obtained at five weeks post-injection, while enzyme replacement therapy (velaglucerase alfa (VPRIV®) treated samples were collected as labelled. A semi-quantitative analysis of the images are represented in Table 3 below:

TABLE 3

Relative levels of GCase immunoreactivity observed in murine liver, spleen and bone marrow post-administration of either ERT (VPRIV ®) or FLF-PL64. "−" refers to negative staining for GCase; "+" represents positive staining for GCase.

| Group | Liver | Spleen | Bone Marrow |
|---|---|---|---|
| Naïve | − | − | − |
| ERT - 20 min | + | ++ | ++ |
| ERT - 60 min | + | +++ | ++ |
| ERT - 240 min | + | −/+ | − |
| ERT - 1440 min | −/+ | − | − |
| FLF-PL64 | +++ | +++ | ++/+++ |

Example 9—In Vivo Study of Therapeutic Potential

1. Methods
Mouse Methods

9V/null mice carrying the Gba1 mutation D409V/D409V (9V/9V) were used as the Gaucher disease model in this study. 9V/null mice have a nearly normal lifespan with visceral abnormalities (inflammation and storage cells) and substrate accumulation (Xu et al. Am J Pathol. 2003 November; 163 (5): 2093-101; Xu et al. PLOS One. 2010 May 20; 5 (5): e10750). 9V/null mice were generated by crossing mice carrying Gba1 mutation D409V/D409V (9V/9V) and Gba1 null/WT. There are approximately two 9V/null produced in each litter. The strain background of 9V/null and WT mice are C57BL/6, 129SvEvBrd and FVB. 9V/null mice from multiple litters were randomly assigned into each treatment group on a rolling basis. Both male and female mice were enrolled in each group with an attempt to balance gender in the groups. All mice were housed under pathogen-free conditions and were monitored daily and weighed weekly. All AAV treated mice showed normal growth and weight gain.

At the end of the study, mice were euthanized by pentobarbital (100 mg/kg). Mice were transcardially perfused with saline. Liver, spleen and lung were then dissected.
AAV and Enzyme Replacement Therapy Velaglucerase Alfa (VPRIV®) Preparation and Administration Aliquots of AAV8-FLF-PL64 were stored at −80° C. Before injection, the aliquot was thawed on ice and diluted with X-VIVO™ 10 (Lonza, pH7.4, 4° C.), and gently mixed by vortexing briefly at low speed. The diluted AAV was kept on ice before injection and used within 2 hours.

The enzyme replacement therapy velaglucerase alfa (VPRIV®) was resuspended and aliquoted (25, 50, 100 µl) and stored at −80° C. Before injection, the aliquot was thawed on ice and diluted with acidified X-VIVO™ 10 (Lonza, pH5.5, 4° C.) to indicated dose, and gently mixed by vortexing briefly at low speed. The diluted enzyme was kept on ice before injection and used within 2 hours.

AAV ($2 \times 10^{12}$ vg/kg) and vehicle (X-VIVO™) were given one time to 9V/null mice at 8 weeks of age with indicated doses at 5 µL/g body weight (BW). WT mice were administrated with vehicle. AAV and vehicle administration were via tail vein to the mice while briefly under isoflurane. The enzyme replacement therapy velaglucerase alfa (VPRIV®) was administered by tail vein bolus injection to 9V/null mice anesthetized with mixture of isoflurane and oxygen in bio-bubble room at 60 U/kg and 2.5 µL/g BW, starting at 8 weeks of age, biweekly, for 7 injections.
Tissue Collection Blood (~100 µL) was collected from tail vein in a tube containing 0.5 M EDTA (5 µL) at 12 weeks, 16 weeks and 20 weeks of age. Freshly collected blood samples were kept on ice and separated to plasma to assay for GCase activity within 2 hours. Each plasma collection and activity assay from the enzyme replacement therapy velaglucerase alfa (VPRIV®) treatment group was performed within 2 hours after the scheduled enzyme injection. A separate portion of blood (~400 µL) was processed to isolate white blood cells (WBC) for GCase activity assay. Collected WBC was stored at −80° C.

Tissues (liver, lung, spleen, bone marrow) were collected at experimental endpoint (20 weeks of age). Tissue collection from the enzyme replacement therapy velaglucerase alfa (VPRIV®) group was performed within 2 hours after the final scheduled enzyme injection. Liver, lung and spleen samples were divided into 4 parts, with 3 parts frozen in individual tubes and stored at −80° C. prior to GCase activity assay, protein and substrate analysis. The remaining part was fixed in 10% Formalin for histology analysis. Bone marrow cells were collected from femurs and tibias of both legs of the mice and frozen in two tubes stored at −80° C. freezer for GCase activity and substrate assays.
GCase Activity Assay Tissues were homogenized in 1% Na taurocholate and 1% Triton X-100® (Tc/Tx) using a Precellys® Evolution tissue homogenizer for two cycles (20 seconds each, 30 seconds interval) at 4° C. Cells (bone marrow (BM) and white blood cells (WBC)) were homogenized in 1% Tc/Tx with sonication at 4° C. Tissue and cell lysates (2 µL) were diluted (5×) with reaction buffer in assay mixture (0.025 M Citrate-phosphate buffer, pH5.6). Diluted lysates (10 µL) (in triplicate per sample) were loaded to reaction plate. GCase activity was determined fluorometrically with 4-methylumberlliferyl-β-D-glucopyranoside (4MU-Glucose, 4 mM) (Biosynth AG, Switzerland) in the presence and absence of 2 mM Conduritol B epoxide (Millipore. CA) incubated for 1 hour at 37° C. Protein concentrations were determined using BCA Protein Assay Reagent (Pierce, Rockford, IL).

Plasma was diluted in 0.025 M Citrate-phosphate buffer, pH5.6. GCase activity was determined fluorometrically with 4-methylumberlliferyl-β-D-glucopyranoside (4MU-Glucose, 4 mM) (Biosynth AG, Switzerland) as above.
Substrate Analysis Frozen tissues were weighed and homogenized in 3.6 mL of Methanol/Chloroform/$H_2O$ (2:1:0.6 v/v/v). Aliquots (500 µL) of lysate were subjected to LC/MS analysis. The quantitated hexosylceramide and hexosylsphingosine were normalized by tissue weight.

Plasma was diluted in water (40 µL plasma+60 µL water) and subjected to LC/MS analysis. Substrate level was normalized by plasma volume.

Bone marrow cells were suspended in 200 µL water and sonicated and vortexed to make cell lysate. 160 µL lysate was subjected to LC/MS analysis. Remaining lysate was determined for protein concentration. Substrate level was normalized by mg protein.

LC/MS analysis was performed to analyse hexosylceramide and hexosylsphingosine concentrations. Since galatosylceramide and galatosylsphingosine levels are very low in this mouse model model, measured hexosylceramide and hexosylsphingosine concentrations represent levels of glucosylceramide and glucosylsphingosine, respectively.

Histology Analysis

Liver, lung, spleen and bone marrow were dissected from saline perfused mice and fixed in Formalin (10%) and paraffin embedded. Fixed tissues were cut into 4 µm sections and mounted on slides.

Storage Cell Count

Tissue sections were stained with hematoxylin and eosin (H&E) by Autostainner (Leica Autostainner XL). The stained tissues were scanned with Aperio AT2 (Leica, 40×). The tissue images were processed with Aperio ImageScope (V12.4.0.0543). 10 photos of 20× magnitude (500 µm×800 µm image) from liver and lung per mouse were chosen for analysis. Storage cells were counted from each image. Average of cell counts from 10 images was calculated for data graph. Definition of "storage cells" is based on the size of cells (macrophage), e.g. size of storage cells in liver is >10 µm, in lung is >15 µm.

CD68 Staining and Quantification

Tissue sections were stained with rabbit anti-mouse CD68 antibody (1:25. Abcam Ab53444) in Discover Ultra automated IHC/ISH slide staining machine. The tissues were counter-stained with hematoxylin on cell nuclei. Stained tissues were scanned with Aperio AT2 (Leica, 40×) and the images were acquired by Aperio ImageScope (V12.4.0.0543). The images of liver and lung at 20× magnitude (500 µm×800 µm) were used for quantitative analysis. IHC signals from 5 images of liver or lung per mouse were analysed using Image J (Fiji, v5.1). Average CD68 signals per mouse was calculated for data graph.

Statistical Analyses

The data was analysed by Student's t-test or OneWay ANOVA. Figure graphs and statistical analysis were generated by PRISM® 8 software (PRISM® version 8.0.1).

2. Results

GCase Activity

AAV-FLF-PL64 treatment to restore active GCase levels in 9V/null mice was studied by measuring GCase activity in cells and tissues. White blood cells (WBC), bone marrow and tissue samples were collected at the experimental end point as above (i.e. 12 weeks post AAV-FLF-PL64 injection or on the final enzyme replacement therapy velaglucerase alfa (VPRIV®) administration), when the mice are at 20 weeks of age.

Figure 13:
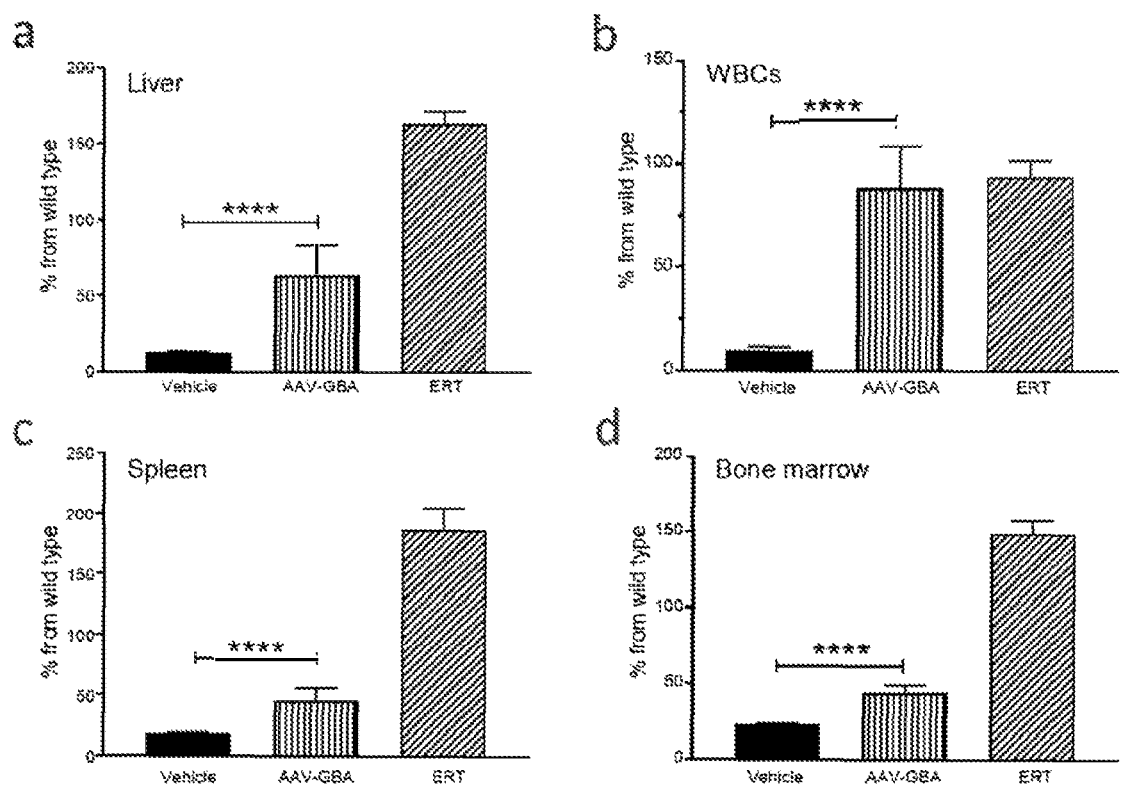
FIG. 13: Increase in GCase activity observed in $gba^{9v/null}$ mouse liver (a), white blood cells (b), spleen (c), and bone marrow (d) upon administration of labelled enzyme replacement therapy (labelled ERT) velaglucerase alfa (VPRIV®) or AAV-GBA (AAV-FLF-PL64). Labelled ERT samples were collected 1-2 hours post the last injection corresponding to peak of uptake in tissues. AAV-GBA (AAV-FLF-PL64) samples were collected 12 weeks post-injection and corresponding to steady state levels of uptake. GCase activity is represented as a percentage of the activity measured in wild-type healthy mice (at 20 weeks of age). All mice were treated at age of 8-week pre-overt symptomatology. ERT at dose 60 U/kg and administered by injection every two weeks; AAV-FLF-PL64 injected at dose of $2 \times 10^{12}$ vg/kg. n=10. **$P \leq 0.0001$

The enzyme replacement therapy velaglucerase alfa (VPRIV®) was shown to increase the activity across all cells and tissues tested (FIG. 13). As stated above, tissues of the enzyme replacement therapy velaglucerase alfa (VPRIV®) treated group were collected within 2 hours post last injection, and this is in line with previous data showing that this is within the period where the enzyme replacement therapy velaglucerase alfa (VPRIV®) is at its C-max in the tissues.

AAV-FLF-PL64 was shown to also significantly increase GCase activity in all tissues following only a single administration (FIG. 13). Compared to Vehicle-9V/null, liver GCase activity increased by 4.7-fold, and spleen GCase activity increased by 2.5-fold. In white blood cells GCase activity was seen to significantly increase in the AAV-FLF-PL64 treated groups by 7-9 fold. In particular, the GCase activity level in white blood cells reached to about 82% of WT activity levels.

Tissue Histology

Visceral pathology in 9V/null mice was determined by counting foamy macrophages as storage cells and quantitating CD68 staining signals on activated macrophages. The storage cells were counted in H&E stained liver sections. CD68 signal (brown colour) intensity was quantified on anti-CD68 antibody stained liver and lung sections.

Figure 14:
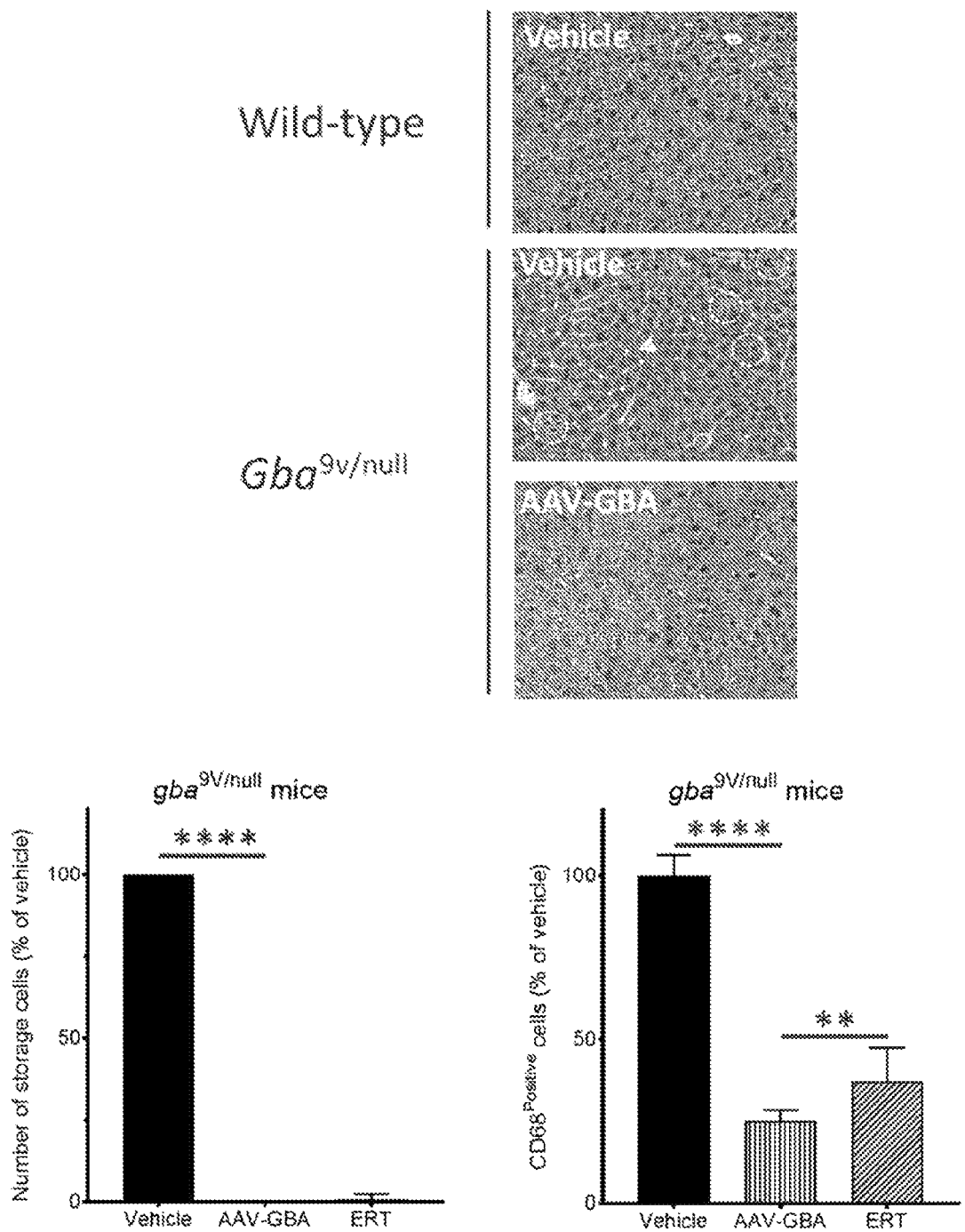
FIG. 14: AAV-GBA (AAV-FLF-PL64) gene therapy reduces activated macrophages and inflammation in the liver of $gba^{9v/null}$ mice. Upper panel: H&E stained liver sections showing a representative image from each group. Storage cells are identified by circles. Lower left panel: graph showing comparison between storage cells counted in AAV- FLF-PL64 and ERT treated groups compared to vehicle control groups. Lower right panel: graph showing CD68positive cells counted in AAV-FLF-PL64 and ERT treated groups compared to vehicle control groups following staining with anti-CD68 antibody. AAV-GBA (AAV-FLF-PL64) injected at dose of $2\times10^{12}$ vg/kg; samples collected 12-weeks p.i. ERT at dose 60 U/kg and administered by injection every two weeks. ERT samples were collected 1-2 hours post the last injection. Mean±SEM, (n=10), P≤0.005, ****P≤0.0005

Storages cells at size ≥10 µm in liver were counted from 10 images per tissues of each mouse. In liver, the number of storage cells was undetectable in the AAV-FLF-PL64 treated groups, as well as in the enzyme replacement therapy velaglucerase alfa (VPRIV®) treated group. (FIG. 14)

CD68 signals in liver were also significantly decreased in the AAV-FLF-PL64 treated groups. AAV-FLF-PL64 treatment reduced CD68 signals to about 25% of Vehicle-9V/null level. In comparison, CD68 signals in enzyme replacement therapy velaglucerase alfa (VPRIV®) treated group was about 37% of Vehicle-9V/null level. (FIG. 14)

Substrate Accumulation

9V/null mice are known to develop glycolipid substrates accumulation in liver, lung and spleen (Xu et al. PLOS One. 2010 May 20; 5 (5): e10750). For example, the study showed that hexosylceramide in the control Vehicle-9V/null group is above WT level by 7.97-fold in liver and 3.57-fold in spleen (data not shown).

AAV-FLF-PL64 treated groups showed significant reduction of hexosylceramide and hexosylsphingosine in the liver and spleen compared to Vehicle-9V/null (FIG. 15). In particular, AAV-FLF-PL64 treated groups had hexosylceramide levels reduced to 1.20-fold times the wild-type level in liver and 1.03-fold times the wild-type level in spleen (data not shown). Similar reduction to close to the WT level was seen upon analysis of bone marrow (data not shown).

On the other hand, the enzyme replacement therapy velaglucerase alfa (VPRIV®) treatment only showed a significant reduction of hexosylceramide in liver, with the other tested tissues showing no significant changes in the hexosylceramide levels. Treatment with the enzyme replacement therapy velaglucerase alfa (VPRIV®) did not appear to have any significant effect on hexosylphingosine levels in any tested tissue.

It will of course be understood that, although the present invention has been described by way of example, the examples are in no way meant to be limiting, and modifications can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication was specifically and individually indicated to be incorporated by reference herein.

The invention claimed is:

1. A non-wild type polynucleotide comprising a beta-glucocerebrosidase (GBA) nucleotide sequence, wherein the GBA nucleotide sequence encodes a β-Glucocerebrosidase (GCase) protein, wherein the GBA nucleotide sequence comprises a sequence that is at least 95% identical to SEQ ID NO: 1, and wherein the GCase protein encoded by the GBA nucleotide sequence has GCase activity and expresses in human liver cells at higher levels compared to a GCase encoded by a wild type GBA nucleotide sequence.

2. The non-wild type polynucleotide of claim 1, wherein the GBA nucleotide sequence is codon optimized for expression in human liver cells.

3. The non-wild type polynucleotide of claim 1, wherein the GBA nucleotide sequence comprises a reduced number of CpGs compared to a wild type GBA nucleotide sequence.

4. The non-wild type polynucleotide of claim 1, wherein the non-wild type polynucleotide further comprises a transcription regulatory element.

5. A viral particle comprising a recombinant genome comprising the non-wild type polynucleotide of claim 1.

6. A pharmaceutical composition comprising the non-wild type polynucleotide of claim 1 and a pharmaceutically acceptable excipient.

7. A pharmaceutical composition comprising the viral particle of claim 5 and a pharmaceutically acceptable excipient.

* * * * *